United States Patent
Martin et al.

(10) Patent No.: US 11,857,958 B2
(45) Date of Patent: Jan. 2, 2024

(54) CELL CO-CULTURE CHIP AND PROCESS FOR THE PRODUCTION THEREOF

(71) Applicant: UNIVERSITE GRENOBLE ALPES, Saint Martin d'Heres (FR)

(72) Inventors: Donald Keith Martin, Gieres (FR); Nathalie Picollet-D'Hahan, La Ferriere (FR)

(73) Assignee: UNIVERSITE GRENOBLE ALPES, Saint Martin d'Heres (FR)

( * ) Notice: Subject to any disclaimer, the term of this patent is extended or adjusted under 35 U.S.C. 154(b) by 1451 days.

(21) Appl. No.: 16/300,504

(22) PCT Filed: May 11, 2017

(86) PCT No.: PCT/FR2017/051148
§ 371 (c)(1),
(2) Date: Feb. 13, 2019

(87) PCT Pub. No.: WO2017/194894
PCT Pub. Date: Nov. 16, 2017

(65) Prior Publication Data
US 2019/0168216 A1    Jun. 6, 2019

(30) Foreign Application Priority Data
May 11, 2016    (FR) ...................... 16/54213

(51) Int. Cl.
*B01L 3/00*    (2006.01)
*C12M 3/00*    (2006.01)
(Continued)

(52) U.S. Cl.
CPC ....... *B01L 3/502707* (2013.01); *C12M 21/08* (2013.01); *C12M 23/16* (2013.01); *C12M 25/00* (2013.01); *C12M 25/04* (2013.01)

(58) Field of Classification Search
CPC ...... C12M 23/16; C12M 25/04; C12M 25/00; C12M 21/08; B01L 3/502707;
(Continued)

(56) References Cited

U.S. PATENT DOCUMENTS 7,494,811 B2 *    2/2009    Wolfinbarger, Jr. et al. ................
C12N 5/0654
435/375
8,580,209 B2 *    11/2013    Kurowski et al. ..........................
B29C 66/53461
422/503

(Continued)

FOREIGN PATENT DOCUMENTS

JP    2004065087 A    3/2004
JP    2005143343 A    6/2005
(Continued)

OTHER PUBLICATIONS

Hyun et al., "Gut-on-a-Chip Microenvironment Induces Human Intestinal Cells to Undergo Villus Differentiation", Integr. Biol. 5(9), 1130-1140 (Year: 2103).*
(Continued)

*Primary Examiner* — Lydia Edwards
(74) *Attorney, Agent, or Firm* — HAUPTMAN HAM, LLP

(57) ABSTRACT

A microfluidic cell culture chip which contains a central module comprising a central unit, which contains a support consisting of a non-resorbable membrane, a 3D nanostructured porous membrane, comprising at least one protuberance, and the 3D nanostructured porous membrane and that at least one protuberance being composed of materials suitable for the culture of two distinct cell types; a base, and the central unit being integrated in the base, and forming a whole with the base.

20 Claims, 41 Drawing Sheets

Figure 1:
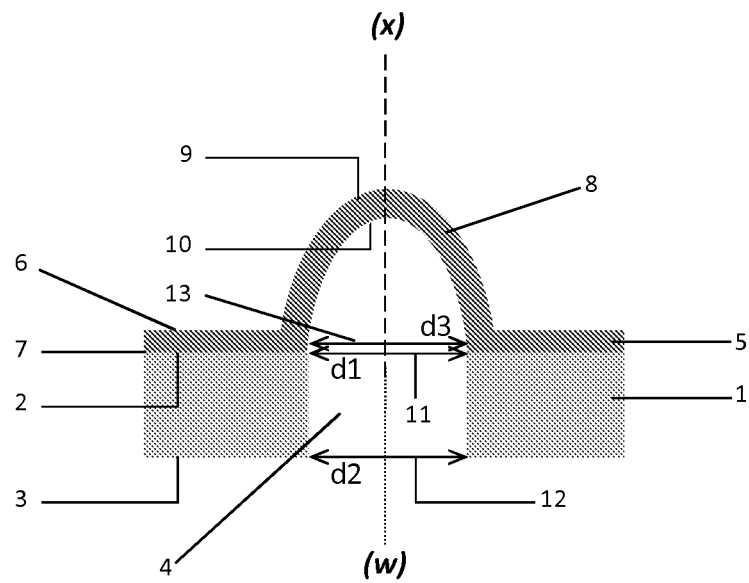

(51) Int. Cl.
*C12M 3/06* (2006.01)
*C12M 1/12* (2006.01)

(58) Field of Classification Search
CPC ....... G01N 2033/4975; G01N 33/0029; G01N 33/0037; G01N 33/497; A61B 2560/0247; A61B 2562/0247; A61B 5/082; A61B 5/087; A61B 5/097; A61B 5/08
See application file for complete search history.

(56) References Cited

U.S. PATENT DOCUMENTS

| | | | | |
|---|---|---|---|---|
| 8,647,861 | B2 * | 2/2014 | Ingber et al. ........ | C12N 5/0688 506/10 |
| 2017/0101628 | A1 | 4/2017 | Ingber et al. | |

FOREIGN PATENT DOCUMENTS

| | | |
|---|---|---|
| JP | 2011528232 A | 11/2011 |
| JP | 2012509663 A | 4/2012 |
| JP | 2014506801 A | 3/2014 |
| WO | 2010009307 A2 | 1/2010 |
| WO | 2010059583 A1 | 5/2010 |
| WO | 2011014674 A2 | 2/2011 |
| WO | 2011094486 A2 | 8/2011 |
| WO | 2012032646 A1 | 3/2012 |

OTHER PUBLICATIONS

International Search Report from corresponding International Application No. PCT/FR2017/051148, dated Jul. 14, 2017, pp. 1-3, European Patent Office, Rijswijk, The Netherlands.

Daverey et al., A., "Breast Cancer/Stromal Cells Coculture on Polyelectrolyte Films Emulates Tumor Stages and miRNA Profiles of Clinical Samples," Department of Chemical and Biomolecular Engineering, University of Nebraska—Lincoln, pp. 9991-10001, Aug. 2015.

Japanese Office Action issued in corresponding Japanese Application No. 2018559754, dated Jan. 25, 2021, pp. 1-2.

* cited by examiner

CELL CO-CULTURE CHIP AND PROCESS FOR THE PRODUCTION THEREOF

The present invention relates to a microfluidic cell culture chip comprising a plurality of parts, each referenced by the term "module", and likely to be assembled two by two.

The present invention also relates to a process for producing said chip, as well as the uses thereof in the field of diagnostics.

TECHNOLOGICAL BACKGROUND

Numerous current devices developed with the aim of mimicking organs on a chip, consist of 2D membranes.

In U.S. Pat. No. 8,647,861 B2 by Ingber et al., filed on 13 Oct. 2011, the authors have developed an organomimetic device making it possible for a co-culture of adherent cells on either side of a membrane, equipped with means, making it possible to create a differential pressure around the membrane, thus generating the expansion or the retraction of it, in order to reproduce the mechanical stresses existing in vivo at a tissue/tissue interface. This device, based on a microfluidic system comprising a flexible porous membrane made of polydimethylsiloxane (PDMS), at the interface of two microfluidic ducts, making it possible for the circulation of fluids along said membrane, in particular makes it possible to mimic pulmonary alveoli during breathing.

In US 2014/0038279 A1 by Ingber et al., filed on 28 Feb. 2012, the authors propose a cell co-culture system making it possible to reproduce natural intestinal epithelial structures and mimic the behaviour thereof. This organomimetic device, based on a microfluidic system, comprises a PDMS porous membrane, positioned at the interface of two microfluidic ducts making it possible for the circulation of fluids along said membrane, and on which is cultured a layer of intestinal epithelial cells on at least one of the sides. The coupling of the membrane with support elements leads to a movement of elongating the membrane in at least one dimension, and thus makes it possible to reproduce the movement of the tissues in vivo.

Even if these devices make it possible to recreate tissue/tissue interfaces as well as the mechanical stresses existing in vivo, to mimic the microarchitecture of organs, the cell co-culture remains on a 2D medium, and do not make it possible to reproduce the topography of certain organs.

In 2013, Kim et al., in their publication entitled, "*Gut-on-a-Chip microenvironment induces human intestinal cells to undergo villus differentiation*", Integr. Biol., 5, 1130, propose an organomimetic microfluidic chip thus making it possible to reproduce 3D intestinal villi, like those formed in vivo in the intestine. This chip, based on a microfluidic system, comprises a PDMS porous membrane positioned at the interface of two microfluidic ducts, making it possible for the circulation of fluids along said membrane, and on which are cultured Caco-2 intestinal epithelial cells which spontaneously form villi beyond two days of culture in the presence of a constant flow of medium of 30 µL/h.

All these devices however propose a cell co-culture on a PDMS porous membrane, which is not optimal in terms of biocompatibility (inertia, porosity). The PDMS can absorb small organic components, also drugs and a permeability to gases which could impede certain applications. Moreover, the PDMS membranes can have intrinsic transportation, mechanical and structural properties which are different from those like the natural basal membrane of the tissue. By recreating these types of interfaces, the authors favour the reproduction of the microarchitecture of the organ.

In 2014, March et al., in their publication entitled, "*Differentiating Intestinal Stem Cells in a 3D Niche*", propose an in vitro intestine model using polylactic glycolic acid structures, having the 3D morphology of microvilli and capable of supporting a co-culture of different types of epithelial cells on the surface thereof, such as a co-culture of Caco-2 and HT29-MTX intestinal epithelial cells. This model makes it possible to obtain a cell differentiation on the surface of the microvilli in a similar manner to the intestines in vivo.

Thus, even if certain current devices have structures, made of PDMS or of PGLA, making it possible to mimic the microvilli of organs, the detection of known markers is done by immunofluorescence after attachment of the cells and marking using an antibody, which therefore implies the lysis of the cells for the analysis.

Numerous publications state that the cells in culture on the 3D structures do not have the same properties as the same cells cultured in 2D; differences are indeed observed in the gene and protein expression profile, the adhesion of the cells, the proliferation speed and the cell differentiation. In addition, the metabolic response to drugs of a cell type is different, according to which the cells are cultured in 2D and in 3D, as Kim et al. have shown in 2013, in their publication entitled, "*Gut-on-a-Chip microenvironment induces human intestinal cells to undergo villus differentiation*", Integr. Biol., 5, 1130, where they made a comparison, between the Transwell® 2D culture model and a culture model comprising 3D structures mimicking microvilli, of the activity of the cytochrome enzyme P450 metabolising drugs, and show that in 2D, the activity remains unchanged during the culture, while in 3D, this activity increases during the formation of microvilli then is stabilised.

The topography of the cell medium having a significant impact on the behaviour of the cells, it is therefore important to reproduce, as precisely as possible, the in vivo conditions of the cells, in order to develop reliable models of cell culture.

SUMMARY

In the present invention, the inventors have developed a cell co-culture microfluidic chip, mimicking the microvilli of organs with an acinar/tubular structure and the luminal microenvironment.

The microfluidic chip according to the invention comprises a membrane made of porous biomaterials which comprises folds thus forming 3D hollow protuberances on which are cultured adherent cells on either side of said membrane at the protuberances. The coupling of this membrane with a microfluidic system makes it possible to recover the cell secretions during the culture thereof to analyse the composition thereof.

Thus, contrary to the prior art, where the markers are detected by an immunomarking on attached cells therefore implying the death of the cells (Kim et al., 2013), the chip according to the invention makes it possible to carry out these detections in the secretions of the cells cultured on the protuberance, which are recovered by the microfluidic system.

The chip according to the invention thus makes it possible to collect secretions on living cells and consequently, to collect the secretions a different times during the culture, even over several days to carry out kinetic studies, while maintaining the viability and the functionality of the cells over time.

These secretions consist of all the molecules which could be secreted in the cell culture medium such as peptides, proteins, amino acids, miRNA, DNA, RNA.

The analysis profile of these secretions make it possible to obtain the secretome, i.e. the qualitative and quantitative profile of the components of the secretions.

Figure 39:
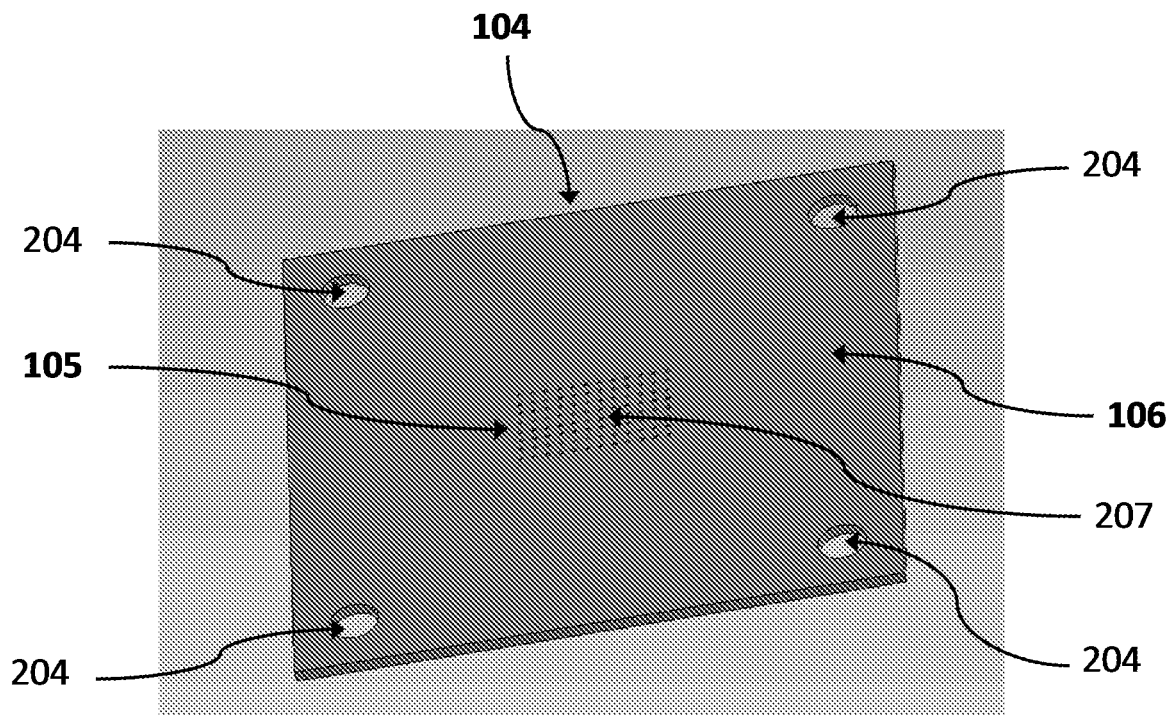
Figure 40:
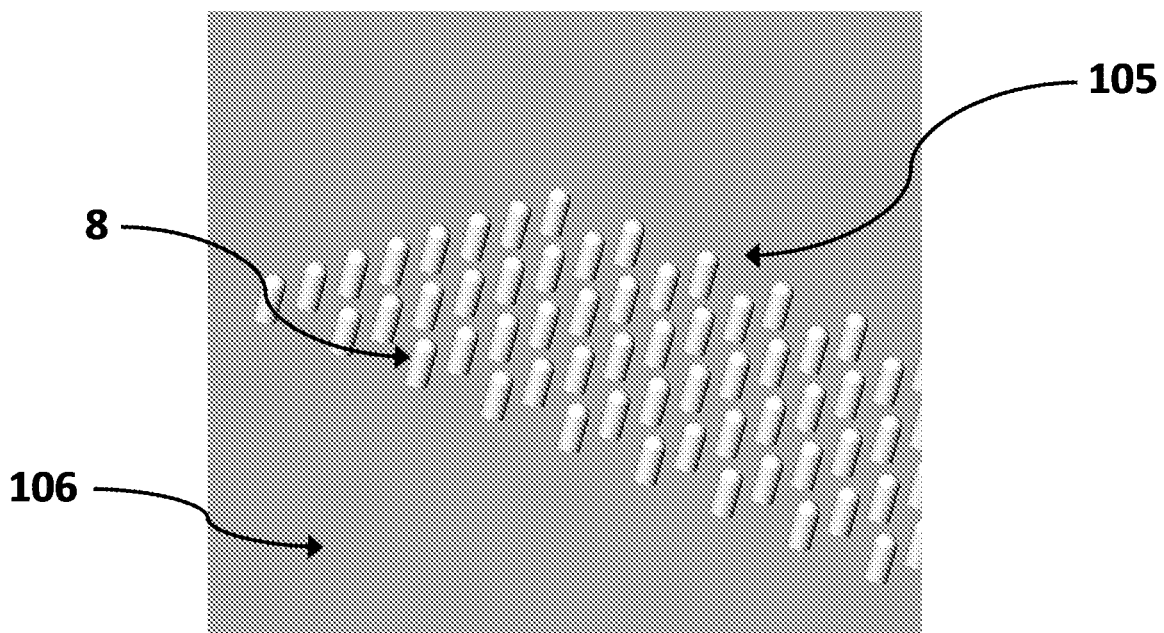

The present invention relates to a microfluidic cell culture chip which contains a central module (104) comprising:
 a central unit (105), which contains
  a support consisting of a non-resorbable membrane (1), comprising an upper face (2) and a lower face (3), perforated by at least one perforation (4),
  a 3D nanostructured porous membrane (5), comprising an upper face (6) and a lower face (7), and comprising at least one protuberance (8), said at least one protuberance comprising an outer face (9) and an inner face (10) and forming a relief structure on the side of the upper face (6) of the 3D nanostructured membrane (5) (FIG. 40),
  said lower face (7) of said 3D nanostructured porous membrane (5) being positioned secured to said upper face (2) of said support (1),
  or said upper face (6) of the 3D nanostructured membrane (5) being positioned secured to said lower face (3) of said support (1),
  and said 3D nanostructured porous membrane (5) and the at least one protuberance (8) being composed of materials suitable for the culture of two distinct cell types;
 a base (106),
said central unit (105) being integrated in said base (106), and forming a whole with said base (106) (FIGS. 39 and 40).

The expression, "non-resorbable membrane" means that the membrane cannot be removed by a physical process, nor by a chemical process in an aqueous solvent.

The expression, "perforation" which relate to the support, means an opening passing through the support from one end to the other, i.e. an opening through the support between the lower face and the upper face, thus making it possible for the communication between these two faces.

This perforation of said support creates an empty space through said support, and is characterised by a section at the upper face of said support and a section at the lower face of said support.

The expression, "protuberance" which relates to the 3D nanostructured porous membrane means a projecting protrusion forming a relief structure, on the side of the upper face of said 3D nanostructured porous membrane.

The expression, "porous" which relates to the 3D nanostructured porous membrane means that said membrane comprises continuous pores interconnected to one another, of a diameter of between 2 and 10 nm, extending from the upper face to the lower face of said membrane. These pores making it possible for gas exchanges through the membrane, as well as small molecules contained in the culture medium (growth factors, serum proteins, nutritional elements ensuring the viability of the cells such as the ions $Ca^{2+}$, $K^+$, $Na^+$, etc.). These pores also make it possible to let pharmacological molecules pass through, such as inhibitors or anti-cancerous molecules, small RNAs (for example, interfering RNAs), hormones (for example, dihydrotestosterone).

The expression, "3D nanostructured" which relates to the porous membrane means the presence of at least one relief structure, that is three-dimensional, on the upper face of said porous membrane, the scale of said structure being around one nanometre.

The expression, "secured" which means the type of connection between said support and said membrane, means that the chemical bonds, as well as hydrophobic and electrostatic interactions are established between said support and said membrane in order to bind said membrane and said support cohesively by a sealed connection.

The term, "base" means the solid part wherein is integrated said unit.

The expression, "forming a whole" used to characterise the arrangement between the base and the unit, means that the base and the unit, together form a part of one single holding, and cannot be separated from one another.

According to a specific embodiment, the invention relates to a microfluidic cell culture chip which contains a central module (104) comprising:
 a central unit (105), which contains
  a support consisting of a non-resorbable membrane (1), comprising an upper face (2) and a lower face (3), perforated by at least one perforation (4),
  a 3D nanostructured porous membrane (5), comprising an upper face (6) and a lower face (7), and comprising at least one protuberance (8), said at least one protuberance comprising an outer face (9) and an inner face (10) and forming a relief structure on the side of the upper face (6) of the 3D nanostructured membrane (5) (FIG. 40),
  said lower face (7) of said 3D nanostructured membrane (5) being positioned secured to said upper face (2) of said support (1),
  and said 3D nanostructured porous membrane (5) and the at least one protuberance (8) consisting of materials suitable for the culture of two distinct cell types;
 a base (106),
said central unit (105) being integrated in said base (106), and forming a whole with said base (106) (FIGS. 39 and 40).

According to a specific embodiment, the invention relates to a microfluidic cell culture chip which contains a central module (104) comprising:
 a central unit (105), which contains
  a support consisting of a non-resorbable membrane (1), comprising an upper face (2) and a lower face (3), perforated by at least one perforation (4),
  a 3D nanostructured porous membrane (5), comprising an upper face (6) and a lower face (7), and comprising at least one protuberance (8), said at least one protuberance comprising an outer face (9) and an inner face (10) and forming a relief structure on the side of the upper face (6) of the 3D nanostructured membrane (5),
  said upper face (6) of said 3D nanostructured membrane (5) being positioned secured to said lower face (3) of said support (1),
  and said 3D nanostructured porous membrane (5) and the at least one protuberance (8) consisting of materials suitable for the culture of two distinct cell types;
said central unit (105) being integrated in said base (106), and forming a whole with said base (106).

According to a specific embodiment, the invention relates to a microfluidic cell culture chip wherein said at least one protuberance (8) of the nanostructured porous membrane of said microfluidic cell culture chip, is in the shape of a hollow dome and has a circular base (13).

The expression, "in the shape of a dome" which relates to the shape of the protuberance means that said protuberance has a rounded structure in the form of an arch with a circular base, forming a convexity on the side of the upper face of said support.

In another embodiment, said protuberance can have a rounded structure in the shape of an arch with an oval base, forming a convexity of the side of the upper face of said support.

The expression, "in the shape of a hollow dome" means that the inner face of said protuberance delimits a free volume as said protuberance corresponds to a reinforcement of said 3D nanostructured membrane on the side of the lower face thereof, said reinforcement thus forming a concavity on the side of the lower face of said membrane, and therefore a free volume.

The expression, "circular base" which relates to the hollow dome, means the free lower surface on which rests the protuberance in the shape of a dome and delimited by the inner face of said protuberance.

According to a specific embodiment, the invention relates to a microfluidic cell culture chip wherein said at least one perforation of the support is characterised by a circular section at the upper face of said support and a circular section at the lower face of said support.

According to a specific embodiment, the invention relates to a microfluidic cell culture chip wherein said at least one perforation (4) of the support (1) has
  a section (11) at the upper face (2) of the support (1) (upper section of the perforation) having an axis (x) passing through the centre of said upper section (11) of the perforation (4) perpendicular to said support (1),
  and a section (12) at the lower face (3) of the support (1) (lower section of the perforation) having an axis (w) passing through the centre of said lower section (12) of the perforation (4) and perpendicular to said support (1),
and wherein said axes (x) and (w) are combined.

According to a specific embodiment, the invention relates to a microfluidic cell culture chip wherein the diameter d2 of the circular section of said perforation at the lower face of the support, is greater than or equal to the diameter d1 of the circular section of said perforation at the upper face of the support.

Figure 2:
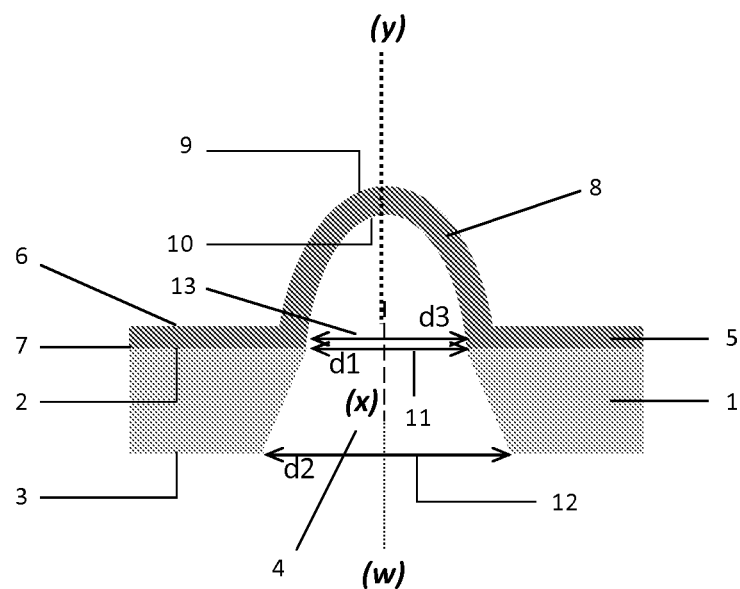

According to a specific embodiment, the invention relates to a microfluidic cell culture chip wherein said at least one perforation (4) of the support (1) has
  a circular-shaped section (11) at the upper face of the support (1) (upper section of the perforation) having a diameter d1 (upper diameter d1 of the perforation) and an axis (x) passing through the centre of said upper section (11) of the perforation (4) and perpendicular to said support (1),
  and a circular-shaped section (12) at the lower face (3) of the support (1) (lower section of the perforation) having a diameter d2 (lower diameter d2 of the perforation) and an axis (w) passing through the centre of said lower section of the perforation and perpendicular to said support (1),
the diameter d1 being of a value greater than or equal to 10 µm at a value less than or equal to 500 µm, preferably of a value of 150 µm, and the diameter d2 being of a value less than or equal to 500 µm, preferably of a value of 150 µm, such that the value of the diameter d2 is greater than or equal to the value of the diameter d1,
and wherein said axes (x) and (w) are combined (FIGS. 1 and 2).

According to a specific embodiment, the invention relates to a microfluidic cell culture chip wherein the diameter d2 of the circular section of said perforation at the lower face of the support, is greater than the diameter d1 of the circular section of said perforation at the upper face of the support.

According to a specific embodiment, the invention relates to a microfluidic cell culture chip wherein the diameter d2 of the circular section of said perforation at the lower face of the support, is greater than the diameter d1 of the circular section of said perforation at the upper face of the support, such that the ratio (value of d1/value of d2) is from a value of 0.3 to a value less than 1.

According to a specific embodiment, the invention relates to a microfluidic cell culture chip wherein the diameter d2 of the circular section of said perforation at the lower face of the support, is greater than the diameter d1 of the circular section of said perforation at the upper face of the support, and said perforation of said support is in the shape of a truncated cone.

According to a specific embodiment, the invention relates to a microfluidic cell culture chip wherein the value of the upper diameter d1 of said at least one perforation (4) is less than the value of the lower diameter d2 of said at least one perforation (4), and said perforation (4) is of a truncated cone shape (FIG. 2).

According to a specific embodiment, the invention relates to a microfluidic cell culture chip wherein the diameter d2 of the circular section of said perforation at the lower face of the support, is equal to the diameter d1 of the circular section of said perforation at the upper face of the support.

According to a specific embodiment, the invention relates to a microfluidic cell culture chip wherein the diameter d2 of the circular section of said perforation at the lower face of the support, is equal to the diameter d1 of the circular section of said perforation at the upper face of the support, and said perforation of said support is of a cylindrical shape.

In this embodiment, the perforation of said support is therefore of a regular shape, i.e. the diameters of all of the sections thereof are of equal lengths, and said sections are of a circular shape.

According to a specific embodiment, the invention relates to a microfluidic cell culture chip wherein the value of the upper diameter d1 of said at least one perforation (4) is equal to the value of the lower diameter d2 of said at least one perforation (4) and said perforation (4) is of a cylindrical shape (FIG. 1).

According to a specific embodiment, the invention relates to a microfluidic cell culture chip wherein said protuberance (8) has a circular base (13) and has a diameter d3 (diameter d3 of the circular base of the protuberance), said diameter d3 of the protuberance (8) being from a value of 10 µm to a value of 500 µm.

According to a specific embodiment, the invention relates to a microfluidic cell culture chip wherein the value of the diameter d3 of said at least one protuberance (8) is equal to the value of the upper diameter d1 of said at least one perforation (4) (FIGS. 1 and 2).

Figure 3:
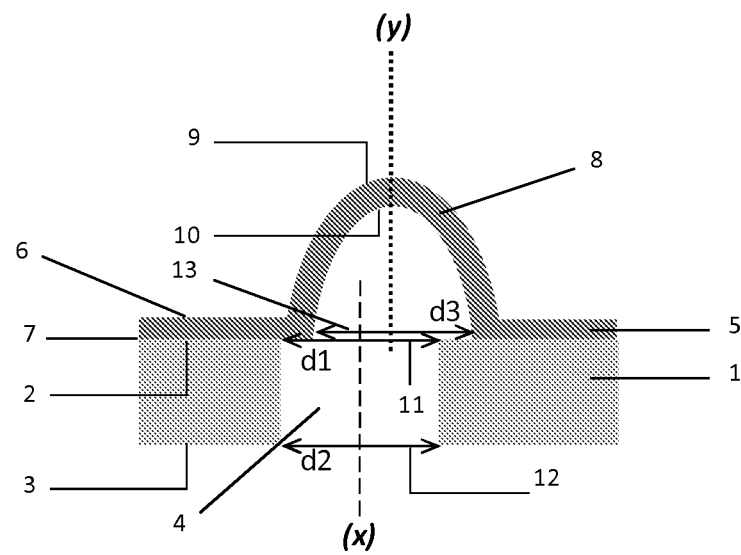

According to a specific embodiment, the invention relates to a microfluidic cell culture chip wherein the value of the diameter d3 of said at least one protuberance (8) is equal to the value of the upper diameter d1 of said at least one perforation and is equal to the value of the lower diameter d2 of said at least one perforation (4) (FIGS. 1 and 3).

Figure 4:
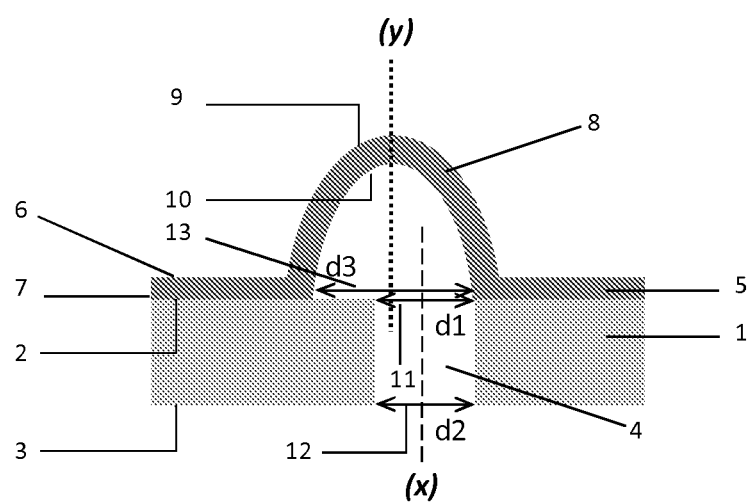
Figure 5:
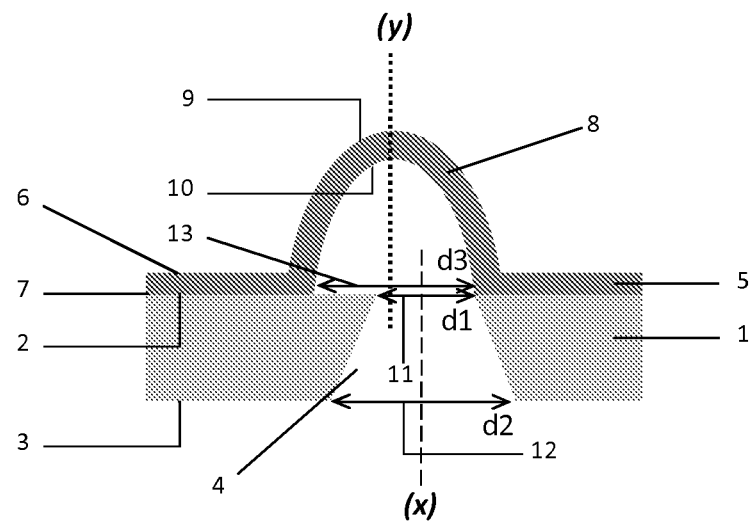
Figure 6:
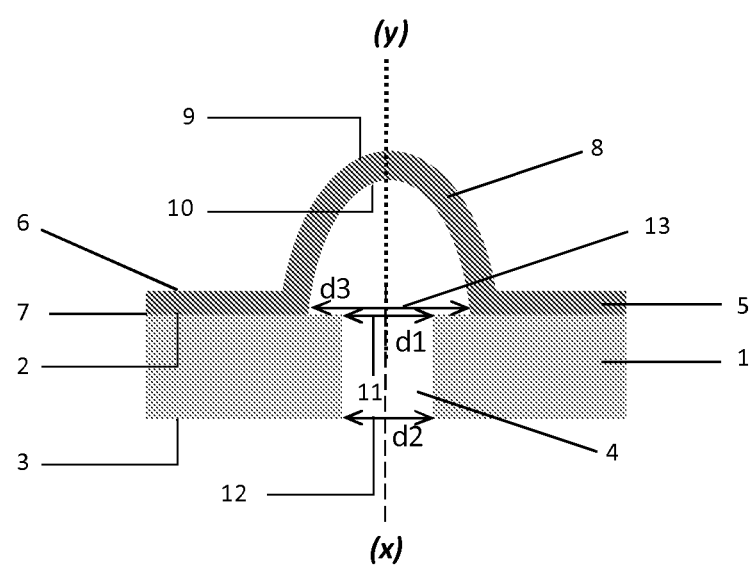

According to a specific embodiment, the invention relates to a microfluidic cell culture chip wherein the value of the diameter d3 of said at least one protuberance (8) is greater than the value of the upper diameter d1 of said at least one perforation (4) (FIGS. 4, 5 and 6).

According to a specific embodiment, the invention relates to a microfluidic cell culture chip wherein the value of the diameter d3 of said at least one protuberance (8) is less than the value of the upper diameter d1 of said at least one perforation (4) (FIGS. 7, 8, 9, 10 and 11).

According to a specific embodiment, the invention relates to a microfluidic cell culture chip wherein said inner face (10) of said at least one protuberance (8) is in whole or in part, facing said at least one perforation (4) of said support (1).

The 3D nanostructured membrane comprising at least one protuberance and the support perforated by at least one perforation are positioned such that the inner face of said protuberance is in whole or in part, facing the circular section of said perforation at the upper face of the support.

Figure 7:
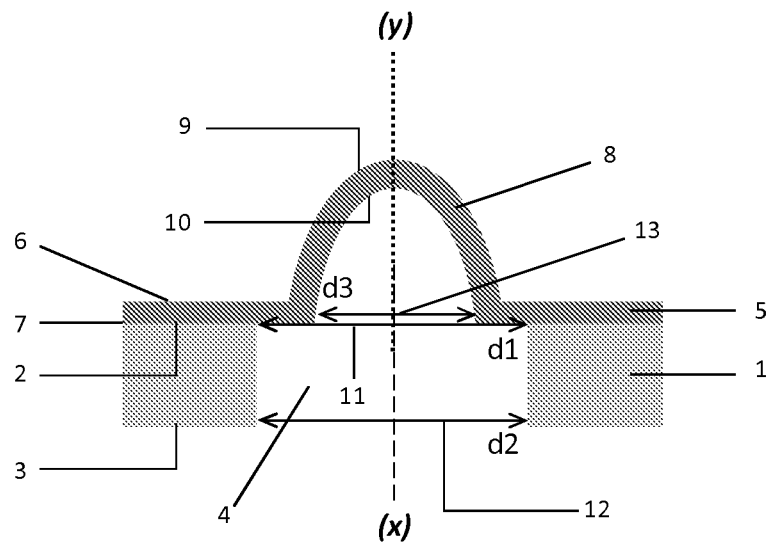
Figure 8:
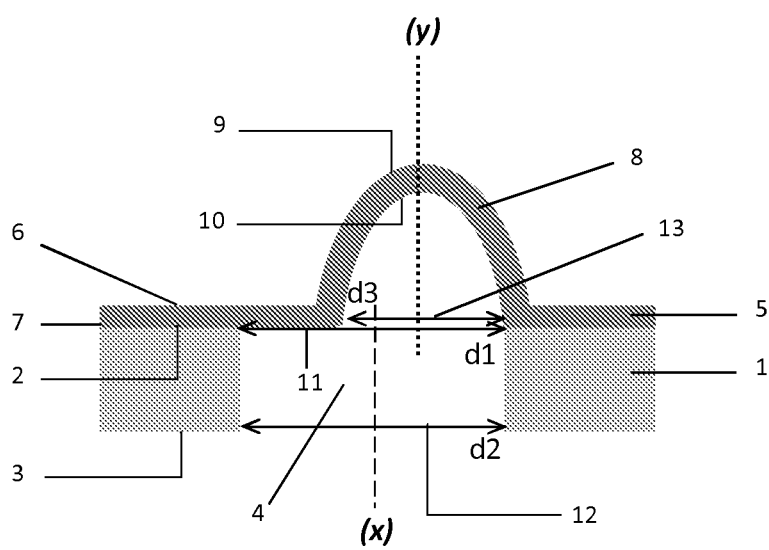
Figure 11:
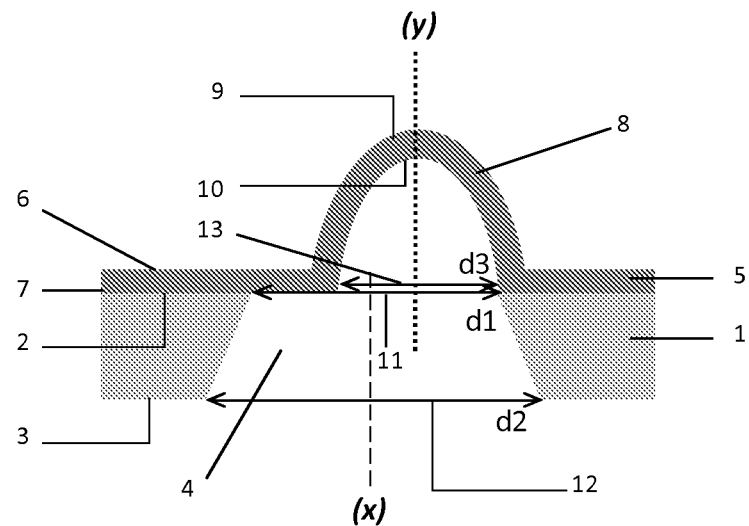

According to a specific embodiment, the invention relates to a microfluidic cell culture chip wherein said inner face (10) of said at least one protuberance (8) is in whole, facing said at least one perforation (4) of said support (1):

when the value of the upper diameter d1 of said at least one perforation (4) is greater than or equal to the value of the diameter d3 of said at least one protuberance (4), and the axis (y), passing through the centre of said circular base (13) and perpendicular to said support (1), and the axis (x), passing through the centre of the upper section (11) of said perforation (4) and perpendicular to said support (1), are combined (FIGS. 1, 2, 7 and 9); or when the value of the upper diameter d1 of said at least one perforation (4) is greater than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value less than or equal to [(value of d1−value of d3)/2] (FIGS. 8 and 11).

The term, "combined" used to characterise the axes (x) and (y) means that the distance between these two axes is equal to zero.

The term, "distinct" used to characterise the axes (x) and (y) means that the distance between these two axes is strictly greater than zero.

Figure 10:
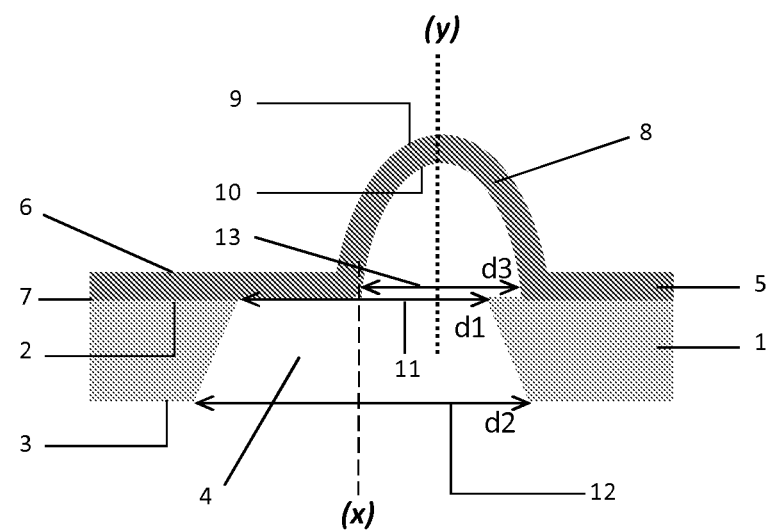

According to a specific embodiment, the invention relates to a microfluidic cell culture chip wherein said inner face (10) of said at least one protuberance (8) is partially facing said at least one perforation (4) of said support (1):

when the value of the upper diameter d1 of said at least one perforation (4) is less than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are combined (FIG. 6); or when the value of the upper diameter d1 of said perforation (4) is equal or less than the value of the diameter d3 of said protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value less than the value of d3 (FIGS. 3, 4 and 5); or when the value of the upper diameter d1 of said perforation (4) is greater than the value of the diameter d3 of said protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value greater than [(value of d1−value of d3)/2] at a value less than [[value of d1+value of d3]/2] (FIG. 10).

Figure 12:
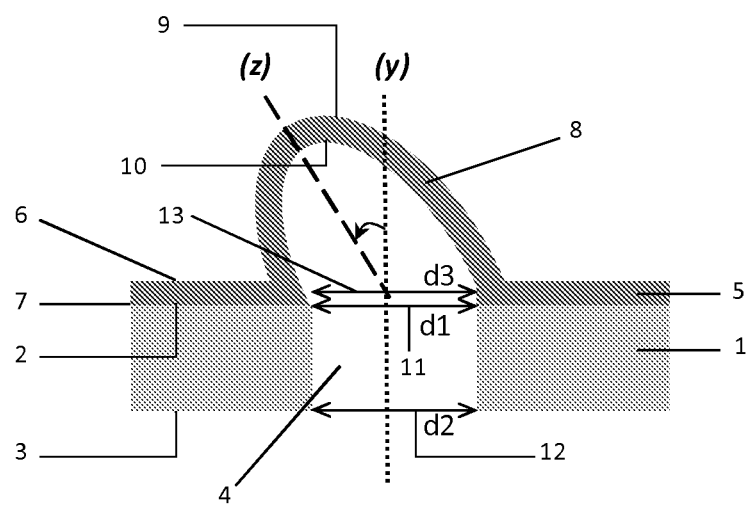

According to a specific embodiment, the invention relates to a microfluidic cell culture chip wherein the protuberance (4) has an oblique deformation, said oblique deformation being defined by the angle α formed between the axis (z) passing through the centre of the circular base (13) of diameter d3, delimited by said protuberance (8) at the upper face (2) of said support (1), and by the top of said protuberance (8), and the axis (y) passing through the centre of said circular base (13) and which is perpendicular to said support (1) (FIG. 12).

According to a specific embodiment, the invention relates to a microfluidic cell culture chip wherein the angle α formed between the axis (y) and the axis (z) is between 0 and 45°.

According to a specific embodiment, the invention relates to a microfluidic cell culture chip wherein the angle α formed between the axis (y) and the axis (z) is between 0 and 60°.

If the angle α formed between the axis (y) and the axis (z) is greater than 45°, the tilt of the protuberance partially blocks the recovery of the secretions. The maximum theoretical value that can take the angle α is 90°, but in this embodiment, the protuberance is completely folded along the upper face of said 3D nanostructure membrane, and the recovery of the secretions is blocked.

According to a specific embodiment, the invention relates to a microfluidic cell culture chip wherein the outer face (9) of said protuberance (8) supports at least one adherent cell on said outer face, and wherein the inner face (10) of said protuberance (8) supports at least one adherent cell on said inner face (10), the at least two cells belonging to two distinct cell types.

The term, "adherent cells" means any type of cells of which the growth requires an adhesion to a support and for which the detachment to said support requires a mechanical or enzymatic treatment (for example, with trypsin).

The term, "distinct cell types" is used to mean cell types of different natures or functions, or coming from different tissues.

According to a specific embodiment, the invention relates to a microfluidic cell culture chip wherein said adherent cell on said outer face is a stromal cell, and said adherent cell on said inner face is an epithelial cell.

According to a specific embodiment, the invention relates to a microfluidic cell culture chip wherein said at least one adherent cell on said outer face (9) is a stromal cell, more specifically a fibroblast, and said at least one adherent cell on said inner face (10) is an epithelial cell.

According to a specific embodiment, the invention relates to a microfluidic cell culture chip wherein said adherent cell on said outer face is an epithelial cell, and said adherent cell on said inner face is a stromal cell.

The epithelial cells can be prostate, bladder or kidney non-tumorigenic commercial cell lines, or commercial primary cultures.

The stromal cells can be fibroblasts (commercial primary cultures or lines), mesenchyme cells (commercial cultures or lines), or other stromal cells such as endothelial cells.

The two cell types cultured on the inner and outer faces of said protuberance, are called "neutral" or healthy cells, i.e. that they are non-tumorigenic.

Figure 13:
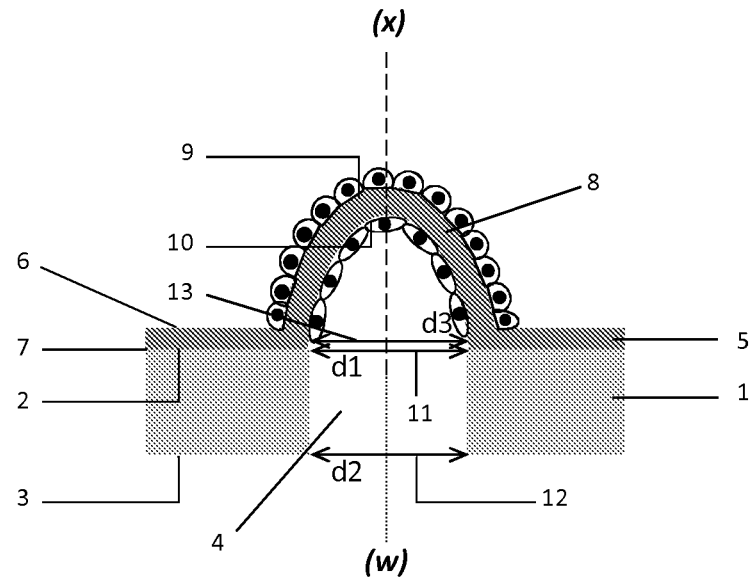

According to a specific embodiment, the invention relates to a microfluidic cell culture chip wherein the outer face (9) of said protuberance (8) supports a first set of adherent cells at the stage of the confluence, and wherein the inner face (10) of said protuberance (8) supports a second set of adherent cells at the stage of the confluence, the cells of the first and of the second set of adherent cells belonging to two distinct cell types (FIG. 13).

Figure 52:
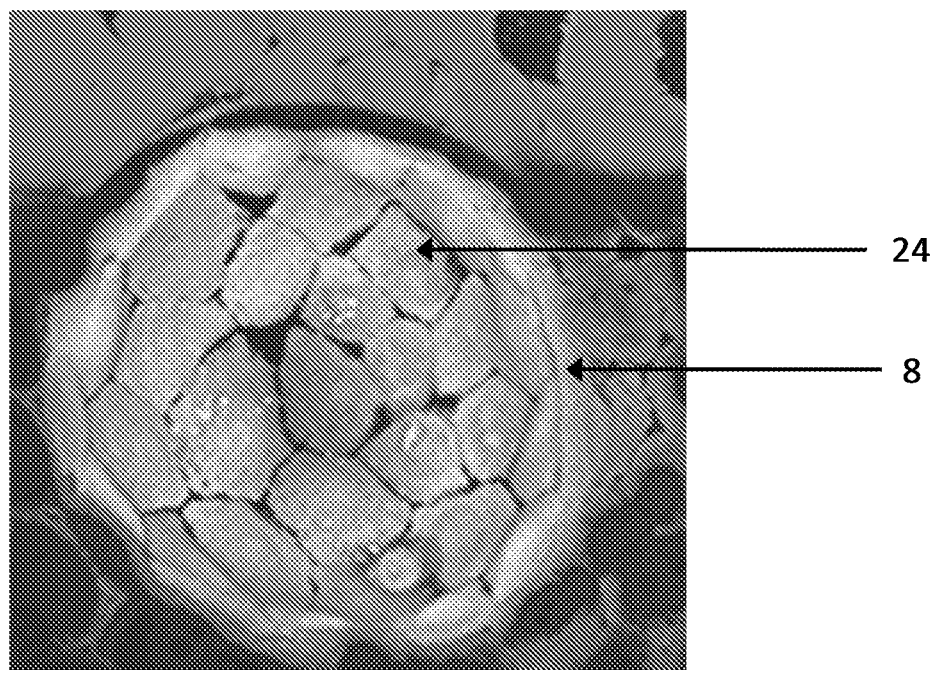

According to a specific embodiment, the invention relates to a microfluidic cell culture chip wherein the outer face (9) of said protuberance (8) supports a first set of adherent cells, advantageously at the stage of the confluence, said first set being a set of stromal cells, more specifically of fibroblasts, and wherein the inner face (10) of said protuberance (8) supports a second set of adherent cells at the stage of the confluence, said second set being a set of epithelial cells (FIG. 52).

According to a specific embodiment, the invention relates to a microfluidic cell culture chip wherein the outer face (9) of said protuberance (8) supports a first set of adherent cells, said first set being a set of stromal cells, more specifically of fibroblasts, and wherein the inner face (10) of said protuberance (8) supports a second set of adherent cells at the stage of the confluence, said second set being a set of epithelial cells.

According to a specific embodiment, the invention relates to a microfluidic cell culture chip wherein the outer face and the inner face of the protuberances, are covered with an extracellular matrix (ECM) preparation (Matrigel®, collagen, fibronectin, hyaluronic acid), before introducing cells on these surfaces, that is before the cell culture. More specifically, said ECM preparation is composed of Matrigel® or a Matrigel®/collagen mixture.

According to a specific embodiment, the invention relates to a microfluidic cell culture chip wherein said 3D nanostructured porous membrane has a thickness of 2 to 300 nm, more specifically of 30 nm.

According to a specific embodiment, the invention relates to a microfluidic cell culture chip wherein said 3D nanostructured porous membrane has a thickness of 2 to 300 nm.

According to a specific embodiment, the invention relates to a microfluidic cell culture chip wherein said 3D nanostructured porous membrane has a thickness of 30 nm.

The protuberance having a section at the circular-shaped base thereof, the surface of this section can be calculated according to the radius.

According to a specific embodiment, the invention relates to a microfluidic cell culture chip wherein said protuberance in the shape of a hollow dome has a height of 1 to 600 µm, more specifically from 1 to 300 µm, more specifically from 50 to 300 µm, more specifically of 50 µm and a surface delimited by the base of the dome of 78.5 µm² to 200000 µm², more specifically from 2000 to 70000 µm², even more specifically of 17500 µm², and even more specifically of 7850 µm².

The term, "height" means the distance between the centre of the top of the protuberance and the centre of the opening of diameter d3.

According to a specific embodiment, the invention relates to a microfluidic cell culture chip wherein said support comprises at least two perforations of identical shape and dimensions, and said 3D nanostructured porous membrane comprises at least two protuberances of identical shape and dimensions, the number of perforations being equal to the number of protuberances.

When said membrane comprises at least two protuberances, the distance must be defined between these at least two protuberances.

Figure 32:
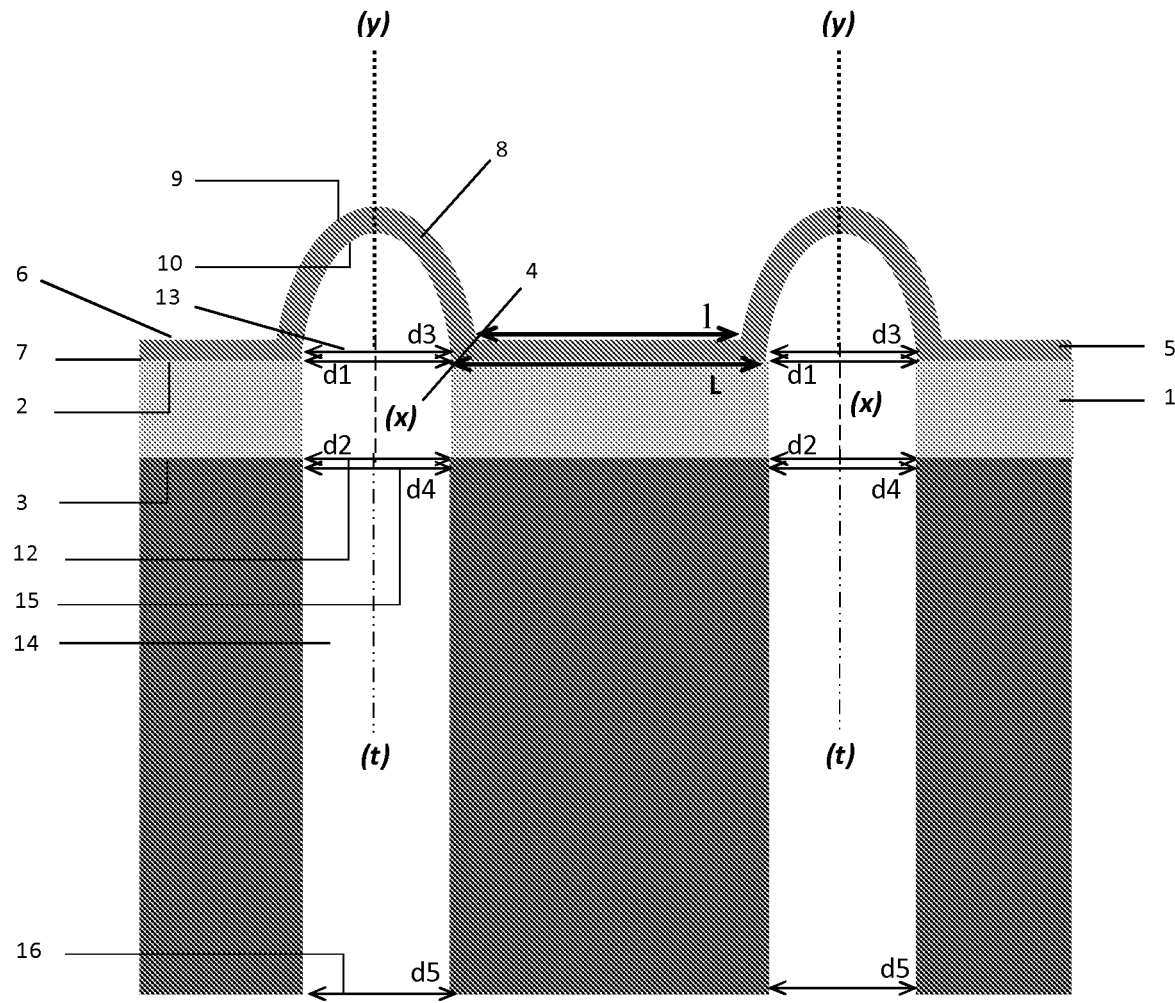

The definition of the expression, "distance between two contiguous protuberances" must be as being the distance between two points, situated respectively over the circumference formed by the intersection of the outer face of said 3D nanostructured membrane of two contiguous protuberances, and forming the shortest distance among all the possible distances between the point couples situated respectively over said circumferences of two contiguous protuberances (FIG. 32).

When said membrane comprises at least two protuberances, these must be separated by a suitable distance.

According to a specific embodiment, the invention relates to a microfluidic cell culture chip wherein the distance between two contiguous protuberances is of a value 1, said value 1 being from 10 to 100 µm.

According to a specific embodiment, the invention relates to a microfluidic cell culture chip wherein the distance between two contiguous protuberances is of a value 1, said value 1 being from 10 to 100 µm, more specifically from 50 to 100 µm.

According to a specific embodiment, the invention relates to a microfluidic cell culture chip wherein the distance between two contiguous protuberances is of a value 1, said value 1 being from 50 to 100 µm.

In each of the paragraphs below, the expression, "distance between two contiguous protuberances" can be replaced by the definition given above.

According to a specific embodiment, the invention relates a microfluidic cell culture chip wherein said support comprises at least two perforations, and said nanostructured porous membrane comprises at least two protuberances such as the ratio d1/d2 varies from 1 to d1/(d1+l), 1 being the value of the distance between two contiguous protuberances, where the diameter d1 is of a value greater than or equal to 10 µm at a value less than or equal to 500 µm, and the diameter d2 is of a value greater than or equal to 10 µm and less than or equal to 500 µm.

Thus, the lower diameter d2 of said perforation at the lower face of the support, is always greater than or equal to the upper diameter d1 of said perforation at the upper face of the support.

According to a specific embodiment, the invention relates to a microfluidic cell culture chip wherein said 3D nanostructured porous membrane comprises 1 to 100 protuberances for a surface of the central unit of 1 cm².

According to a specific embodiment, the invention relates to a microfluidic cell culture chip wherein said 3D nanostructured membrane comprises a maximum number of protuberances for a surface of the central unit of 1 cm², equal to the formula $$\frac{\pi(d3/2)^2}{(l+d3)-\pi(d3/2)^2}$$

where l is the distance between two contiguous protuberances, said value l being from 10 to 100 µm, more specifically from 50 to 100 µm, and where d3 is the diameter of said protuberance.

The 3D nanostructured porous membrane is composed of a number of successive layers of polyelectrolytes from 1 to 150, being understood that the successiveness of the layers is applied from at least two layers.

The number of layers makes it possible to make the mechanical strength of the protuberance vary. Indeed, the greater the number of layers will be increased and the greater the mechanical resistance of the protuberance will be increased, such that they can conserve the form thereof, while supporting the cell culture on these outer and inner faces and by resisting the flow (for example of culture medium) on either side of it.

According to a specific embodiment, the invention relates to a microfluidic cell culture chip wherein the number of successive layers of polyelectrolytes is from 1 to 150, in particular of 15.

The use of polyelectrolyte to constitute the 3D nanostructured porous membrane provides a biocompatible and functional substitute to mimic the basal lamina on which the adherent cells come to be attached in the tissues.

The 3D nanostructured porous membrane can consist of a layer of a polyelectrolyte.

According to a specific embodiment, the invention relates to a microfluidic cell culture chip wherein the 3D nanostructured porous membrane consists of a layer of a polyelectrolyte selected from among poly(sodium 4-styrenesulphonate) (PSS), poly(ethyleneimine), poly(diallyldimethylammonium chloride), poly(acrylamide-co-diallyldimethylammonium chloride), diallyldimethylammonium chloride, poly(allylamine hydrochloride) (PAH), polyanetholesulfonic acid, polyacrylic acid, poly(styrene-alt-maleic acid), polyvinyl sulphate, polyvinylsulfonic acid, poly(2-acrylamido-2-methyl-1-propanesulfonic acid), poly(2-acrylamido-2-methyl-1-propanesulfonic-co-acrylonitrile) acid, poly(4-styrenesulfonic acid), poly(4-styrenesulfonic acid-co-maleic acid), hydrated 4-styrenesulfonic sodium salt.

The 3D nanostructured porous membrane, can consist of at least two successive layers of a polyelectrolyte.

When said membrane comprises at least two layers, the construction of this membrane, layer by layer, is essential.

The at least one protuberance being an integral part of said 3D nanostructured porous membrane, the composition of said 3D nanostructured porous membrane, will be identical to the composition of said at least one protuberance.

According to a specific embodiment, the invention relates to a microfluidic cell culture chip wherein the 3D nanostructured porous membrane consists of successive layers of a polyelectrolyte selected from among poly(sodium 4-styrenesulphonate) (PSS), poly(ethyleneimine), poly(diallyldimethylammonium chloride), poly(acrylamide-co-diallyldimethylammonium chloride), diallyldimethylammonium chloride, poly(allylamine hydrochloride) (PAH), polyanetholesulfonic acid, polyacrylic acid, poly(styrene-alt-maleic acid), polyvinyl sulphate, polyvinylsulfonic acid, poly(2-acrylamido-2-methyl-1-propanesulfonic acid), poly(2-acrylamido-2-methyl-1-propanesulfonic-co-acrylonitrile) acid, poly(4-styrenesulfonic acid), poly(4-styrenesulfonic acid-co-maleic acid), hydrated 4-styrenesulfonic sodium salt.

When said membrane comprises at least two successive layers, said layers can correspond to at least two polyelectrolytes of a different nature: at least one negatively charged polyelectrolyte and at least one positively charge polyelectrolyte.

In this case, the construction, layer by layer, of this membrane must be done such that a positively charge polyelectrolyte layer alternates with a negatively charged polyelectrolyte layer.

The membrane is thus highly cohesive because of the electrostatic interactions between the positively charged polyelectrolyte layers and the negatively charged polyelectrolyte layers. This makes it possible to obtain a membrane having a Young's modulus and being of around one kilopascal.

It must be noted, that the lower layer and the upper layer of the porous membrane, can consist, independently of one another, any one of the polyelectrolytes.

However, the charge of the polyelectrolyte consisting of the last layer, and therefore consisting of the upper face of said membrane, has an impact on the hydrophobicity of the membrane. Thus, when the last layer consists of a negatively charged polyelectrolyte, the upper face of the membrane is of a relatively hydrophilic nature, compared with a membrane of which the upper face is positively charged. Conversely, when the last layer consists of a positively charged polyelectrolyte, the upper face of the membrane is of a relatively hydrophobic nature, compared with a membrane of which the upper face is negatively charged.

The roughness of the upper face of the membrane is managed by the groups carried by the polyelectrolyte consisting of the last layer of the membrane, that is the layer consisting of the upper face of said membrane. For example, it is a PSS layer, this polyelectrolyte has a pending benzene ring attached and a bound sulphate group, which thus provide a surface, rougher than a PAH layer, electrolyte which does not have any benzene ring attached.

The roughness of the 3D nanostructured porous membrane is around one nanometre.

According to a specific embodiment, the invention relates to a microfluidic cell culture chip wherein the number of successive layers from 1 to 150, in particular of 15, of a positively charged polyelectrolyte and a negatively charged polyelectrolyte, said negatively charged polyelectrolyte layer and said positively charged polyelectrolyte layer alternating with one another.

According to a specific embodiment, the invention relates to a microfluidic cell culture chip wherein the 3D nanostructured porous membrane consists of successive layers of at least two polyelectrolytes, of which at least one polyelectrolyte is positively charged and at least one polyelectrolyte is negatively charged, said positively charged polyelectrolyte being selected from among poly(sodium 4-styrenesulphonate), poly(ethyleneimine), poly(diallyldimethylammonium chloride), poly(acrylamide-co-diallyldimethylammonium chloride), diallyldimethylammonium chloride, and said negatively charged polyelectrolyte being selected from among poly(allyamine hydrochloride), polyanetholesulfonic acid, polyacrylic acid, poly(styrene-alt-maleic acid), polyvinyl sulphate, polyvinylsulfonic acid, poly(2-acrylamido-2-methyl-1-propanesulfonic), poly(2-acrylamido-2-methyl-1-propanesulfonic acid-co-acrylonitrile), poly(4-styrenesulfonic acid), poly(4-styrenesulfonic acid-co-maleic acid), hydrated 4-styrenesulfonic sodium salt, said negatively charged polyelectrolyte layer and said positively charge polyelectrolyte layer alternating with one another.

According to a specific embodiment, the invention relates to a microfluidic cell culture chip wherein the 3D nanostructured porous membrane consists of successive layers of a positively charged polyelectrolyte and of a negatively charged polyelectrolyte, said positive charged polyelectrolyte being poly(sodium 4-styrenesulphonate) (PSS) and said negatively charged polyelectrolyte being poly(allylamine hydrochloride) (PAH), said negatively charged polyelectrolyte layer and said positively charged polyelectrolyte alternating with one another.

According to a specific embodiment, the invention relates to a microfluidic cell culture chip wherein the number of successive layers of poly(sodium 4-styrenesulphonate) (PSS) and/or of poly(allylamine hydrochloride) (PAH), is from 1 to 150, in particular of 15.

According to a specific embodiment, the invention relates to a microfluidic cell culture chip wherein each polyelectrolyte layer has a thickness of 2 to 300 nm, more specifically of around 2 nm.

According to a specific embodiment, the invention relates to a microfluidic cell culture chip wherein the number of successive layers is 15, of a positively charged polyelectrolyte and a negatively charged polyelectrolyte, said negatively charged polyelectrolyte layer and said positively charged polyelectrolyte layer alternating with one another, each layer having a thickness of 2 nm.

According to a specific embodiment, the invention relates to a microfluidic cell culture chip wherein the value of the thickness of all of the successive layers of polyelectrolytes is comprised of the value of the thickness of a layer to a value less than half of the diameter d3 of said protuberance.

According to a specific embodiment, the invention relates to a microfluidic cell culture chip according to RX wherein the 3D nanostructured porous membrane (5) consists of at least one layer of a polyelectrolyte selected from among poly(sodium 4-styrenesulphonate) (PSS), poly(ethyleneimine), poly(diallyldimethylammonium chloride), poly(acrylamide-co-diallyldimethylammonium chloride), diallyldimethylammonium chloride, poly(allylamine hydrochloride) (PAH), polyanetholesulfonic acid, polyacrylic acid, poly(styrene-alt-maleic acid), polyvinyl sulphate, polyvinylsulfonic acid, poly(2-acrylamido-2-methyl-1-propanesulfonic acid), poly(2-acrylamido-2-methyl-1-propanesulfonic acid-co-acrylonitrile), poly(4-styrenesulfonic acid), poly(4-styrenesulfonic acid-co-maleic acid), hydrated 4-styrenesulfonic sodium salt,
- and wherein when said 3D nanostructured porous membrane (5) consists of at least two successive layers, a layer consisting of a positively charged polyelectrolyte alternating with a layer consisting of a negatively charged polyelectrolyte,
- said 3D nanostructured porous membrane (5) consisting, in particular, of 1 to 150 successive layers of polyelectrolyte,
- and more specifically, said 3D nanostructured porous membrane (5) consisting of 15 successive layers of poly(sodium 4-styrenesulphonate) (PSS) and/or poly(allylamine hydrochloride) (PAH), alternating with one another.

The 3D nanostructured porous membrane is therefore composed of successive layers of polyelectrolytes and thus comprises, as variable parameters:
- the number of layers,
- the thickness of each of the layers,
- the charge of the polyelectrolyte(s) used.

By making the number of layers vary, the roughness, the thickness and the rigidity of said membrane, and therefore said protuberance, can be modified.

By making the number of layers or type of charge of polyelectrolytes used vary, the hydrophobicity of said membrane and of said protuberance can also be modified.

According to a specific embodiment, the invention relates to a microfluidic cell culture chip wherein said support has a thickness of 2 µm to 1000 µm, more specifically of 20 µm.

According to a specific embodiment, the invention relates to a microfluidic cell culture chip wherein said perforation has a surface delimited by said non-resorbable membrane of 78.5 µm$^2$ to 200000 µm$^2$, more specifically of 2000 to 70000 µm$^2$, even more specifically of 17500 µm$^2$, and even more specifically of 7850 µm$^2$.

The support comprises at least one perforation. When said support comprises at least two perforation, the distance between these at least two perforations must be defined.

The "distance between two contiguous perforations" must be understood as being the distance between two points situated respectively over the circumference of each of the upper circular sections of said contiguous perforations and forming the shortest distance, among all the possible distances between the point couples situated respectively over the circumference of each of the upper circular sections of said contiguous perforations.

When said support comprises at least two perforations, these must be separated by a suitable distance.

According to a specific embodiment, the invention relates to a microfluidic cell culture chip wherein said distance between two contiguous perforations is of a value L, said value L being from 10 to 100 µm, more specifically from 50 to 100 µm (FIG. 32).

According to a specific embodiment, the invention relates to a microfluidic cell culture chip wherein said support comprises 1 to 100 perforations for a surface of the central unit of 1 cm$^2$.

According to a specific embodiment, the invention relates to a microfluidic cell culture chip wherein the support is composed of bioprinted plastic, polycarbonate, tissue culture plastic, glass or SU-8 resin.

SU-8 resin is a novolac epoxide-based negative photosensitive polymeric resin having an average epoxide group functionality of around 8. SU-8 resin is well known to a person skilled in the art and commonly used in producing the microsystem. The term, "negative" means that the parts exposed to UV become cross-linked, while the remainder of the film remains soluble and can be removed by washing.

Bioprinted plastics correspond to the plastics known to a person skilled in the art, which are suitable for and compatible with 3D printing equipment (extrusion, temperature limitations).

Tissue culture plastics correspond to the plastics, consisting of mould boxes, which comprise a base treatment (treatment carried out by electrical or plasma discharge to make the hydrophilic surface, i.e. with a clear negative charge) and make it possible for the attachment and the growth of eukaryotic adherent cells (difference from plastic culture boxes, not treated for the bacteriology).

According to a specific embodiment, the invention relates to a microfluidic cell culture chip wherein the support is composed of bioprinted plastic, polycarbonate, tissue culture plastic, glass or SU-8 resin, and said support is transparent.

Lower Module

Figure 41:
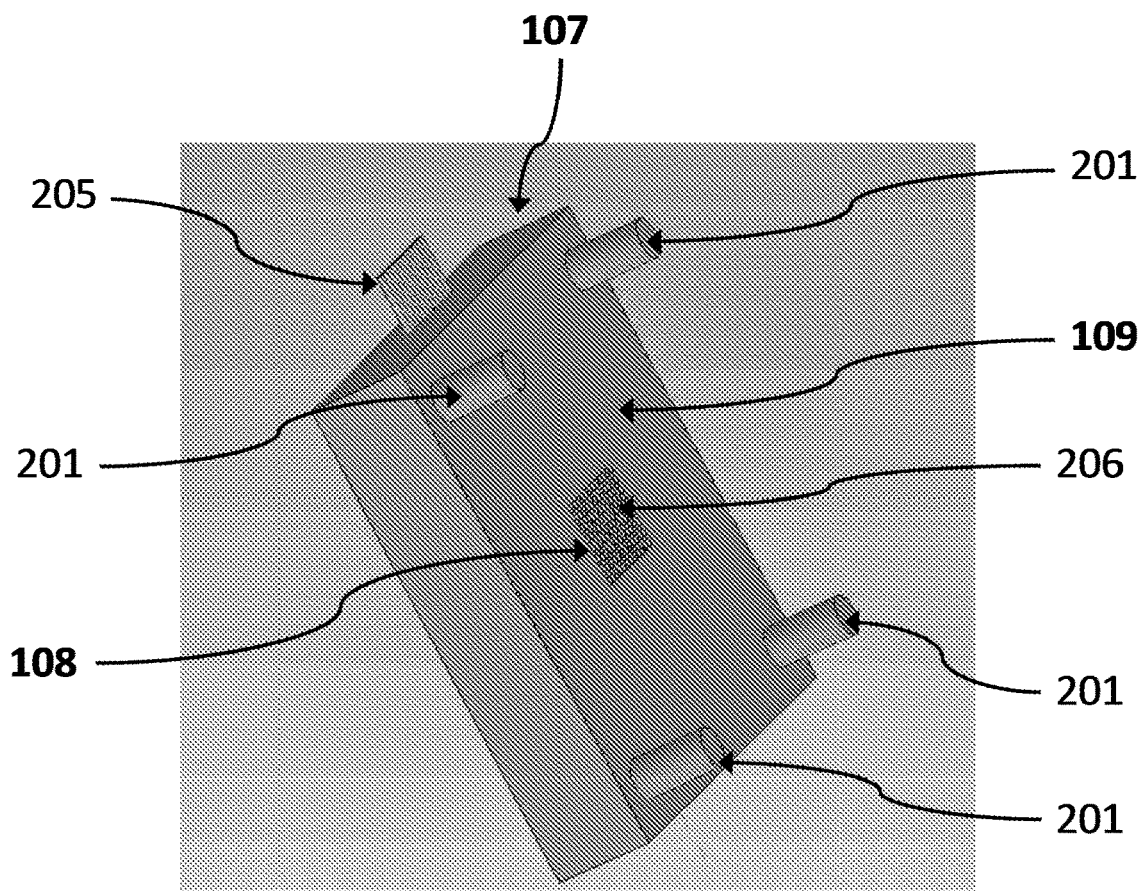
Figure 45:
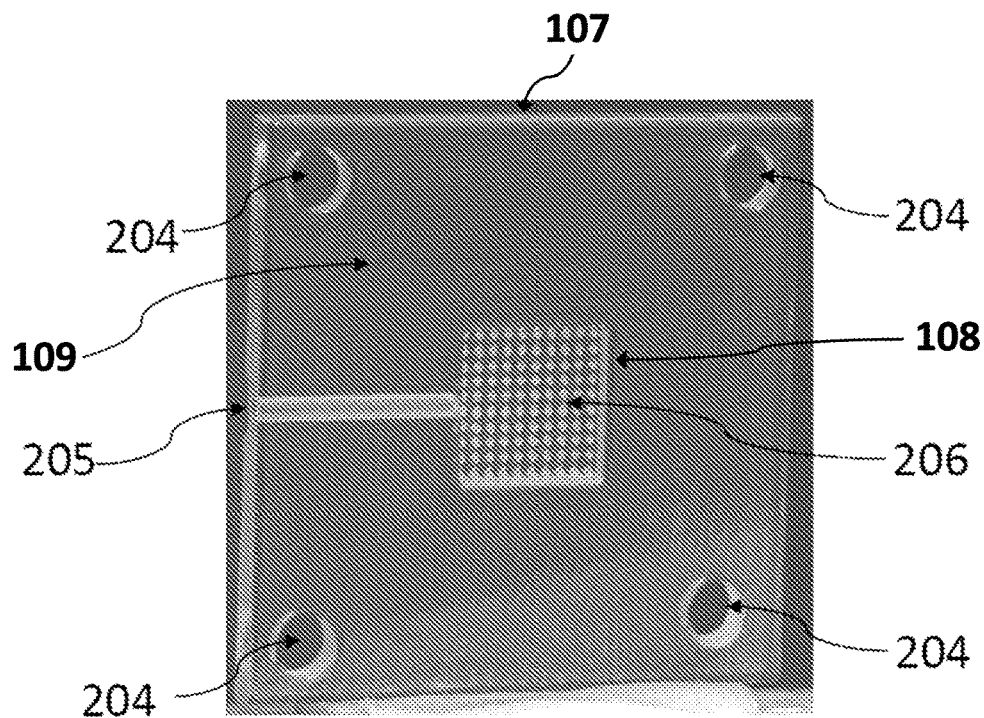

According to a specific embodiment, the invention relates to a microfluidic cell culture chip which contains a solid lower module (107), comprising
  a lower unit (108)
    which contains an upper face, a lower face and at least one side face, and comprising at least one tubular-shaped duct (14) comprising an upper orifice (15) and a lower orifice (16),
  a base (109),
said lower unit (108) being integrated in said base (109), and forming a whole with said base (109),
and said upper face of said lower unit comprising said upper orifices (15) of at least one duct, and said lower orifice (16)

leading, itself or by intermediate means (17), to the outside of said base (109) (FIGS. 41 and 45).

The upper orifice of at least one duct is situated within the lower unit, the at least one duct extends through the lower unit, then through the base of the lower module, said unit and said base forming a part of one single holding, such that the lower orifice of at least one duct leads to the outside of said base.

The lower orifice of at least one duct, either itself leads to the outside of said base, or leads into an intermediate means such as a reservoir, which itself leads to the outside of said base.

According to a specific embodiment, the invention relates to a microfluidic cell culture chip wherein said lower module (107) and said central module (104) are assembled such that the upper orifice (15) of the at least one duct (14), of said upper face of said lower unit (108), opens over at least one of said perforations (4) of said support (1) of said central unit (105), and the lower orifice (16) of the at least one duct (14), leads to the outside of the chip, said upper face of said lower unit (108) and said lower face of said support (3) of said central unit (105) having an identical shape and an identical surface to one another.

The expression, "outside of the chip" must be interpreted as "outside of the base", and vice versa.

When the lower module is assembled to the central module, the upper orifice (15) of the at least one duct (14), of said upper face of said lower unit (108), opens over at least one of said perforations (4) of said support (1). This at least one duct makes it possible to recover the secretions of the cultured cells on the inner face of the at least one protuberance.

This at least one duct also makes it possible to introduce the culture medium and possibly the cells which are cultured on the inner face of said protuberance.

According to a specific embodiment, the invention relates to a microfluidic cell culture chip wherein said lower module (107) and said central module (104) are assembled such that the upper orifice (15) of the at least one duct (14), of said upper face of said lower unit (108), opens over at least one of said perforations (4) of said support (1) of said central unit (105), and the lower orifice (16) of the at least one duct (14), leads to the outside of the chip, via an intermediate means consisting of a reservoir (17) capable of recovering liquids and making it possible for a conveyance to the outside of the chip via an outlet duct (18) leading to the outside of the base (109) of said lower module (107), said upper face of said lower unit (108) and said lower face of said support of said central unit (105) having an identical shape and an identical surface to one another.

According to a specific embodiment, the invention relates to a microfluidic cell culture chip, wherein said lower orifice (16) of the at least one duct (14), leads to the outside of the chip on a device making it possible to analyse compounds in a solution.

This analysis device can consist of any analytical device known to a person skilled in the art, such as a mass spectrometer, an RMN device, a chromatographic device (in liquid or gaseous phase), a device based on immunological interactions (ELISA, immunoprecipitation), a PCT or RT-PCR device.

Indeed, the secretions of the cells are composed from both proteins and peptides, but also from DNA and RNA. Thus, the analysis device(s) selected must make it possible to analyse all of these molecules.

According to a specific embodiment, the invention relates to a microfluidic cell culture chip, wherein said lower orifice (16) of the at least one duct (14), leads to the outside of the chip on a device, making it possible to analyse compounds in a solution, said device being a mass spectrometer.

The microfluidic chip according to the invention can be coupled directly with a chip integrating a mass spectrometer in order to carry out a real time and continuous analysis of the secretions.

According to a specific embodiment, the invention relates to a microfluidic cell culture chip wherein said lower unit (108) and said central unit (105) are assembled by the attachment elements (204) situated respectively on each of the bases of the lower module (109) and of the central module (106), so as to assemble, in a sealed manner, said upper face of said lower unit (108) and said lower face of said support (3) of said central unit (105).

According to a specific embodiment, the invention relates to a microfluidic cell culture chip, wherein the value of the diameter d4 of said upper orifice (15) of said duct (14) is greater than the value of the diameter d5 of said lower orifice (16) of said duct (14).

According to a specific embodiment, the invention relates to a microfluidic cell culture chip, wherein the value of the diameter d4 of said upper orifice (15) of said duct (14) is equal to the value of the diameter d5 of said lower orifice (16) of said duct (14), said at least one duct being cylindrically-shaped.

According to a specific embodiment, the invention relates to a microfluidic cell culture chip, wherein said upper orifice (15) of said at least one duct (14) has a diameter d4 and an axis (t) passing through the centre of said upper orifice (15) and perpendicular to said support (1), such as the value of the diameter d4 is greater than or equal to the value of the lower diameter d2 of said at least one perforation (4).

According to a specific embodiment, the invention relates to a microfluidic cell culture chip, wherein said upper orifice (15) of said at least one duct (14) leads to one single perforation (4) of said support (1).

Figure 15:
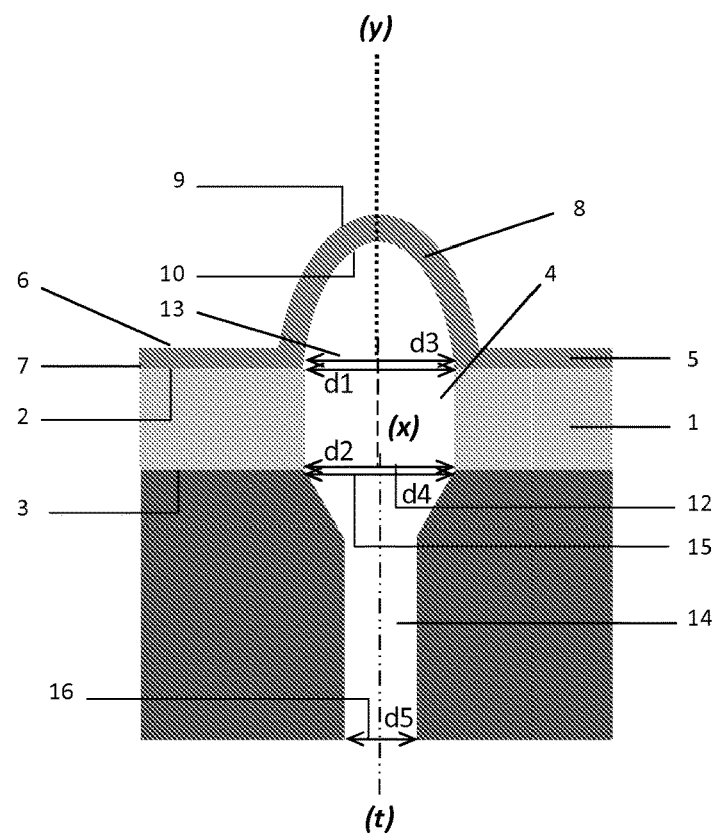
Figure 16:
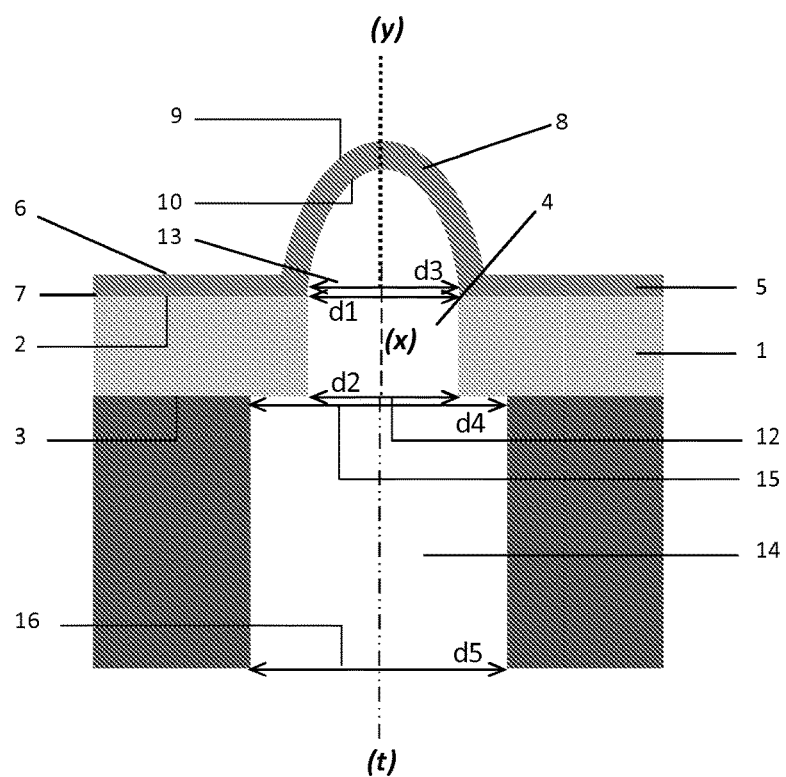
Figure 17:
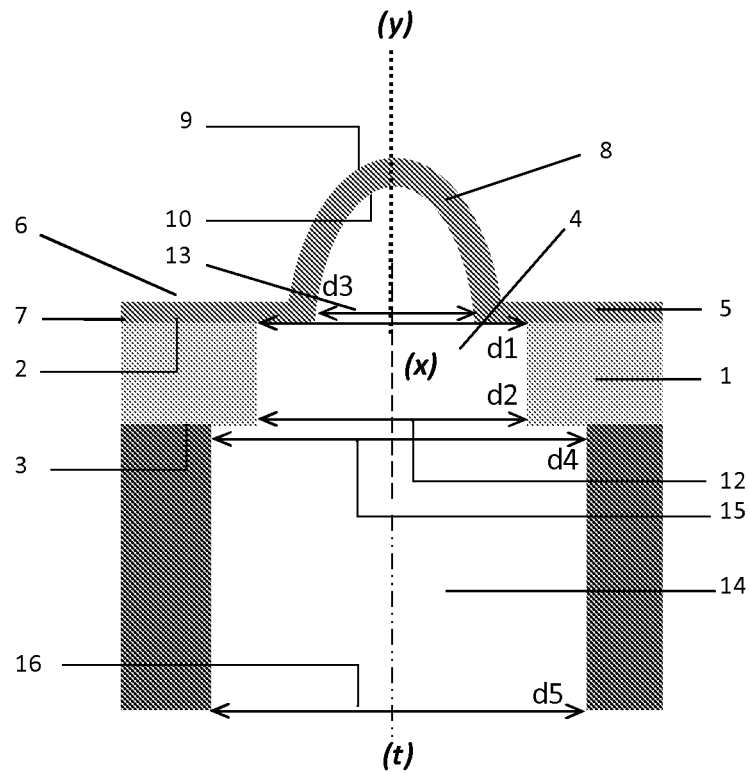
Figure 18:
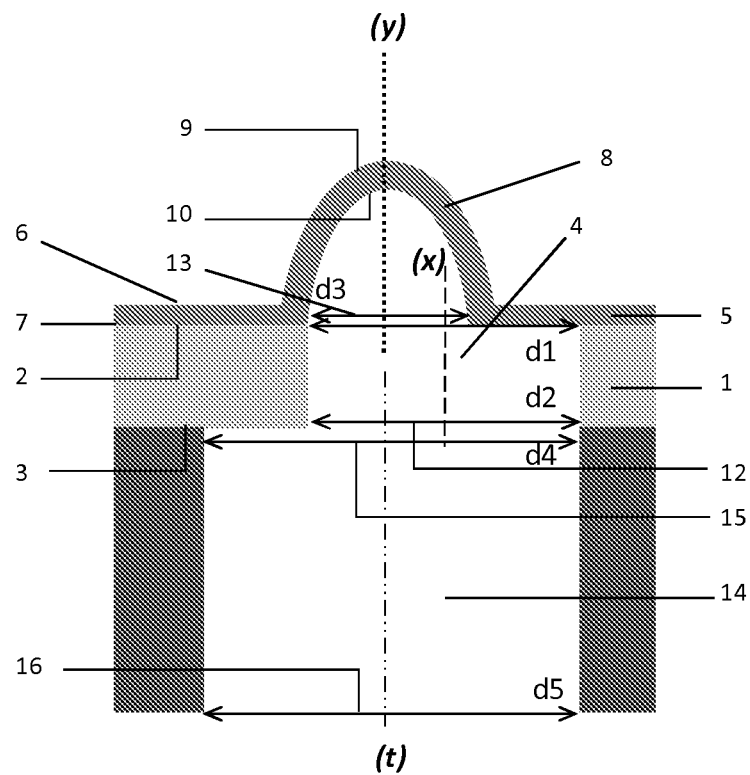

According to a specific embodiment, the invention relates to a microfluidic cell culture chip, wherein said at least one perforation (4) of said support (1) and in whole, facing said upper orifice (15) of said at least one duct (14):

when the value of the lower diameter d2 of said perforation (4) is equal to the value of the diameter d4 of said upper orifice (15) of said duct (14), and the axis (x), passing through the centre of said upper section (11) of the perforation (4) and perpendicular to said support (1), and the axis (t), passing through the centre of said upper orifice (15) of said duct (14) and perpendicular to said support (1), are combined (FIGS. 14 and 15), or when the value of the lower diameter d2 of said perforation (4) is less than the value of the diameter d4 of said upper orifice (15) of said duct (14), and the axis (x), passing through the centre of said upper section (11) of the perforation (4) and perpendicular to said support (1), and the axis (t), passing through the centre of said upper orifice (15) of said duct (14) and perpendicular to said support (1), are combined, or distinct from one another by a distance of a value, less than or equal to [(value of d4−value of d2)/2](FIGS. 16, 17 and 18).

According to a specific embodiment, the invention relates to a microfluidic cell culture chip, wherein said at least one perforation (4) of said support (1) is partially facing said upper orifice (15) of said at least one duct (14):

when the value of the lower diameter d2 of said perforation (4) is equal to the value of the diameter d4 of said upper orifice (15) of said duct (14), the axis (x) passing through the centre of said upper section (11) of the perforation (4) and perpendicular to said support (1), and the axis (t), passing through the centre of said upper orifice (15) of said duct (14) and perpendicular to said support (1), are distinct from one another by a distance of a value, less than or equal to [value of d4/2] (FIGS. 19, 21, 22, 24, 29 and 30), or when the value of the lower diameter d2 of said perforation (4) is less than the value of the diameter d4 of said upper orifice (15) of said duct (14), and the axis (x) passing through the centre of said upper section (11) of the perforation (4) and perpendicular to said support (1), and the axis (t), passing through the centre of said upper orifice (15) of said duct (14) and perpendicular to said support (1), are distinct from one another by a distance of a value, less than or equal to [value of d4/2] (FIGS. 20, 23, 25, 26, 27 and 28).

According to a specific embodiment, the invention relates to a microfluidic cell culture chip, wherein said lower module (107) comprises at least two ducts (14).

According to a specific embodiment, the invention relates to a microfluidic cell culture chip, wherein each of the upper orifices (15) of the at least two ducts (14) leads to a perforation (4) and the at least two lower orifices (16) of the at least two ducts (14) lead to the outside of the chip, respectively to at least two distinct sites (FIG. 32).

Figure 31:
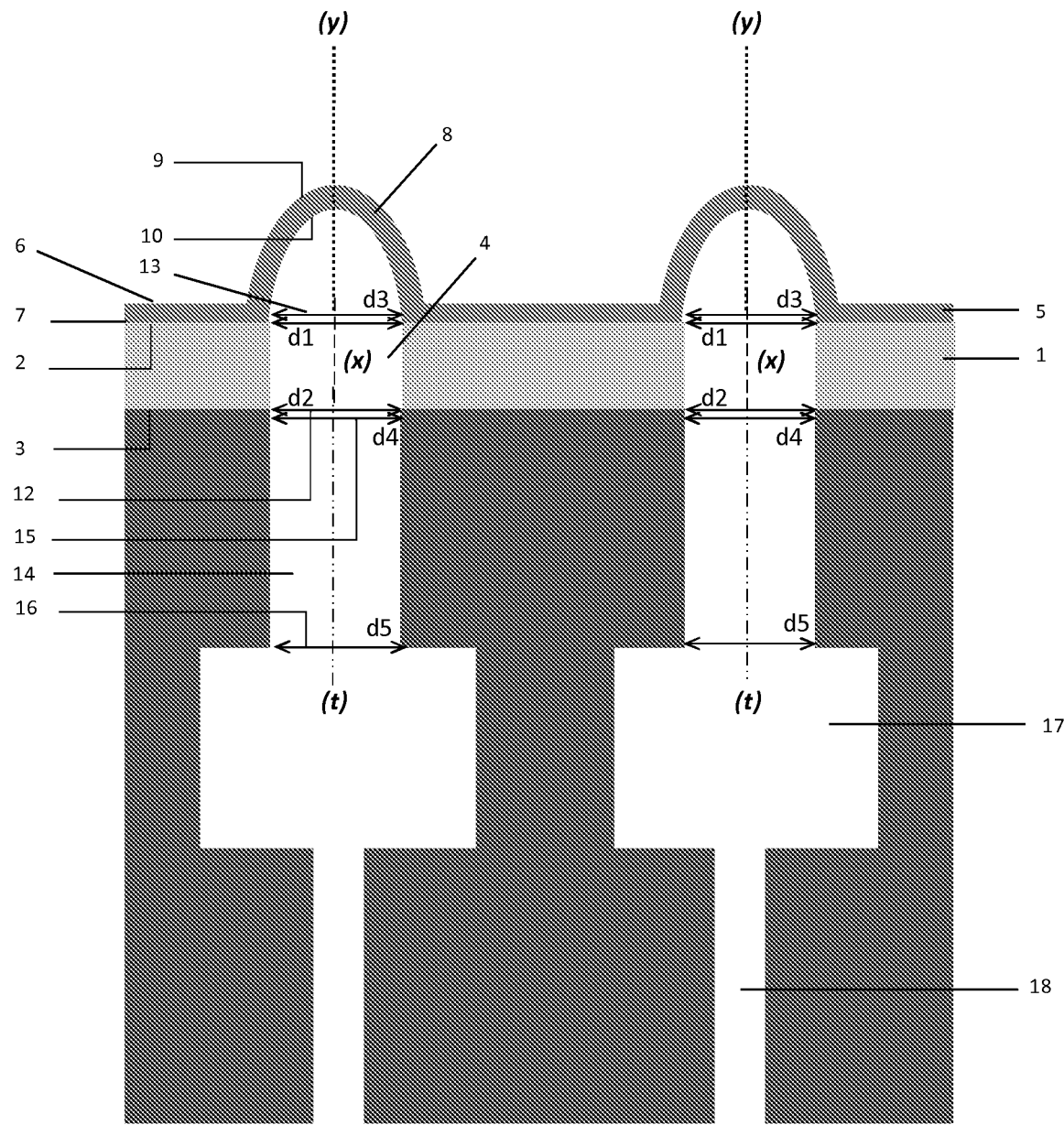

According to a specific embodiment, the invention relates to a microfluidic cell culture chip, wherein each of the upper orifices (15) of the at least two ducts (14) leads to a perforation (4) and the at least two lower orifices (16) of the at least two ducts (14) lead respectively to an intermediate means consisting of a reservoir (17) capable of recovering liquids and making it possible for a conveyance to the outside of the chip via an outlet duct (18) leading to the outside of the base (109) of said lower module (107) (FIG. 31).

Figure 34:
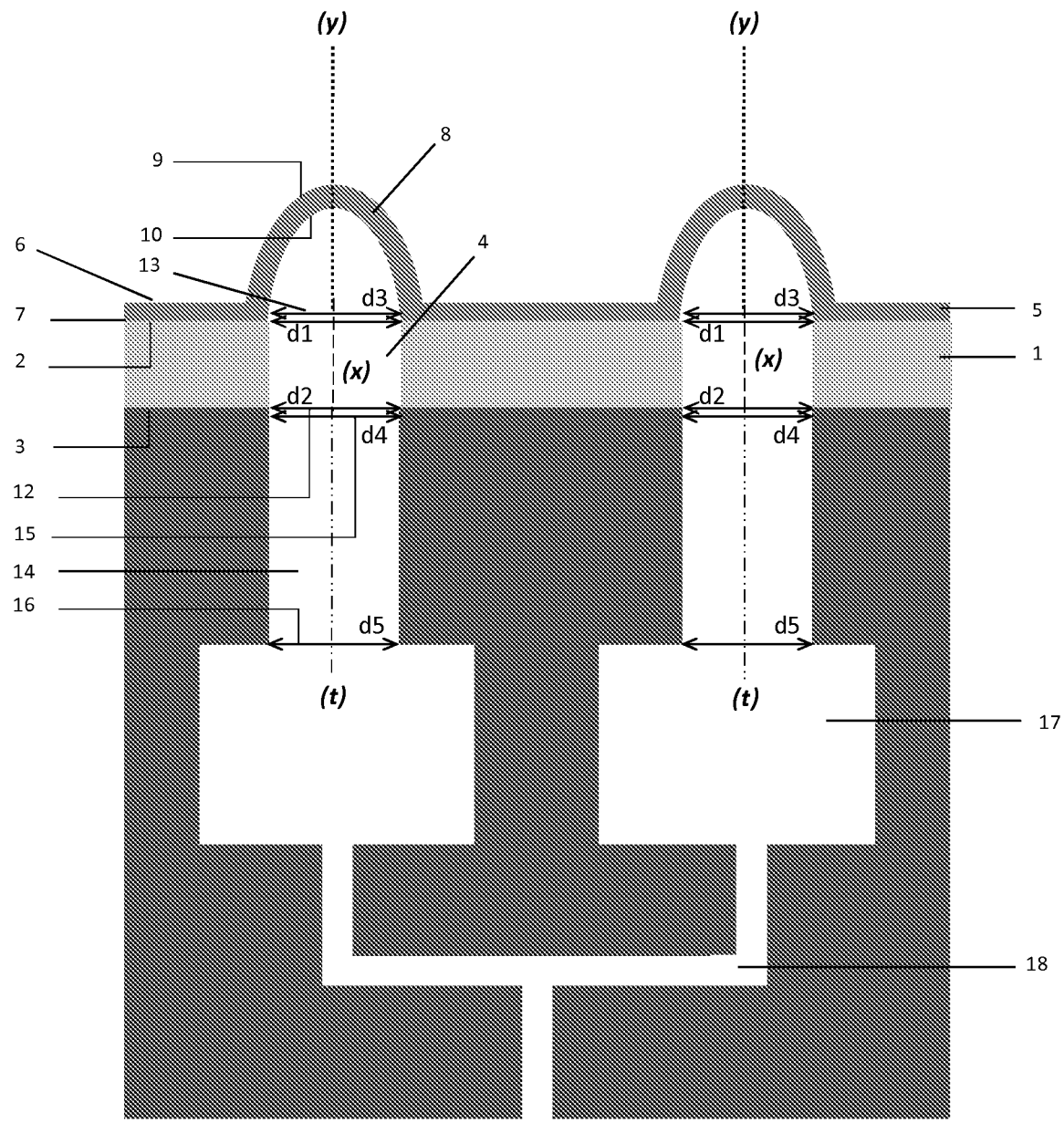

According to a specific embodiment, the invention relates to a microfluidic cell culture chip, wherein each of the upper orifices (15) of the at least two ducts (14) leads to a perforation (4) and the at least two lower orifices (16) of the at least two ducts (14) lead respectively to an intermediate means consisting of a reservoir (17) capable of recovering liquids and making it possible for a conveyance to the outside of the chip via an outlet duct (18) leading to the outside of the base (109) of said lower module (107), said outlet ducts of each of said reservoirs being connected to one another to lead to the outside of the chip at the same site (FIG. 34).

Figure 33:
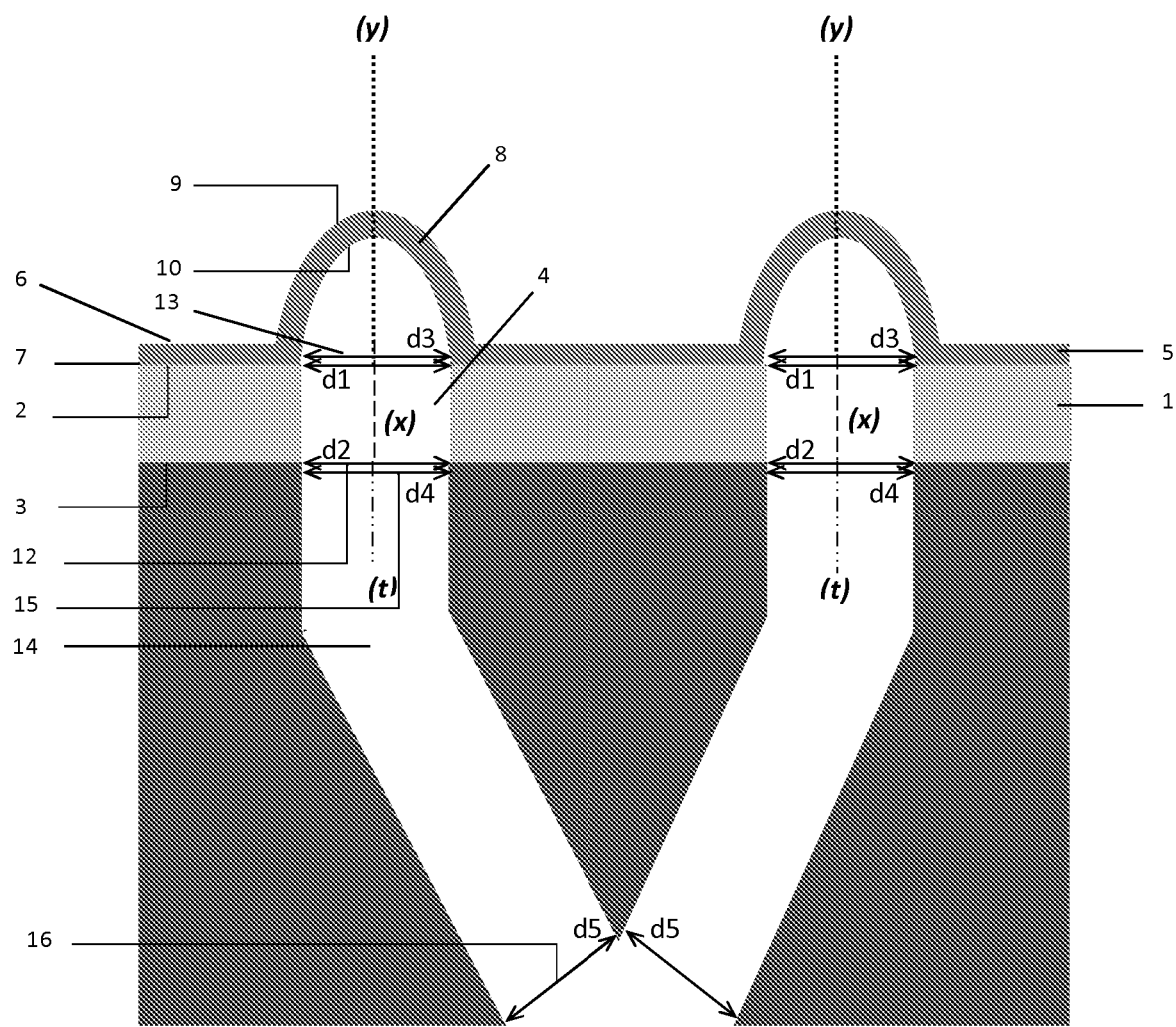
Figure 35:
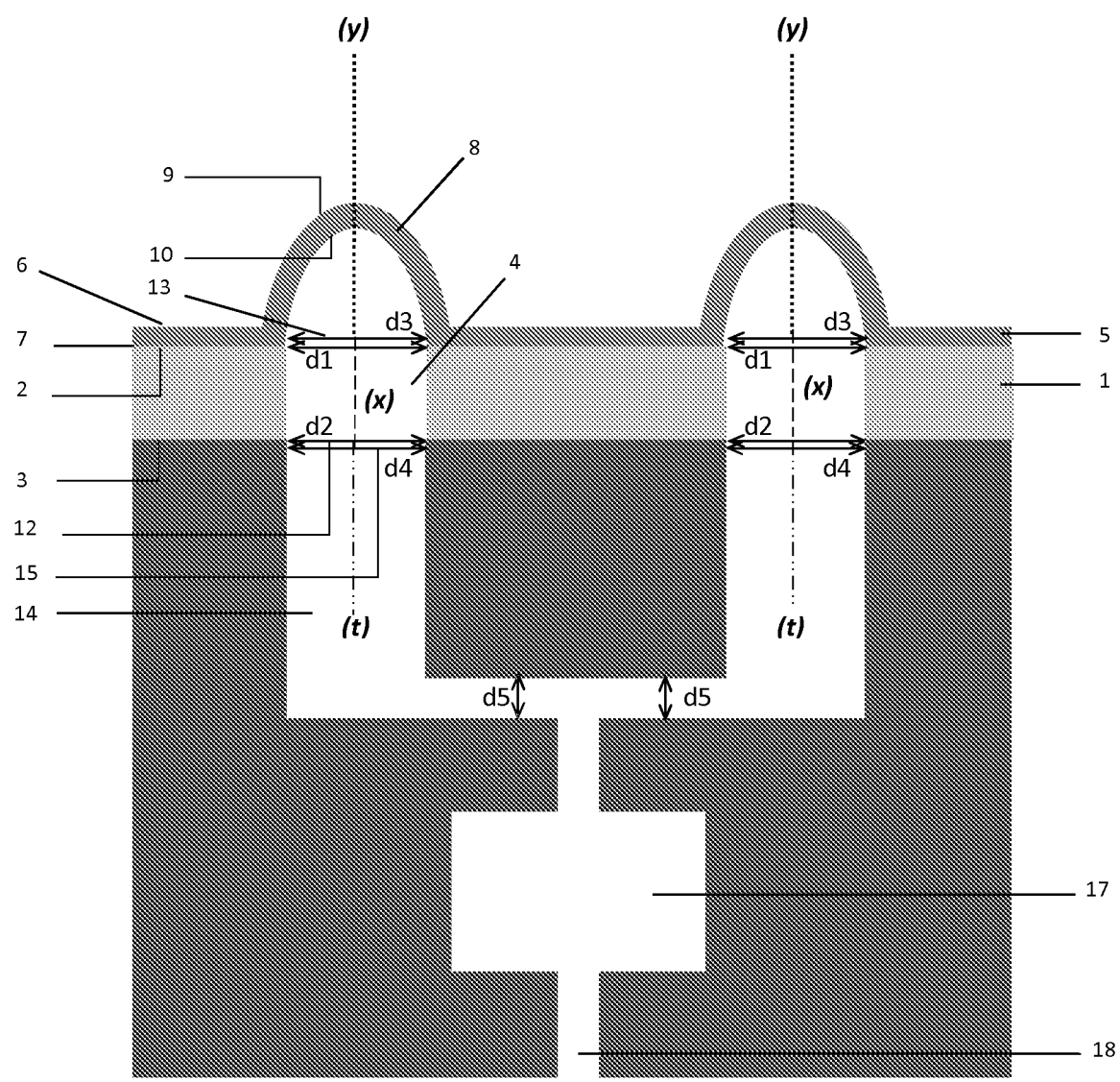

According to a specific embodiment, the invention relates to a microfluidic cell culture chip, wherein the at least two ducts (14) are connected to one another to form a network, such that each of the upper orifices (15) of the at least two ducts (14) leads to a perforation (4) and the lower orifice (16) of each of the at least two ducts (14) themselves lead to the outside of the chip at the same site or via an intermediate means consisting of a reservoir (17) capable of recovering liquids and making it possible for a conveyance to the outside of the chip via an outlet duct (18) leading to the outside of the base (109) of said lower module (107) (FIGS. 33 and 35).

Figure 37:
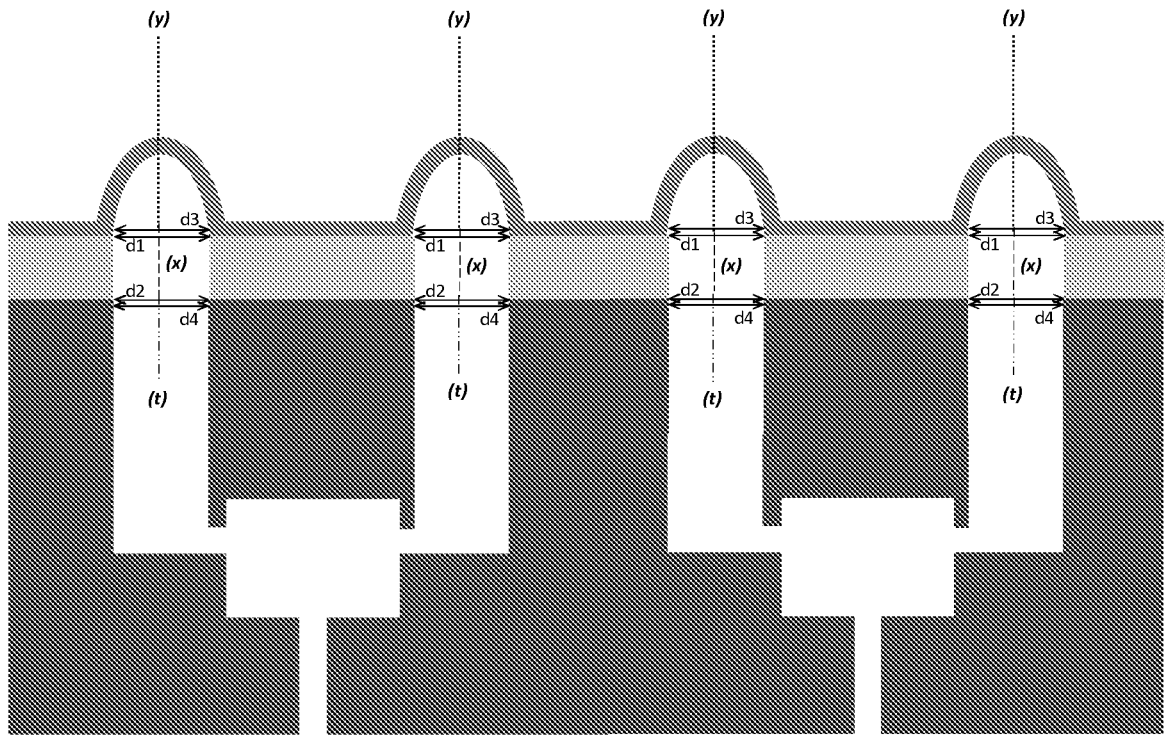

According to a specific embodiment, the invention relates to a microfluidic cell culture chip, wherein each of the upper orifices (15) of the at least two ducts (14) leads to a perforation (4) and a first set of at least two lower orifices (16) of the at least two ducts (14) lead to a first intermediate means consisting of a reservoir (17), and one at least second set of at least two lower orifices (16) of the at least two ducts (14) lead to at least one second intermediate means consisting of a reservoir (17), said first and at least second reservoirs (17) being capable of recovering liquids and each making it possible for a conveyance to the outside of the chip via respective outlet ducts (18) leading to the outside of the base (109) of said lower module (107), at different sites (FIG. 37).

Figure 36:
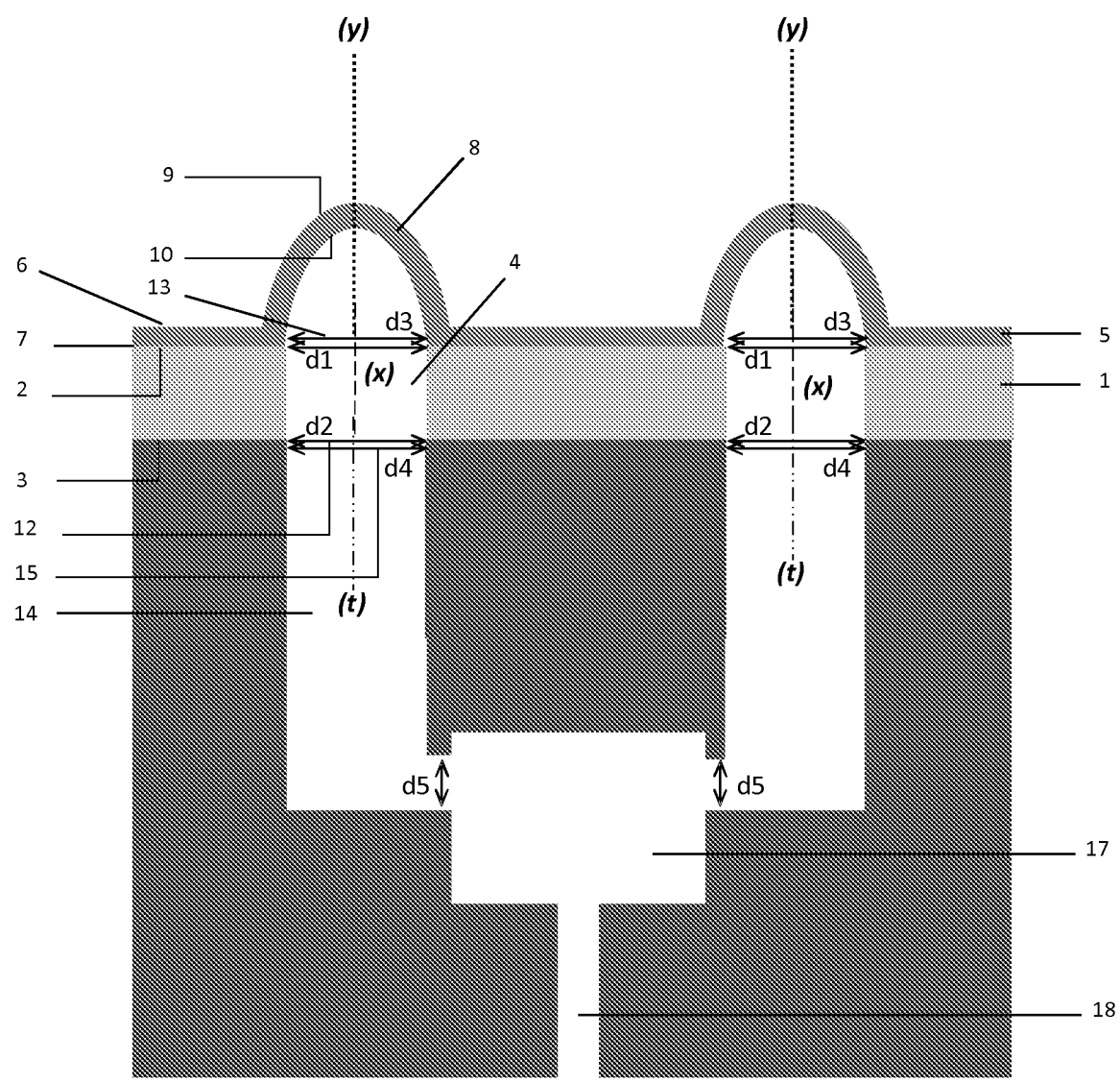

According to a specific embodiment, the invention relates to a microfluidic cell culture chip, wherein each of the upper orifices (15) of the at least two ducts (14) leads to a perforation (4) and the at least two lower orifices (16) of the set of the at least two ducts (14) lead to one same intermediate means consisting of a reservoir (17) capable of recovering liquids and making it possible for a conveyance to the outside of the chip via an outlet duct (18) leading to the outside of the base (109) of said lower module (107) (FIG. 36).

According to a specific embodiment, the invention relates to a microfluidic cell culture chip wherein said lower module (107) has a height of 100 µm to 2 cm.

According to a specific embodiment, the invention relates to a microfluidic cell culture chip wherein said base (109) of the lower module (107) has a height of 100 µm to 2 cm.

According to a specific embodiment, the invention relates to a microfluidic cell culture chip wherein said lower unit (108) has a height of 100 µm to 2 cm.

According to a specific embodiment, the invention relates to a microfluidic cell culture chip wherein the lower module (107) is composed of bioprinted plastic, polycarbonate, tissue culture plastic or SU8.

According to a specific embodiment, the invention relates to a microfluidic cell culture chip wherein the lower module (107) is composed of bioprinted plastic, polycarbonate, tissue culture plastic, glass or SU-8 resin, and said lower module (107) is transparent.

According to a specific embodiment, the invention relates to a microfluidic cell culture chip wherein the base of the lower module (109) is composed of bioprinted plastic, polycarbonate, tissue culture plastic or SU8.

According to a specific embodiment, the invention relates to a microfluidic cell culture chip wherein the base of the lower module (109) is composed of bioprinted plastic, polycarbonate, tissue culture plastic, glass or SU-8 resin, and said base of the lower module (109) is transparent.

According to a specific embodiment, the invention relates to a microfluidic cell culture chip wherein the lower unit (108) is composed of bioprinted plastic, polycarbonate, tissue culture plastic or SU8.

According to a specific embodiment, the invention relates to a microfluidic cell culture chip wherein the lower unit (108) is composed of bioprinted plastic, polycarbonate, tissue culture plastic, glass or SU-8 resin, and said lower unit (108) is transparent.

Upper Module

According to a specific embodiment, the invention relates to a microfluidic cell culture chip which contains an upper module (101) comprising:

a solid and hollow upper unit (102), which consists of a solid surface defining an open volume (chamber) (203), and the edges of the solid surface being capable of being in contact with said central unit (105) of said central module (104) and delimiting the surface of the opening of said open volume;

and a base (103), said upper unit (102) being integrated in said base (103), and forming a whole with said base (103).

The chamber (203) is integrated in the base (103) of the upper module (101), and is located thus surrounded over all the surfaces thereof by said base (103), except for the surface of the open volume of said chamber (203).

According to a specific embodiment, the invention relates to a microfluidic cell culture chip wherein said upper unit (102) of said upper module (101) and said central unit (105) of said central module (104) are assembled such that said surface of the opening of said upper unit (102) is positioned above said upper face (6) of the 3D nanostructured porous membrane (5) of said central unit (105), said surface of the opening and said upper face (6) having an identical shape and an identical surface to one another.

In a specific embodiment, the upper unit comprises an opening on the outside (window), at the solid surface consisting of said chamber making it possible to insert a transparent glass part, compatible with microscopic observation, preferably a microscope slide, in order to observe the cell culture on the outer face of the 3D nanostructured porous membrane and the outer face of the at least one protuberance.

The opening is situated, preferably at a place of the solid surface of said chamber, such as it makes it possible for the observation vertically of the cell culture on the outer face of the protuberance.

Said transparent glass part is positioned on said opening of the solid surface consisting of said chamber, and maintained sealed to said upper unit to maintain a closed space between the upper unit and the central unit.

Preferably, said transparent glass part is maintained sealed to said upper unit using a sealing adhesive.

According to a specific embodiment, the invention relates to a microfluidic cell culture chip wherein said upper unit (102) of said upper module (101) and said central unit (105) of said central module (104) are assembled by the attachment elements (201,204) situated on each of the bases (103, 106) of the upper module (101) and of the central module (104), so as to assemble, in a sealed manner, said surface of the opening of said upper unit (102) and said upper face (6) of the 3D nanostructured porous membrane (5) of said central unit (105).

According to a specific embodiment, the invention relates to a microfluidic cell culture chip wherein said solid and hollow upper unit (102) wherein said solid surface comprises a solid rectangular face and four solid faces, adjacent to said solid rectangular face and adjacent to one another, forming said chamber (203), the free edges of said four solid faces delimiting said surface of the opening of said chamber (206).

According to a specific embodiment, the invention relates to a microfluidic cell culture chip wherein the upper module (101) is composed of bioprinted plastic, polycarbonate, tissue culture plastic or SU8.

According to a specific embodiment, the invention relates to a microfluidic cell culture chip wherein the upper module (101) is composed of bioprinted plastic, polycarbonate, tissue culture plastic, glass or SU-8 resin, and said upper module (101) is transparent.

According to a specific embodiment, the invention relates to a microfluidic cell culture chip wherein the base of the upper module (103) is composed of bioprinted plastic, polycarbonate, tissue culture plastic or SU8.

According to a specific embodiment, the invention relates to a microfluidic cell culture chip wherein the base of the upper module (103) is composed of bioprinted plastic, polycarbonate, tissue culture plastic, glass or SU-8 resin, and said base of the upper module (103) is transparent.

According to a specific embodiment, the invention relates to a microfluidic cell culture chip wherein the upper unit (102) is composed of bioprinted plastic, polycarbonate, tissue culture plastic or SU8.

According to a specific embodiment, the invention relates to a microfluidic cell culture chip wherein the upper unit (102) is composed of bioprinted plastic, polycarbonate, tissue culture plastic, glass or SU-8 resin, and said upper unit (102) is transparent.

According to a specific embodiment, the invention relates to a microfluidic cell culture chip wherein said surface of the opening of said chamber (203) of said upper unit (102) is positioned above said upper face (6) of the 3D nanostructured porous membrane (5) of said central unit (105) to form a closed space delimited by said solid surface of said upper unit (102) and said upper face (6) of the 3D nanostructured porous membrane (5).

Figure 38:
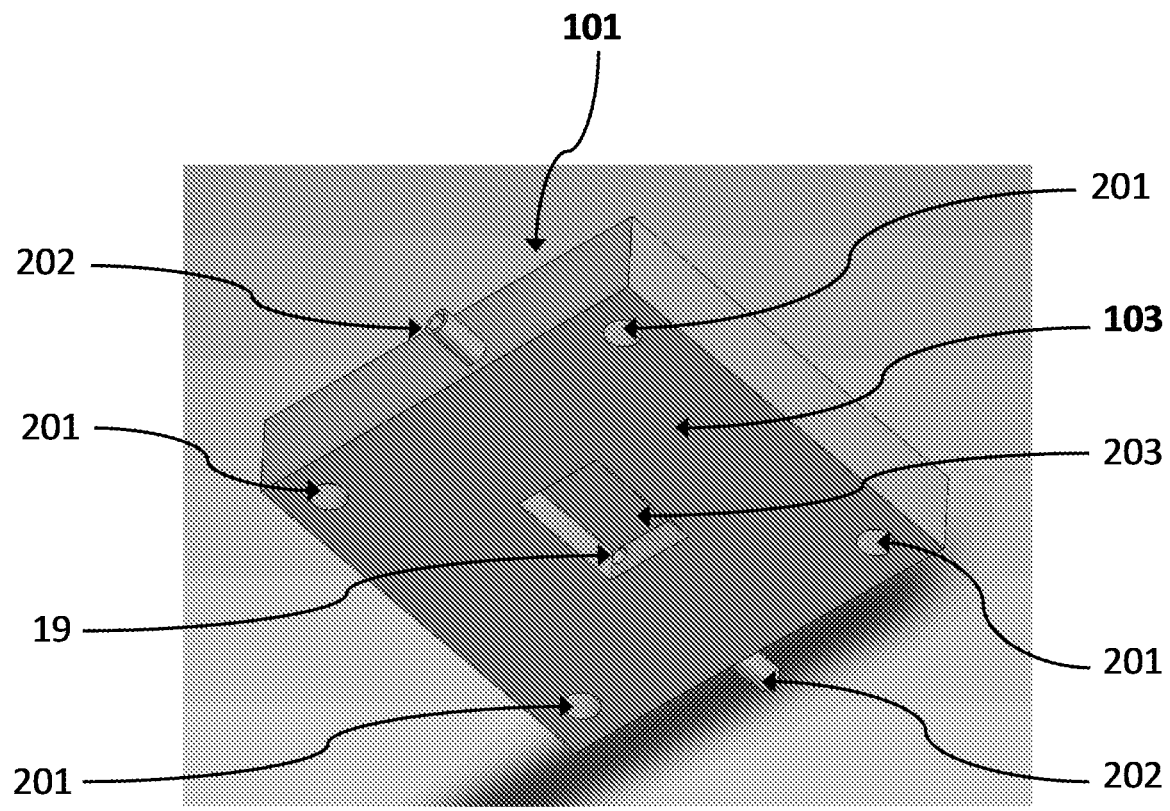
Figure 43:
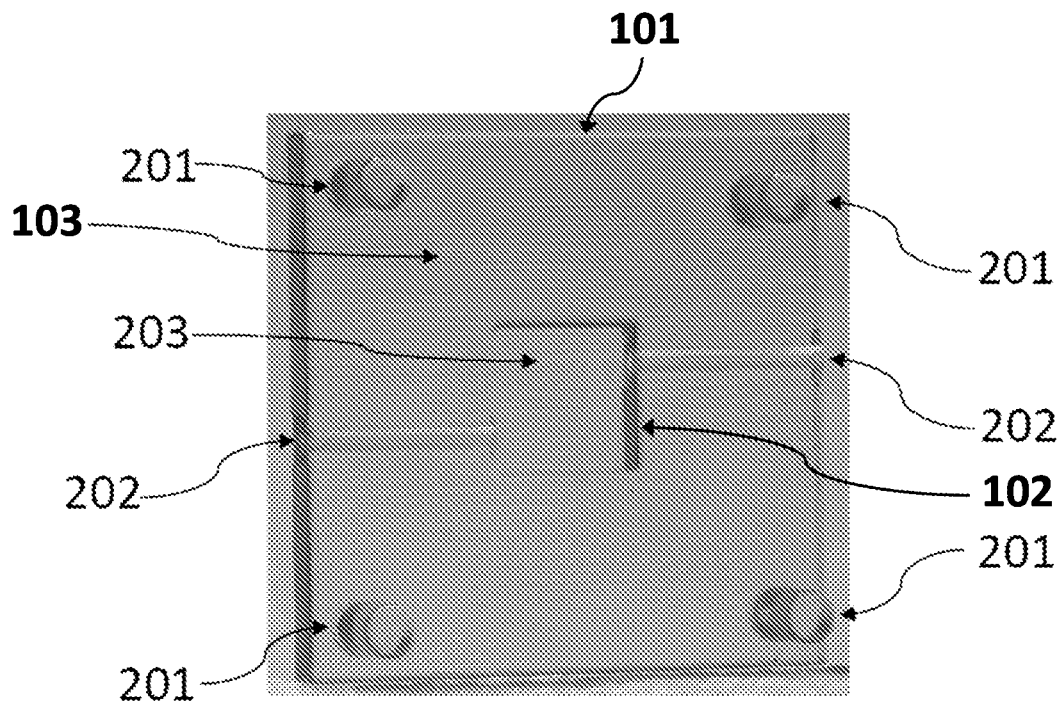

According to a specific embodiment, the invention relates to a microfluidic cell culture chip wherein said surface of the opening of said chamber (203) of said upper unit (102) is positioned above said upper face (6) of the 3D nanostructured porous membrane (5) of said central unit (105), and wherein said at least one solid face of said upper unit (102) has two orifices respectively leading to an inlet/outlet duct (202),
to form a closed space delimited by said solid surface of said upper unit (102), and said upper face (6) of the 3D nanostructured porous membrane (5) of said central unit (105) which could communicate with the outside of said microfluidic chip, only by said two orifices via said inlet/outlet ducts (202) which lead to the outside of the base (109) (FIGS. 38 and 43).

The upper unit comprises two orifices respectively leading to an inlet/outlet duct. The two inlet/outlet ducts extend through the base of the upper module, said unit and said base forming a part of one single holding, such that said two inlet/outlet ducts lead to the outside of said upper base.

When the upper module is assembled to the central module, the assembly of the chamber on the 3D nanostructured porous membrane, makes it possible to define a closed space which could communicate with the outside of said microfluidic chip, only by said two orifices via said inlet/outlet ducts. These ducts also make it possible for the introduction of the culture medium in the chamber, and possibly the introduction of the cells which are cultured on the upper face of said membrane or the outer face of the at least one protuberance.

These inlet/outlet ducts can be coupled with sensors, making it possible for a continuous monitoring of the culture conditions and parameters ($CO_2$, $O_2$, pressure, temperature, glucose, pH sensors). In an alternative embodiment, these sensors can be directly integrated in the chamber (203).

According to a specific embodiment, the invention relates to a microfluidic cell culture chip wherein said upper module (101) has a height of 50 µm to 2 cm, in particular of 1 cm.

According to a specific embodiment, the invention relates to a microfluidic cell culture chip wherein said base (103) of said upper module (101) has a height of 50 µm to 2 cm, in particular of 1 cm.

According to a specific embodiment, the invention relates to a microfluidic cell culture chip wherein said upper unit (102) of said upper module (101) has a height of 50 µm to 2 cm, in particular of 1 cm.

Assembly of the Three Modules

Figure 42:
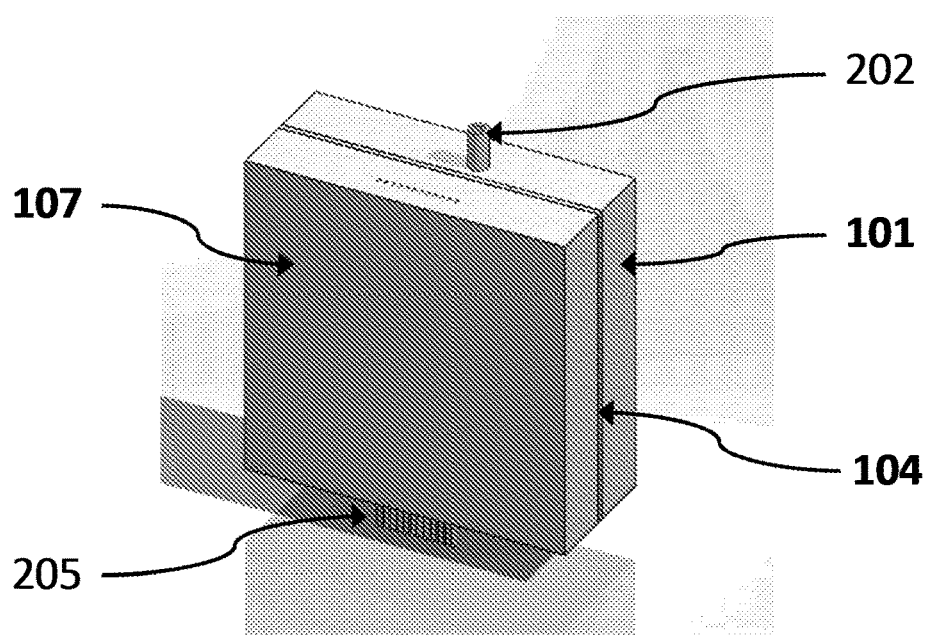
Figure 46:
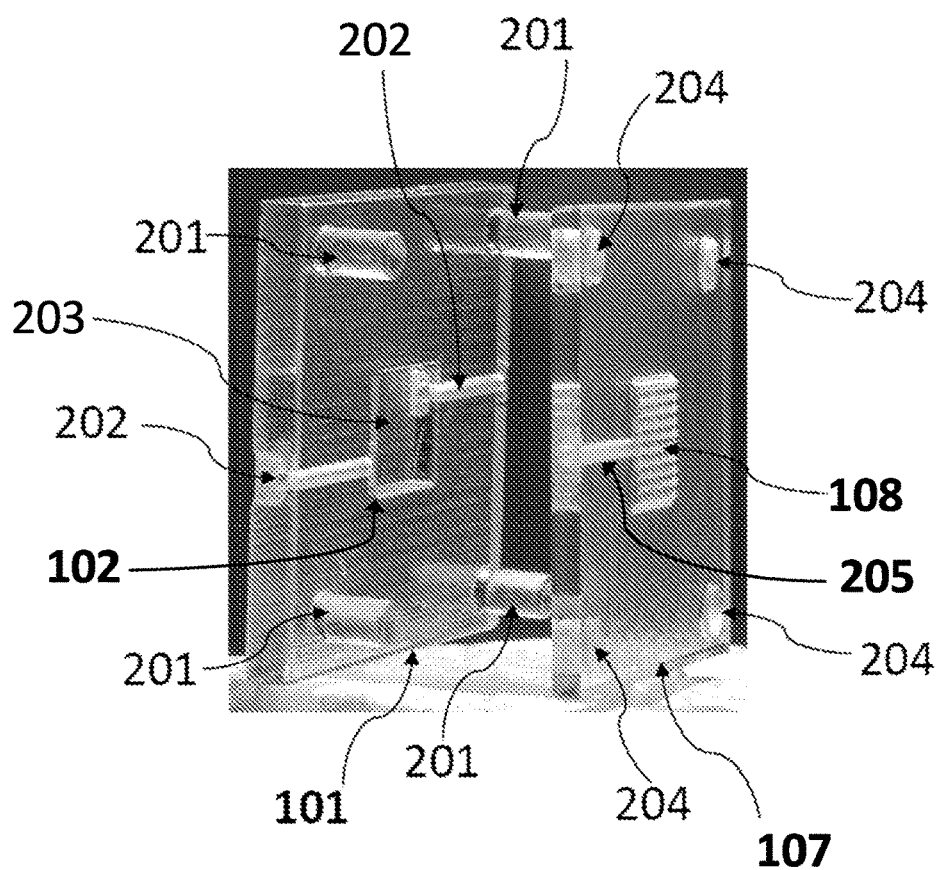
Figure 47:
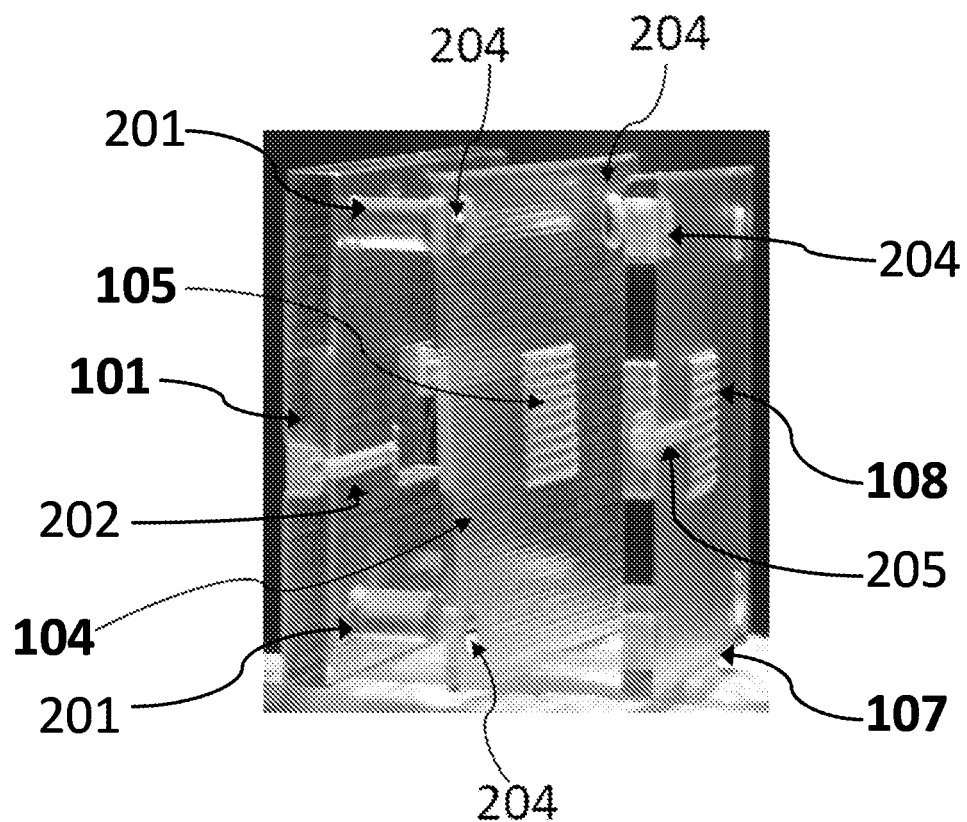

According to a specific embodiment, the invention relates to a microfluidic cell culture chip, comprising an upper module (101), a central module (104) and a lower module (107), and wherein above said modules are assembled such that said surface of the opening of said upper unit (102) of said upper module (101) is positioned above said upper face (2) of the 3D nanostructured porous membrane (5) of said central unit (105) of said central module (104), and the upper orifice (15) of the at least one duct (14), of said upper face of said lower unit (108) of said lower module (107), opens over at least one of said perforations (4) of said support (1) of said central unit (105), said surface of the opening of said upper unit (102) and said upper face (2) of the 3D nanostructured porous membrane (5) of said central unit (105) having an identical shape and an identical surface to one another, said upper face of said lower unit (108) and said lower face of said support (3) of said central unit (105) having an identical shape and an identical surface to one another, and said upper module (101), said central module (104) and said lower module (107) being assembled by the attachment elements (201, 204) situated on each of the respective bases (103, 106, 109) (FIGS. 42, 46 and 47).

The attachment elements situated on the bases of each of the modules make it possible, either to lock the modules two by two, to assemble the upper module with the central module and to assemble the central module with the lower module, or to lock two modules on the third module, to assemble the central module and the lower module on the upper module.

These attachment elements can be male/female lugs or elements, preferably male/female elements.

According to a specific embodiment, the base of the upper module comprises platforms (201) as male attachment elements, and the bases of the central and lower modules comprise perforations (204) as female attachment elements, capable of being locked on said platforms of the upper module.

According to a specific embodiment, the invention relates to a microfluidic cell culture chip, wherein said inner face (10) of said protuberance (8) is in whole, facing said upper orifice (15) of said duct (14):

when said inner face (10) of said at least one protuberance (8) is in whole, facing said at least one perforation (4) of said support (1):

such that when the value of the upper diameter d1 of said at least one perforation (4) is greater than or equal to the value of the diameter d3 of said at least one protuberance (4), and the axis (y), passing through the centre of said circular base (13) and perpendicular to said support (1), and the axis (x), passing through the centre of the upper section (11) of said perforation (4) and perpendicular to said support (1), are combined; or such that the value of the upper diameter d1 of said at least one perforation (4) is greater than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value less than or equal to [(value of d1−value of d3)/2]

and when said perforation (4) of said support (1) is in whole, facing said upper orifice (15) of said duct (14):

such the axis (y), passing through the centre of said circular base (13) of said protuberance (8) and perpendicular to said support (1), and the axis (t), passing through the centre of said upper orifice (15) of said duct (14) and perpendicular to said support (1), are combined, or distinct from one another by a distance, less than or equal to [(value of d4−value of d3)/2] when the value of d4 is greater than the value of d2.

According to a specific embodiment, the invention relates to a microfluidic cell culture chip, wherein said inner face (10) of said protuberance (8) is partially facing said upper orifice (15) of said duct (14):

when said inner face (10) of said at least one protuberance (8) is in whole, facing said at least one perforation (4) of said support (1):

such that when the value of the upper diameter d1 of said at least one perforation (4) is greater than or equal to the value of the diameter d3 of said at least one protuberance (4), and the axis (y), passing through the centre of said circular base (13) and perpendicular to said support (1), and the axis (x), passing through the centre of the upper section (11) of said perforation (4) and perpendicular to said support (1), are combined; or such that the value of the upper diameter d1 of said at least one perforation (4) is greater than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value, less than or equal to [(value of d1−value of d3)/2].

and when the axis (y), passing through the centre of said circular base (13) of said protuberance (8) and perpendicular to said support (1), and the axis (t), passing through the centre of said upper orifice (15) of said duct (14) and perpendicular to said support (1), are combined or distinct from one another by a distance, less than or equal to [(value of d4/2)+(4/10 of value of d3)].

According to a specific embodiment, the invention relates to a microfluidic cell culture chip, wherein said inner face (10) of said protuberance (8) is partially facing said upper orifice (15) of said duct (14):

when said inner face (10) of said at least one protuberance (8) is in whole, facing said at least one perforation (4) of said support (1):

such that when the value of the upper diameter d1 of said at least one perforation (4) is greater than or equal to the value of the diameter d3 of said at least one protuberance (4), and the axis (y), passing through the centre of said circular base (13) and perpendicular to said support (1), and the axis (x), passing through the centre of the upper section (11) of said perforation (4) and perpendicular to said support (1), are combined; or such that the value of the upper diameter d1 of said at least one perforation (4) is greater than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance, of a value less than or equal to [(value of d1−value of d3)/2].

and when
the axis (y), passing through the centre of said circular base (13) of said protuberance (8) and perpendicular to said support (1), and the axis (t), passing through the centre of said upper orifice (15) of said duct (14) and perpendicular to said support (1), are combined or distinct from one another by a distance, less than or equal to [[(value of d4+value of d4)/2]−10 µm].

According to a specific embodiment, the invention relates to a microfluidic cell culture chip, wherein said inner face (10) of said protuberance (8) is partially facing said upper orifice (15) of said duct (14):
when said inner face (10) of said at least one protuberance (8) is in whole, facing said at least one perforation (4) of said support (1):
such as when the value of the upper diameter d1 of said at least one perforation (4) is greater than or equal to the value of the diameter d3 of said at least one protuberance (4), and the axis (y), passing through the centre of said circular base (13) and perpendicular to said support (1), and the axis (x), passing through the centre of the upper section (11) of said perforation (4) and perpendicular to said support (1), are combined; or
such that the value of the upper diameter d1 of said at least one perforation (4) is greater than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value, less than or equal to [(value of d1−value of d3)/2].

and when
the axis (y), passing through the centre of said circular base (13) of said protuberance (8) and perpendicular to said support (1), and the axis (t), passing through the centre of said upper orifice (15) of said duct (14) and perpendicular to said support (1), are combined or distinct from one another by a distance, less than or equal to [value of d4/2].

According to a specific embodiment, the invention relates to a microfluidic cell culture chip, wherein said inner face (10) of said protuberance (8) is partially facing said upper orifice (15) of said duct (14):
when said inner face (10) of said at least one protuberance (8) is partially facing said at least one perforation (4) of said support (1):
such that the value of the upper diameter d1 of said at least one perforation (4) is less than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are combined, or distinct from one another by a value, less than or equal to [(value of d1/2)+(4/10 of value of d3)].
and said axis (x) and the axis (t), passing through the centre of said upper orifice (15) of said duct (14) and perpendicular to said support (1), are combined when the value of the diameter d2 is equal to or greater than the value of the diameter d4,
or are distinct from one another by a distance of a value, less than or equal to [(value of d4−value of d1)/2], when the value of the diameter d4 is greater than the value of the diameter d2.

According to a specific embodiment, the invention relates to a microfluidic cell culture chip, wherein said inner face (10) of said protuberance (8) is partially facing said upper orifice (15) of said duct (14):
when said inner face (10) of said at least one protuberance (8) is partially facing said at least one perforation (4) of said support (1):
such that the value of the upper diameter d1 of said at least one perforation (4) is less than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are combined, or distinct from one another by value, less than or equal to [[(value of d3+value of d1)/2]−10 µm].
and said axis (x) and the axis (t), passing through the centre of said upper orifice (15) of said duct (14) and perpendicular to said support (1), are combined when the value of the diameter d2 is equal to or greater than the value of the diameter d4,
or are distinct from one another by a distance of a value, less than or equal to [(value of d4−value of d1)/2], when the value of the diameter d4 is greater than the value of the diameter d2.

According to a specific embodiment, the invention relates to a microfluidic cell culture chip, wherein said inner face (10) of said protuberance (8) is partially facing said upper orifice (15) of said duct (14):
when said inner face (10) of said at least one protuberance (8) is partially facing said at least one perforation (4) of said support (1):
such that the value of the upper diameter d1 of said at least one perforation (4) is less than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are combined, or distinct from one another by a value, less than or equal to [(value of d3−value of d1)/2],
and said axis (x) and the axis (t), passing through the centre of said upper orifice (15) of said duct (14) and perpendicular to said support (1), are combined when the value of the diameter d2 is equal to or greater than the value of the diameter d4,
or are distinct from one another by a distance of a value, less than or equal to [(value of d4−value of d1)/2], when the value of the diameter d4 is greater than the value of the diameter d2.

According to a specific embodiment, the invention relates to a microfluidic cell culture chip, wherein said inner face (10) of said protuberance (8) is partially facing said upper orifice (15) of said duct (14):
when said inner face (10) of said at least one protuberance (8) is partially facing said at least one perforation (4) of said support (1):
such that the value of the upper diameter d1 of said perforation (4) is equal to the value of the diameter d3 of said protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a lesser value [value of d1/2], and said axis (x) and the axis (t), passing through the centre of said upper orifice (15) of said duct (14) and perpendicular to said support (1), are combined when the value of the diameter d2 is equal to or greater than the value of the diameter d4, or are distinct from one another by a distance of a value, less than or equal to [(value of d4−value of d1)/2], when the value of the diameter d4 is greater than the value of the diameter d2.

According to a specific embodiment, the invention relates to a microfluidic cell culture chip, wherein said inner face (10) of said protuberance (8) is partially facing said upper orifice (15) of said duct (14):

when said inner face (10) of said at least one protuberance (8) is partially facing said at least one perforation (4) of said support (1):

such that the value of the upper diameter d1 of said perforation (4) is greater than the value of the diameter d3 of said protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value, less than or equal to [(value of d1−value of d3)/2], and said axis (x) and the axis (t), passing through the centre of said upper orifice (15) of said duct (14) and perpendicular to said support (1), are combined, or said axis (x) and said axis (y) are combined.

According to a specific embodiment, the invention relates to a microfluidic cell culture chip, wherein said inner face (10) of said protuberance (8) is partially facing said upper orifice (15) of said duct (14):

when said inner face (10) of said at least one protuberance (8) is partially facing at least one perforation (4) of said support (1):

such that the value of the upper diameter d1 of said perforation (4) is greater than the value of the diameter d3 of said protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value, less than or equal, are combined, or distinct from one another by a value, less than or equal to [(value of d1/2)+(4/10 of value of d3)]

and said axis (x) and the axis (t), passing through the centre of said upper orifice (15) of said duct (14) and perpendicular to said support (1), are distinct from one another by a distance, such that at least 1/10 of the diameter d3 are in whole, facing the diameter d4.

According to a specific embodiment, the invention relates to a microfluidic cell culture chip, wherein said inner face (10) of said protuberance (8) is partially facing said upper orifice (15) of said duct (14):

when said inner face (10) of said at least one protuberance (8) is partially facing said at least one perforation (4) of said support (1):

such that the value of the upper diameter d1 of said perforation (4) is greater than the value of the diameter d3 of said protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value, less than or equal, are combined, or distinct from one another by a value, less than or equal to [[(value of d3+value of d1)/2]−10 m]

and said axis (x) and the axis (t), passing through the centre of said upper orifice (15) of said duct (14) and perpendicular to said support (1), are distinct from one another by a distance such that at least 10 μm of the diameter d3 is in whole, facing the diameter d4.

In an embodiment of the invention, the central unit contains:

a support consisting of a non-resorbable membrane (1), comprising an upper face (2) and a lower face (3), perforated by at least one perforation (4)

a 3D nanostructured porous membrane (5) comprising an upper face (6) and a lower face (7), and comprising at least one protuberance (8), said at least one protuberance comprising an outer face (9) and an inner face (10) and forming a relief structure on the side of the upper face (6) of the 3D nanostructured membrane (5), said protuberance being, in particular, in the shape of a hollow dome having a circular base (13), said upper face (6) of the 3D nanostructured membrane being positioned, secured to said lower face (2) of said support and said at least one protuberance (8) being on the side of the upper face (2) of said support (1).

Thus, according to a specific embodiment, the invention relates to a microfluidic cell culture chip wherein said upper unit (102) of said upper module (101) and said central unit (105) of said central module (104) are assembled such that said surface of the opening of said upper unit (102) is positioned above said upper face (2) of the support consisting of a non-resorbable membrane (1) of said central unit (105), to form a closed space, delimited by said solid surface of said upper unit (102), said upper face (2) of the support consisting of a non-resorbable membrane (1) and the outer face (9) of the protuberances, said surface of the opening and said upper face (2) having an identical shape and an identical surface to one another, said upper unit (102) of said upper module (101) and said central unit (105) of said central module (104) being assembled by attachment elements (201, 204) situated on each of the bases (103, 106) of the upper module (101) and of the central module (104), so as to assemble in a sealed manner, said surface of the opening of said upper unit (102) and said upper face (2) of the support consisting of a non-resorbable membrane (1) of said central unit (105), and advantageously said at least one solid face of said upper unit (102) has two orifices leading respectively to an inlet/outlet duct (202), making it possible for said closed space, to communicate with the outside of said microfluidic chip via said inlet/outlet ducts (202) which lead to the outside of the base (109).

According to a specific embodiment, the invention relates to a microfluidic cell culture chip wherein said inner face (10) of said at least one protuberance (8) is in whole, or partially, facing said at least one perforation (4) of said support (1).

The 3D nanostructured membrane comprising at least one protuberance and the support perforated by at least one perforation, are positioned to one another such that the inner face of said protuberance are in whole, or partially, facing the circular section of said perforation at the upper face of the support.

According to a specific embodiment, the invention relates to a microfluidic cell culture chip wherein said inner face (10) of said at least one protuberance (8) is in whole, facing said at least one perforation (4) of said support (1):
- when the value of the upper diameter d1 of said at least one perforation (4) is greater than or equal to the value of the diameter d3 of said at least one protuberance (4), and the axis (y), passing through the centre of said circular base (13) and perpendicular to said support (1), and the axis (x), passing through the centre of the upper section (11) of said perforation (4) and perpendicular to said support (1), are combined; or
- when the value of the upper diameter d1 of said at least one perforation (4) is greater than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value, less than or equal to [(value of d1−value of d3)/2].

According to a specific embodiment, the invention relates to a microfluidic cell culture chip, comprising an upper module (101), a central module (104) and a lower module (107), and wherein the above said modules are assembled such that
- said surface of the opening of said upper unit (102) of said upper module (101) is positioned above said upper face (2) of the support consisting of a non-resorbable membrane (1) and of the outer face (9) of said at least one protuberance (8) of said central unit (105) of said central module (104),
- and the upper orifice (15) of the at least one duct (14), of said upper face of said lower unit (108) of said lower module (107), opens on at least one of said perforations (4) of said support (1) of said central unit (105),
- said surface of the opening of said upper unit (102) and said upper face (2) of the support consisting of a non-resorbable membrane (1) of said central unit (105) having an identical shape and an identical surface to one another,
- said upper face of said lower unit (108) and said lower face of said support (3) of said central unit (105) having an identical shape and an identical surface to one another, and said upper module (101), said central module (104) and said lower module (107) being assembled by the attachment elements (201, 204) situated on each of the respective bases (103, 106, 109)
wherein said inner face (10) of said protuberance (8) is in whole, facing said upper orifice (15) of said duct (14):
- when said inner face (10) of said at least one protuberance (8) is in whole, facing said at least one perforation (4) of said support (1):
  - such that when the value of the upper diameter d1 of said at least one perforation (4) is greater than or equal to the value of the diameter d3 of said at least one protuberance (4), and the axis (y), passing through the centre of said circular base (13) and perpendicular to said support (1), and the axis (x), passing through the centre of the upper section (11) of said perforation (4) and perpendicular to said support (1), are combined; or
  - such that the value of the upper diameter d1 of said at least one perforation (4) is greater than the value of the diameter d3 of said at least one protuberance (8), and the axis (y), passing through the centre of said circular base (13) and perpendicular to said support (1), and the axis (x), passing through the centre of the upper section (11) of said perforation (4) and perpendicular to said support (1), are distinct from one another by a distance of a value, less than or equal to [(value of d1−value of d3)/2];
- and when said perforation (4) of said support (1) is in whole, facing said upper orifice (15) of said duct (14):
  - such that the axis (y), passing through the centre of said circular base (13) of said protuberance (8) and perpendicular to said support (1), and the axis (t), passing through the centre of said upper orifice (15) of said duct (14) and perpendicular to said support (1), are combined, or distinct from one another by a distance, less than or equal to [(value of d4−value of d3)/2] when the value of d4 is greater than the value of d2.

Figure 50:
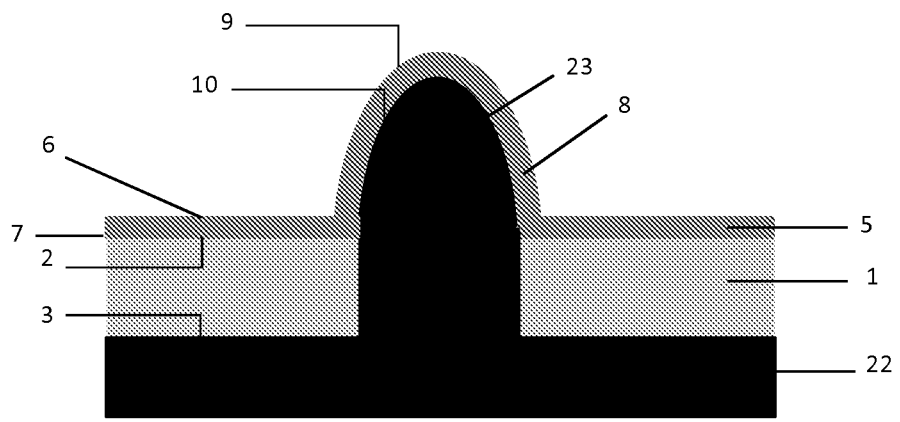
Figure 51:
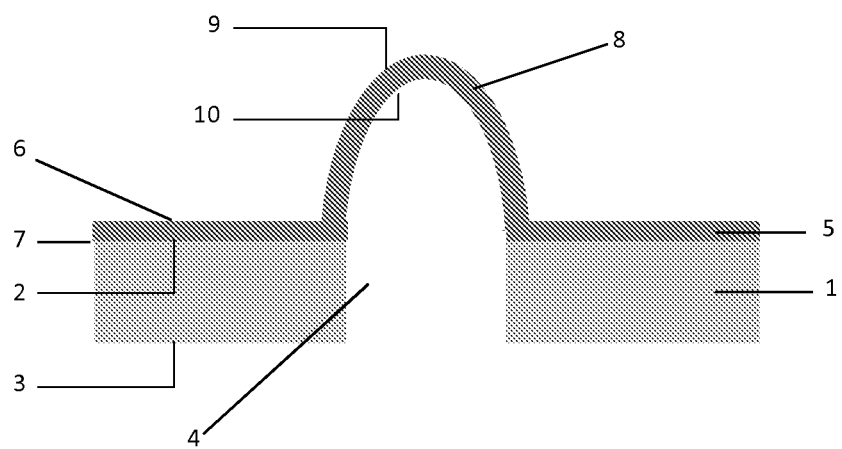

The invention also relates to a process for producing a microfluidic cell culture chip according to the invention, wherein the production of said central unit (105) of said central module (104) comprises:
- a step of extruding a resorbable polymer solution (22) through the at least one perforation (4) of said support (1) to form at least one 3D nanostructure (23) on the side of said upper face (2) of said support (1) (FIGS. 48 and 49), followed by
- a step of polymerising said resorbable polymer solution, to make rigid said at least one 3D nanostructure (23), said at least one 3D nanostructure (23) forming a resorbable polymer mould (22) on the side of said upper face of said support after polymerisation, followed by
- a step of applying at least one continuous layer of at least one polyelectrolyte covering the upper face (2) of said support (1) and the surface of said resorbable polymer mould (22), to constitute the 3D nanostructured porous membrane (5) (FIG. 50), by
- a step of dissolving said resorbable polymer mould to obtain said lower face (7) of said 3D nanostructured porous membrane (5) positioned secured to said upper face (2) of said support (1) and said inner face (10) of the at least one protuberance (8) positioned in whole, facing said at least one perforation (4) (FIG. 51).

The first step of producing the central module is a step of extruding a resorbable polymeric solution through one or more perforations of said support consisting of a non-resorbable material, i.e. a material which could not be removed by a physical process, nor by a chemical process in an aqueous solvent.

The resorbable polymeric material used for the solution is initially in the form of viscous liquid to make it possible for the extrusion through the perforations of the support.

The term, "viscous" is used here to qualify a fluid which has a resistance to deformation under a shear stress, which is at least the same as that of pure water and preferably substantially greater than that of pure water. In other words, a viscous liquid used for the extrusion circulates slower than pure water, property due to the greater viscosity thereof than pure water. The viscosity property of the liquid used for the extrusion is important, as such a viscous liquid makes it possible for a better conservation of the shape of the protuberance, during the extrusion process, than a solution which has the viscosity of pure water. The preferred range of viscosity of the liquid for the extrusion is between 1 (pure water) and 100 Pa·s, and preferably, the viscosity of the liquid is between 0.1 Pa·s and 1 Pa·s.

The term, "extrusion" is used here to define a step wherein a material in the form of viscous liquid is passed by force through a matrix to give a shape, predetermined by said matrix, to said viscous material. In the scope of the present invention, the matrix consists of the support comprising at least one perforation and said material in viscous liquid state consists of resorbable polymer. The extrusion of this resorbable polymer in viscous state, from the lower face of said support, to the outer face of said support, through the at least one perforation, makes it possible to give a 3D nanostructure shape to said resorbable polymer on the side of the upper face of said support.

According to a specific embodiment, the invention relates to a process for producing a microfluidic cell culture chip, wherein the step of extruding said resorbable polymer solution (22) through the at least one perforation (4) of said support (1), makes it possible to form 3D nanostructures (23) on the side of said upper face (2) of said support (1) in the shape of a dome.

The 3D nanostructure obtained after extrusion through the perforations and the polymerisation of said resorbable polymeric solution, has the technical effect of being used as a mould for the formation of protuberances of the 3D nanostructured porous membrane.

The extrusion is stopped when the resorbable polymeric solution has formed a 3D nanostructure of a desired length, to be used as a mould for the desired protuberance.

The resorbable polymeric solution is thus left without stress to make it possible for the polymerisation or gelation thereof, and thus give solid 3D nanostructures which exceed the side of the upper face of said support through the perforations.

The polymerisation is done directly on the support consisting of a non-resorbable membrane and comprising at least one perforation.

After polymerisation, the 3D nanostructures obtained make it possible to constitute a mould to obtain protuberances of the 3D nanostructured porous membrane.

The surface formed by the upper face of the support and the 3D nanostructures formed by extrusion and exceeding the side of the upper face of said support through the perforations, is then covered by a porous membrane consisting of a polyelectrolyte film.

The polyelectrolytes have the property of being able to take the shape of any type of 3D structure consisting of any type of material (even resorbable), and to conserve the 3D shape thus given, during the removal of the 3D structure having been used as a mould.

This polyelectrolyte film is a multilayer film, made by using the layer-by-layer technique.

The aim of this technique is to adsorb successive layers of polyelectrolytes on the surface formed by the upper face of the support and the 3D nanostructures exceeding through the perforations of said support, to create a plurality of fine polyelectrolyte layers.

Preferably, the polyelectrolytes used are PAH and PSS. PAH and PSS solutions are prepared at a concentration of 1 mg/ml with 0.5 mol/l of NaCl.

The polyelectrolyte multilayer film is constructed by starting equally with one of the polyelectrolytes and by ending equally with one of the polyelectrolytes, but by considering the alternation of the layers between oppositely-charged polyelectrolytes.

Between the changes of polyelectrolyte solution, the surface is thoroughly rinsed with MilliQ water (18MΩ·cm).

This process is repeated until the desired number of polyelectrolyte layers is obtained.

This process makes it possible to obtain a continuous, final polyelectrolyte multilayer film which consists of a continuous film over all of the surface formed by the upper face of the support and the 3D nanostructures exceeding through the perforations of said support.

Thus, this final polyelectrolyte multilayer film has protuberances obtained by moulding during the application of successive layers of polyelectrolytes on the 3D nanostructures coming from extrusion through perforations of the support.

Once the surface formed by the upper face of the support and the 3D nanostructures, is covered by the continuous polyelectrolyte multilayer film, the mould formed by the 3D nanostructures made of resorbable polymeric material is dissolved.

It must be noted, that the use of a support consisting of a non-resorbable material, i.e. a material which could not be removed by a physical process, nor by a chemical process in an aqueous solvent, makes it possible to conserve said intact support coming from this dissolution step.

The dissolution of the resorbable polymeric material gives a continuous polyelectrolyte multilayer film, firmly bound to the support, and which have protuberances conserving the shape of the 3D nanostructures on which they have been moulded. This continuous film thus consists of the 3D nanostructured porous membrane.

The final structure composed of the 3D nanostructured porous membrane attached on the support, can be easily handled and forms the central module of said microfluidic cell culture chip.

This central module can be disinfected by washing three times consecutively with 70% ethanol, then by washing three to four times consecutively with the cell culture medium to remove any residual trace of ethanol.

It is also possible to sterilise the central module by using ethylene oxide gas.

According to a specific embodiment, the invention relates to a process for producing a microfluidic cell culture chip, wherein the step of extruding said resorbable polymer solution (22) through the at least one perforation (4) of said support (1) is carried out by using a pumping system.

This extrusion of the resorbable polymetric solution is done using a pumping system which can be manually or mechanically controlled (by a motor).

The pumping system can consist of, for example, a syringe or a piston to induce a continuous flow of said resorbable polymer solution (22) through said at least one perforation (4).

In another embodiment, said resorbable polymer solution (22) can be extruded through at least one perforation (4) using two parallel flat plates which can be moved towards one another, either manually or mechanically, using a motor, for example. One of the flat plates is positioned on the outer face of the upper module (204) and the other flat plate is positioned on the outer face of the lower module (101), the two flat plates thus being positioned parallel against one another. The movement of said flat and parallel plates, towards one another, thus makes it possible to apply a force to said resorbable polymer solution (22). In such a case, the force applied to the resorbable polymer solution (22) obligates said resorbable polymer solution (22) to circulate through said at least one perforation (4).

The extrusion can be done in a liquid or in the air.

According to a specific embodiment, the invention relates to a process for producing a microfluidic cell culture chip, wherein the step of extruding said resorbable polymer solution (22) through the at least one perforation (4) of said support (1), is carried out in a liquid.

In the case of extrusion in a liquid, the liquid is selected so as to not lead to the resorption of the polymer used to form the protuberance.

In the case of a 3D nanostructure extruded in a liquid, when the liquid is above the upper face of the support, this leads to a static fluid pressure which consists of a force directed in the opposite direction to increasing the length of the 3D nanostructure, and thus acts against the increasing of the length of the 3D nanostructure. This magnitude of the static fluid pressure is calculated by multiplying the density (p) of the liquid by the depth (t) of the liquid above the upper face of the support, and by the gravity force (g), that is in the form of formula ptg. This magnitude of the static fluid pressure acts so as to reduce the height of the 3D nanostructure. For example, for a depth of 1 mm of a diluted salt solution (density=1), solution used in the case of mimicry of extracellular fluids of the body, the magnitude of the static fluid pressure which acts against the formation in length of the 3D nanostructure is 9.8 millipascals.

As Young's modulus of the polyelectrolyte solution used as a resorbable polymer for the extrusion, is generally around 100 to 400 megapascals, there is thus a marginal reduction of the length of the 3D nanostructure formed during the extrusion (for example, in the worst case, for a Young's modulus of 100 megapascals, the reduction of the length will be around $10^{-5}$%).

In the case of a 3D nanostructure extruded in a liquid, if the liquid is below the lower face of the support, there is thus no static fluid resistance force which acts against the formation in length of the 3D nanostructure. In this case, the protuberance reaches the same length as a 3D nanostructure extruded in the air.

According to a specific embodiment, the invention relates to a process for producing a microfluidic cell culture chip, wherein the step of extruding said resorbable polymer solution (22) through the at least one perforation (4) of said support (1), is carried out in the air.

In the case of a 3D nanostructure extruded in the air, there is no pressure acting against the formation in length of the 3D nanostructure.

The invention also relates to an alternative process for producing a microfluidic cell culture according to the invention, wherein the production of said central unit (105) of said central module (104) comprises:

a step of pouring a resorbable polymer solution (22) on the upper face (209) of a mould (H), said mould being in particular made of plastic, comprising at least one moulded 3D nanostructure (208) on said upper face (209), (FIGS. 53 and 54) followed by a step of polymerising said resorbable polymer solution (22) to make rigid said resorbable polymer solution and form a resorbable polymer matrix (210), followed by a step of removing said mould to form a resorbable polymer matrix (210) comprising at least one negative mould of said at least one 3D nanostructure (211), (FIG. 55), followed by a step of applying at least one continuous layer of at least one polyelectrolyte on the lower face (212) of said resorbable polymer matrix (210) comprising at least one negative mould of said at least one 3D nanostructure (211), to consist of a 3D nanostructured porous membrane (5) comprising at least one protuberance (8) (FIG. 56), followed by a step of dissolving said resorbable polymer matrix.

Figure 58:
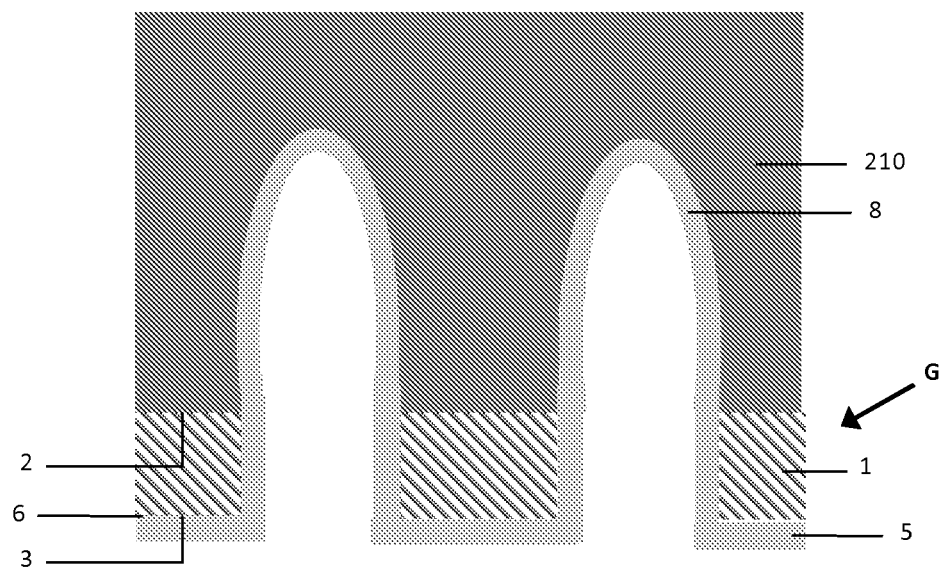
Figure 59:
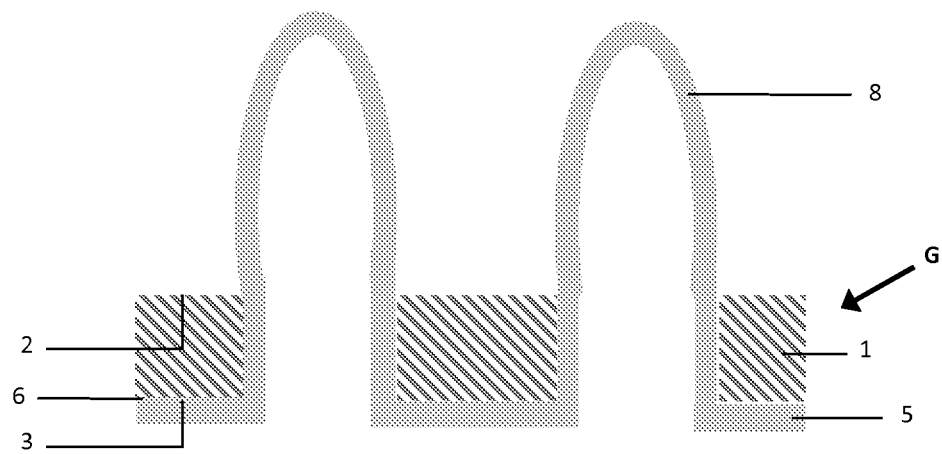

According to a specific embodiment, the invention also relates to an alternative process for producing a microfluidic cell culture chip according to the invention, wherein the production of said central unit (105) of said central module (104) comprises:

a step of pouring a resorbable polymer solution (22) on the upper face (209) of a mould (H), said mould being in particular made of plastic, comprising at least one moulded 3D nanostructure (208) on said upper face (209), (FIGS. 53 and 54) followed by a step of polymerising said resorbable polymer solution (22) to make rigid said resorbable polymer solution and form a resorbable polymer matrix (210), followed by a step of removing said mould (H) to form a resorbable polymer matrix (210) comprising at least one negative mould of said at least one 3D nanostructure (211), (FIG. 55), followed by a step of assembling said resorbable polymer matrix (210) comprising at least one negative mould of said at least one 3D nanostructure (211) with a support consisting of a non-resorbable membrane (1) comprising at least one perforation (4), such that at least one negative mould of said at least one 3D nanostructure (211) is aligned with said at least one perforation (4) of said support (1), (FIG. 57), followed by a step of applying at least one continuous layer of at least one polyelectrolyte on the continuous surface formed by the lower face (3) of said support (1) and the lower face (212) of said resorbable polymer matrix (210) comprising at least one negative mould of said at least one 3D nanostructure (211) at the perforations (4) of said support (1), to consist of a 3D nanostructured porous membrane (5) comprising at least one protuberance (8) (FIG. 58), followed by a step of dissolving said resorbable polymer matrix (210) (FIG. 59).

Figure 62:
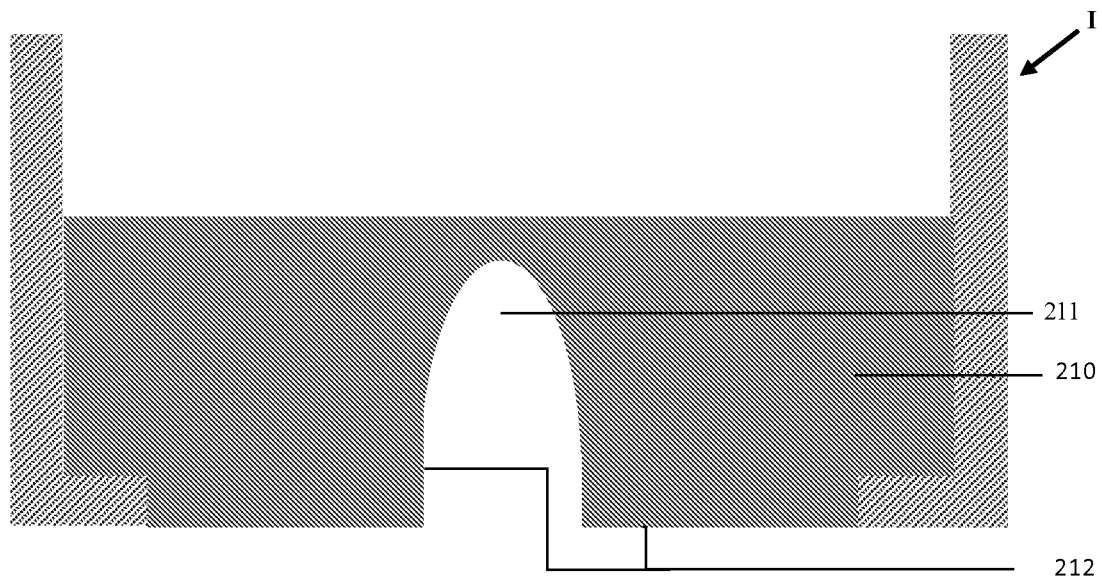
Figure 63:
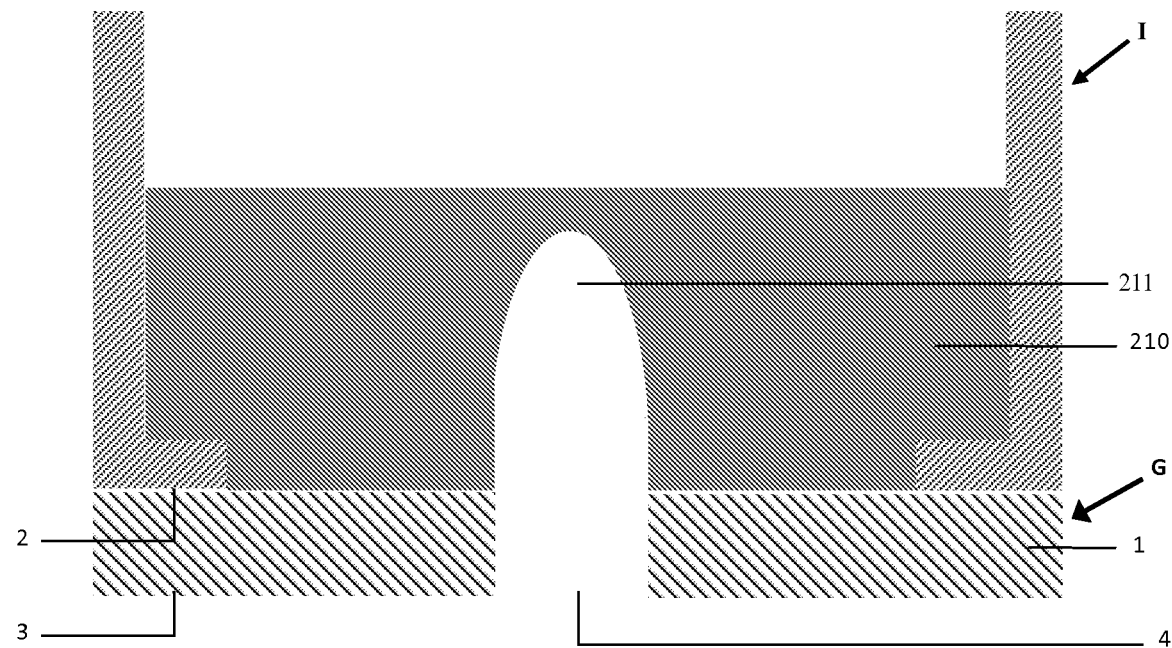
Figure 65:
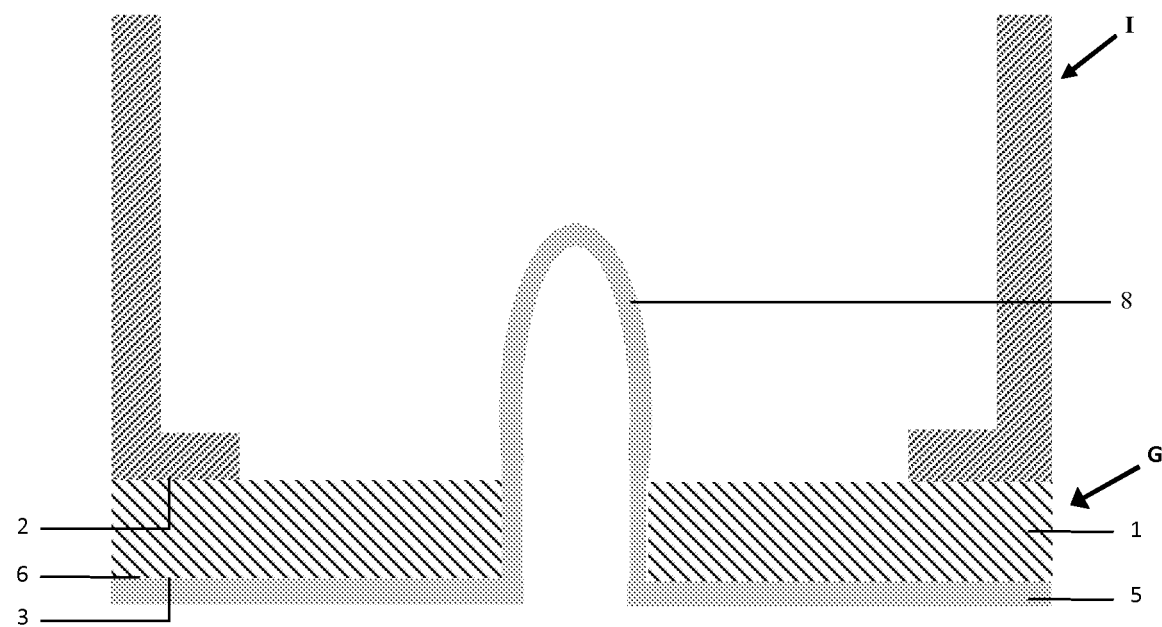
Figure 66:
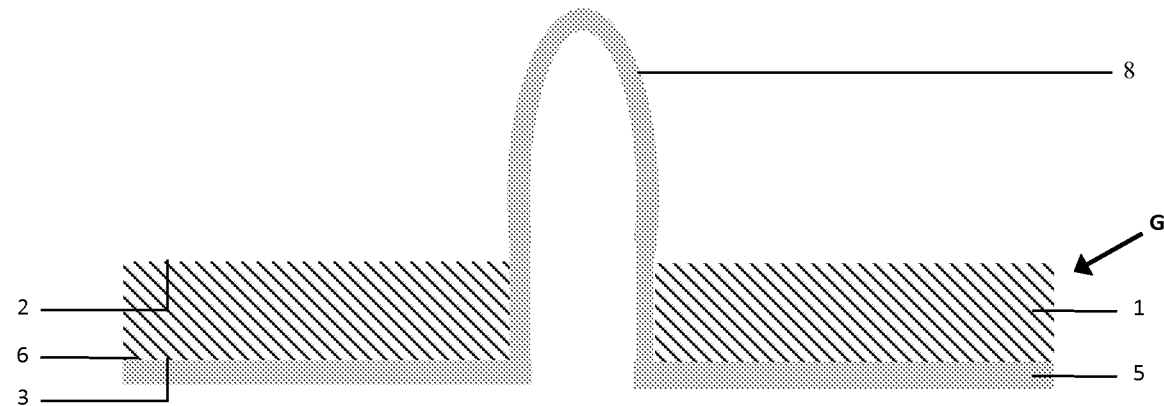

The invention also relates to an alternative process for producing a microfluidic cell culture chip according to the invention, wherein the production of the central module comprising the central unit, comprises:

(i) a step of assembling a support part (I, i), consisting of a side frame (213), an open upper face (214) and a solid lower face (215) comprising a cut (216) at the format of the central unit, and a mould (H, H1, H2, h1, h2), in the shapes and dimensions of said support part (I, i), comprising at least one moulded 3D nanostructure (208) on the upper face (209), said mould being, in particular, made of plastic (FIG. 60), (ii) a step of pouring a resorbable polymer solution (22) on said upper face (209) of said mould (H, H1, H2, h1, h2), (FIG. 61), followed by (iii) a step of polymerising said resorbable polymer solution (22) to make rigid said resorbable polymer solution and form a resorbable polymer matrix (210) comprising at least one negative mould of said at least one 3D nanostructure (211), followed by (iv) a step of removing said mould (H, H1, H2, h1, h2), to obtain said resorbable polymer matrix (210) comprising at least one negative mould of said at least one 3D nanostructure (211) formed in said cut (216) of the solid lower face (215) of said support part (I, i), (FIG. 62), followed by (v) a step of assembling said support part (I, i), with a perforated part (G, G1, G2, g1, g2), comprising a support consisting of a non-resorbable membrane (1) perforated by at least one perforation (4) integrated in a base (106), (FIG. 63)

said perforated part (G, G1, G2, g1, g2) being in the shapes and dimensions of said support part (I, i), and the number of perforations (4) of said perforated part (G, G1, G2, g1, g2) being identical to the number of moulded 3D nanostructures (211) in said mould (H, H1, H2, h1, h2) used in step (i), such that said at least one perforation (4) of said support (1), that is aligned with said at least one negative mould of said at least one 3D nanostructure (211), followed by (vi) a step of applying at least one continuous layer of at least one polyelectrolyte on the continuous surface consisting of the lower face (3) of said support (1) and of the lower face (212) of said resorbable polymer matrix (210) comprising at least one negative mould of said at least one 3D nanostructure (211), at the said at least one perforation (4) of said support (1), to consist of a 3D nanostructured porous membrane (5) comprising at least one protuberance (8) (FIG. 64), followed by (vii) a step of dissolving said resorbable polymer matrix (210) comprising at least one negative mould of said at least one 3D nanostructure (211), (FIG. 65), (viii) a step of removing the support part (I, i) to obtain said perforated part (G, G1, G2, g1, g2) comprising, on the lower face (3) thereof, a 3D nanostructured porous membrane (5), and on the side of the upper face thereof, said at least one protuberance (FIG. 66).

Figure 69:
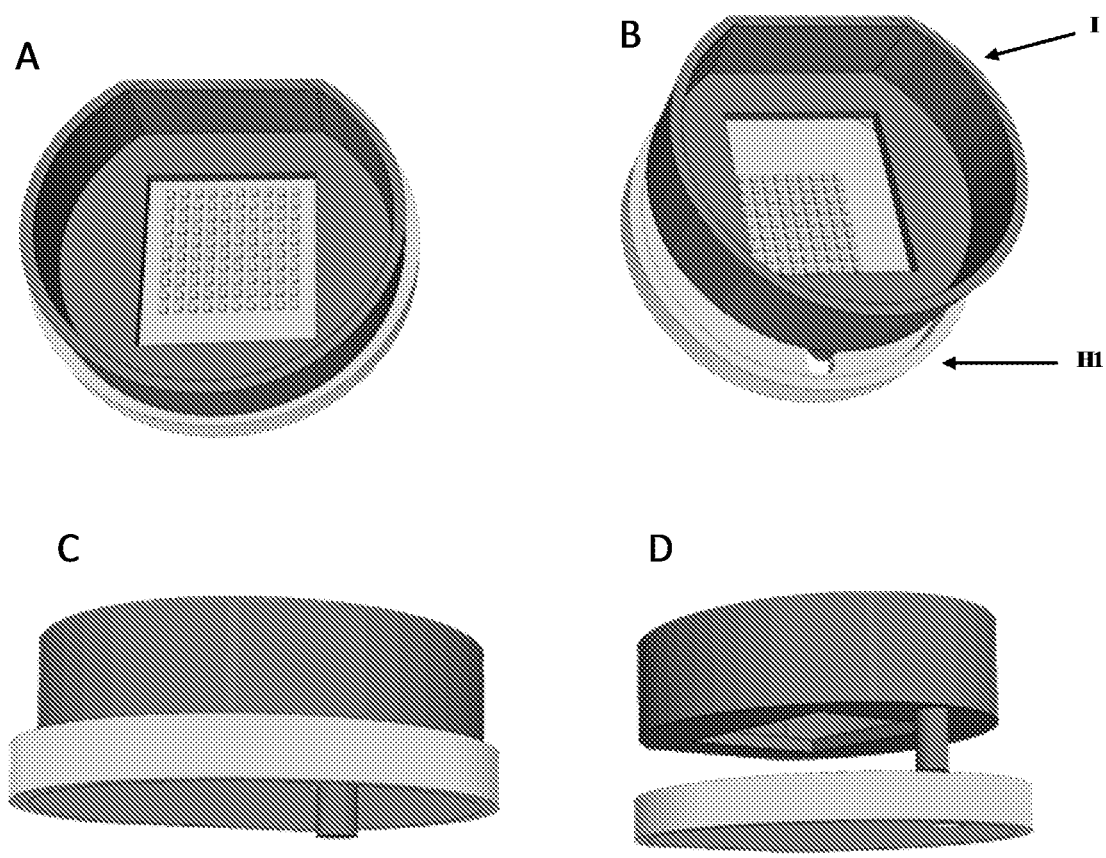

As shown in FIG. 69, step (i) of the process described above, corresponds to the assembly of the support part I with the mould H, in particular a mould H1 comprising 100 moulded 3D nanostructures (208), in a reproducible and specific alignment which is guided by the flat section of the parts and the pin for aligning (217) the support part I which is inserted in the hole for aligning (218) the mould H1.

For the assembly of the support part I and the mould H, the solid face (215) of said support part I is placed on the upper face (209) of the mould H, such that the moulded 3D nanostructures (208) of said mould H are positioned at the cut (216) of said solid face of the support part I.

The chamber thus formed by the connection of the mould H with the support part I is then filled with the resorbable polymer (22) according to step (ii).

After polymerisation of the resorbable polymer (step iii), a resorbable polymer matrix (210) comprising at least one negative mould of said at least one 3D nanostructure (211) is formed in the cut (216) on the solid face (215) of the support part I.

The mould H is then removed from the support part I according to step (iv). The base of the support part I is thus formed at the cut (216) by a resorbable polymer matrix (210) comprising at least one negative mould of at least one 3D nanostructure (211).

Figure 70:
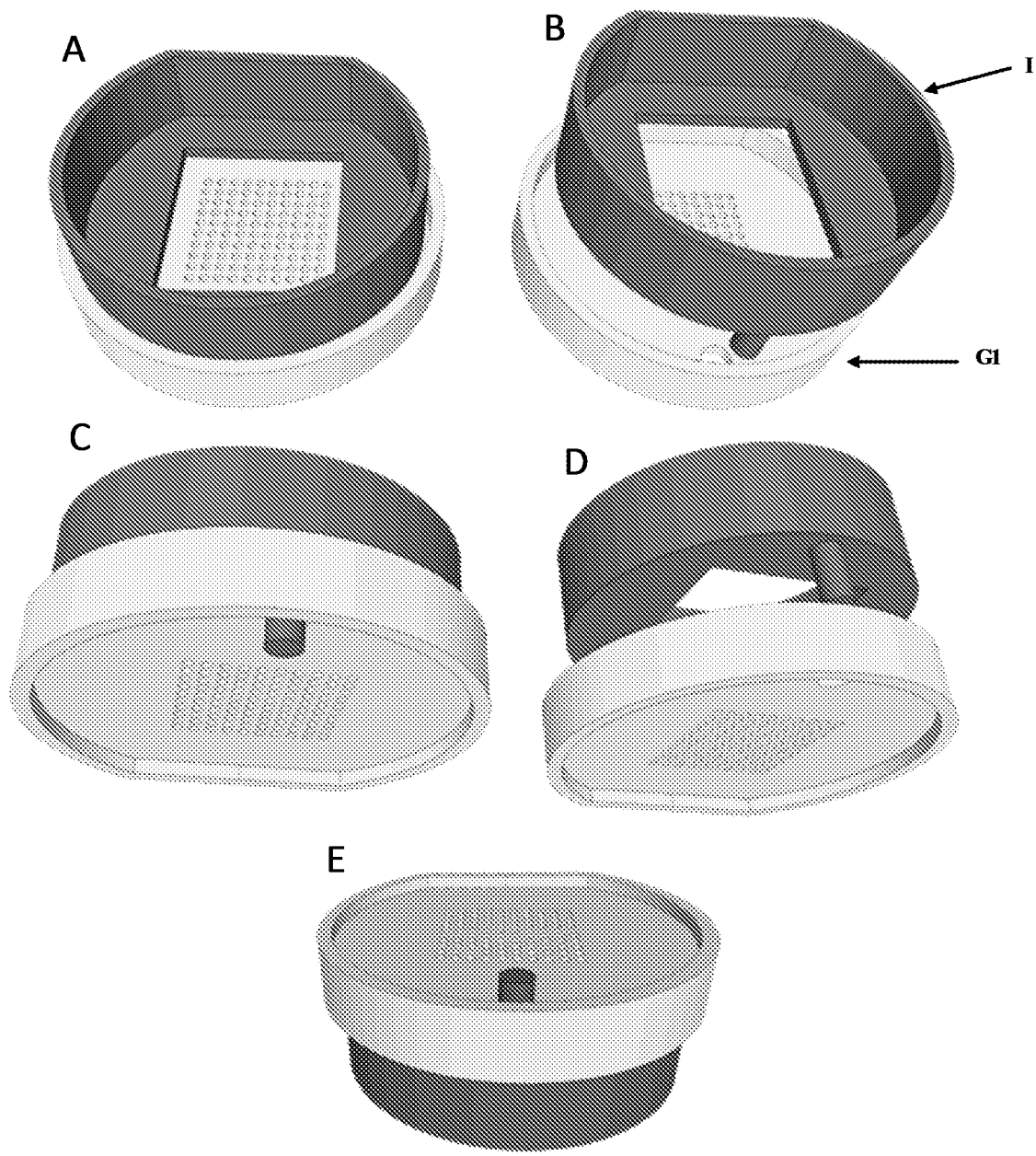

The support part I is then assembled with the perforated part G, in particular a perforated part G1 comprising 100 perforations (4), according to step (v), in a reproducible and specific alignment which is guided by the flat section of the parts and the pin for aligning (217) the support part I which is inserted in the hole for aligning (218) the perforated part G (FIG. 70).

The perforated part G consists of a support (1) comprising at least one perforation (4), said support (1) being inserted in a base (106).

Selecting the perforated part (G1, G2, g1, g2) depends on the selection of the mould (H1, H2, h1, h2) in step (i), the shape and number of 3D nanostructures of the mould (H1, H2, h1, h2) having to be identical to the shape and to the number of perforations of the perforated part (G1, G2, g1, g2) (FIGS. 67, 68, 72, 73).

The upper face (2) of the support (1) of the perforated part G is positioned in contact with the lower face (212) of said resorbable polymer matrix (210).

The perforations (4) of the perforated part G are thus aligned with the negative moulds of the 3D nanostructures (211) of said matrix (210) using the pin for aligning (217) the support part I which is triggered in the hole for aligning (218) the perforated part G.

The parts I and G1 assembled are then returned as shown in FIG. 70-E, so as to have the part G1 above the support part I.

The walls of the perforations of the part G1 make it possible for the formation of a chamber, so as to facilitate the formation of the protuberances (8) by applying at least one continuous layer of at least one polyelectrolyte according to step (vi), on the continuous surface formed by the lower face (3) of the support (1) and the lower face (212) of said resorbable polymer matrix (210) comprising at least one negative mould of said at least one 3D nanostructure (211), at the perforations (4) of said support (1).

Once the at least one protuberance (8) is formed, the resorbable polymer forming said matrix (210) of negative moulds (211) is dissolved according to step (vii).

The support part I is thus removed from the perforated part G1.

The perforated part G1 thus comprises, on the side of the lower face (3) of the support (1), a 3D nanostructured porous membrane (5), and on the side of the upper face (2) of the support (1), said at least one protuberance in the extension of said at least one perforation of the support of the perforated part G1, (FIG. 66).

In this embodiment, the upper face (6) of the 3D nanostructured porous membrane (5) is secured (in contact) with the lower face (5) of the support consisting of a non-resorbable membrane (1).

This perforated part G1 thus obtained comprising a support (1) with the perforations (4) and the 3D nanostructured membrane (5) comprising protuberances (8), consists of the central module of the microfluidic chip and is used for the culture of cells of each side of said at least one protuberance.

DETAILED DESCRIPTION

Examples of Circular-Shaped Parts I, H and G

According to a specific embodiment, said support part (I), said mould (H1, H2) and said perforated part (G1, G2) are circular-shaped, making it possible in particular to be adapted to the cell culture boxes with a diameter of 35 mm.

Figure 67:
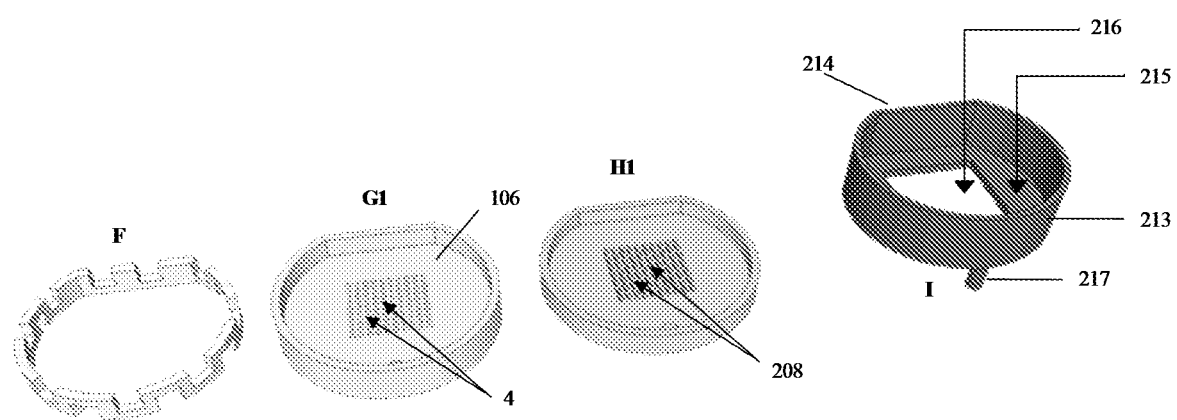

FIG. 67 presents a specific embodiment of the process wherein said mould (H1) and said perforated part (G1) respectively comprise 100 moulded 3D nanostructures and 100 perforations.

Such a process makes it possible to obtain a central unit with 100 protuberances.

Figure 68:
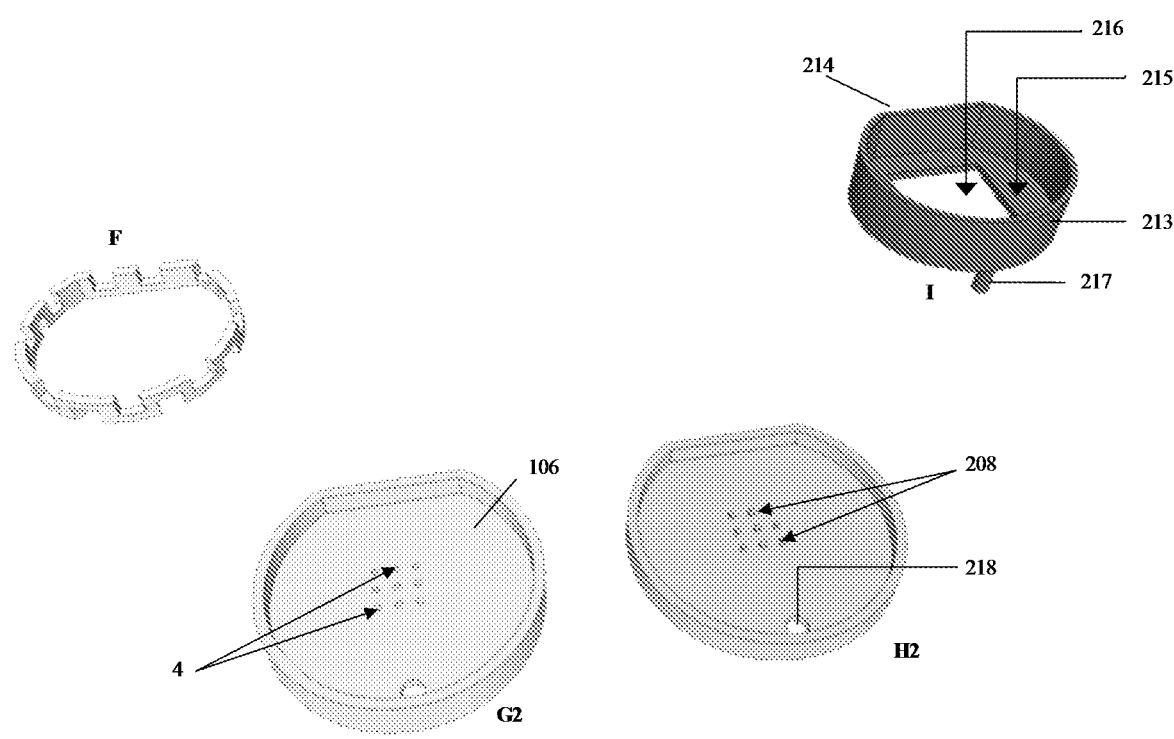

FIG. 68 presents a specific embodiment of the process wherein said mould (H2) and said perforated part (G2) respectively comprise 9 moulded 3D nanostructures and 9 perforations.

Such a process makes it possible to obtain a central unit with 9 protuberances.

These examples of numbers of perforations and moulded 3D nanostructures, are not limiting.

Selecting the mould and the perforated part depends on the desired number of protuberances for the 3D nanostructured membrane of the central unit.

Figure 71:
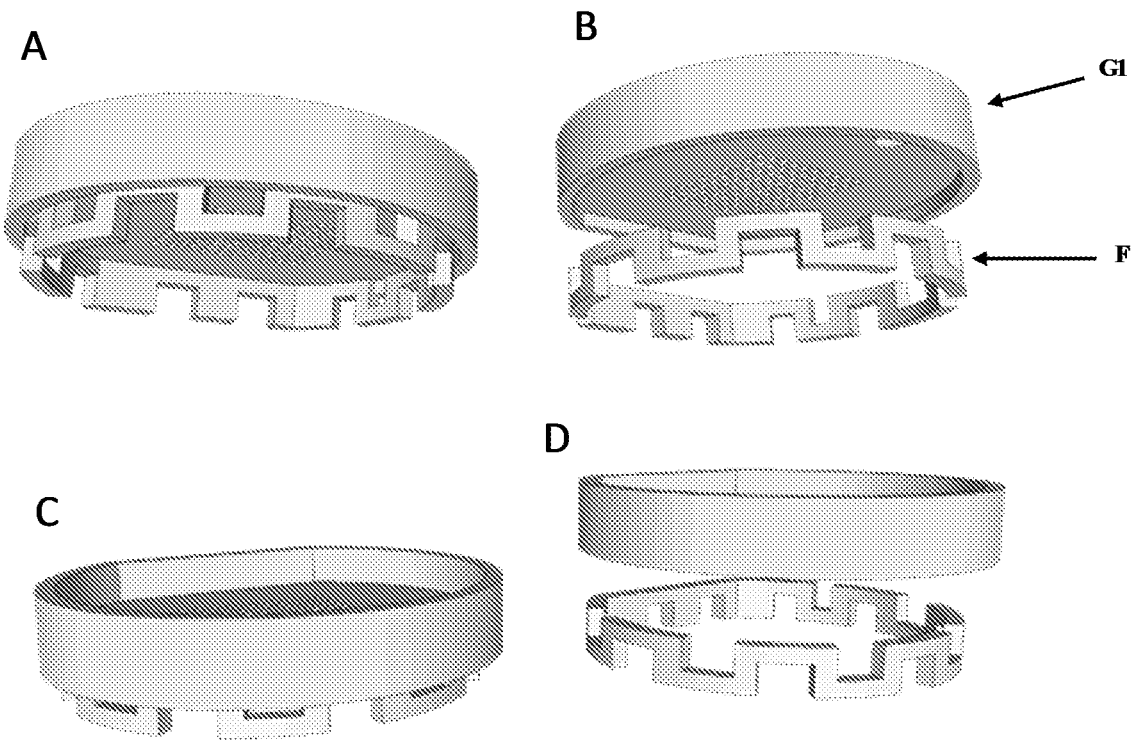

In this specific embodiment, the central module consisting of the perforated part G with the protuberances obtained from the process detailed above, can be placed on a cell culture chamber, such as a cell culture box with a diameter of 35 mm containing the culture medium, by way of a part F, as shown in FIG. 71.

According to an embodiment of the invention, the central module obtained by the process described above, is placed on a lower module such as described in the present invention, comprising at least one duct to collect secretions from the at least one protuberance.

The lower module is of identical shape and identical dimensions to said central module.

The lower module is assembled to the central module in a reproducible and specific alignment which is guided by the flat section of the parts and the pin for aligning the part of the lower module which is inserted in the hole for aligning the central module.

The lower module comprises a number of ducts, identical to the number of perforations, and therefore protuberances of the central module, such that the assembly of said central module with said lower module makes it possible to align the ducts with the perforations and therefore the protuberances, to collect the secretions from the cells via a microfluidic system.

In this other specific embodiment according to the invention, the lower module is replaced by the part F. This part F, used as a support of the central module on the culture box such as represented in FIGS. 67, 68 and 71 comprises square openings making it possible for the circulation of the culture medium to give nutrients to the growth cells on the inner face of said at least one protuberance.

Examples of Square-Shaped Parts I, H and G

According to a specific embodiment, said support part (i), said mould (h1, h2) and said perforated part (g1, g2) are square-shaped.

Figure 72:
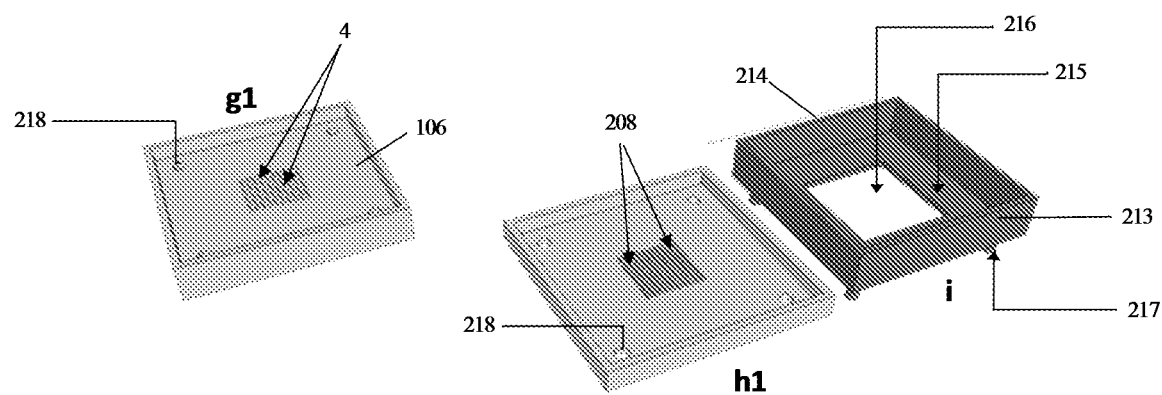

FIG. 72 presents a specific embodiment of the process wherein said mould (h1) and said perforated part (g1) respectively comprise 100 moulded 3D nanostructures and 100 perforations.

Such a process makes it possible to obtain a central unit with 100 protuberances.

Figure 73:
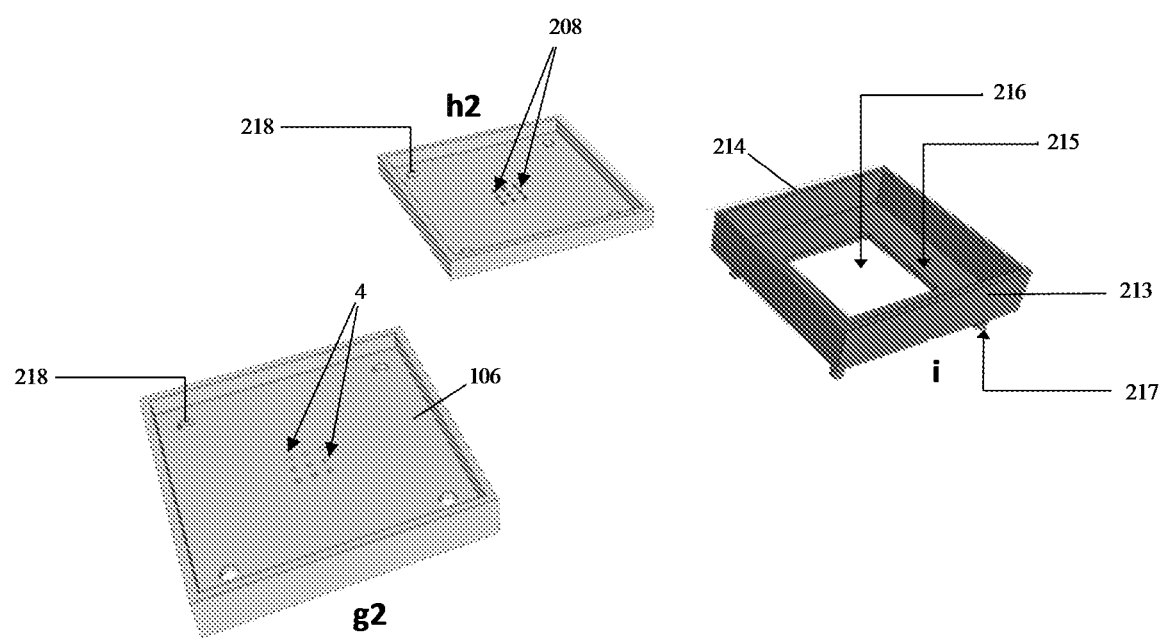

FIG. 73 presents a specific embodiment of the process wherein said mould (h2) and said perforated part (g2) respectively comprise 9 moulded 3D nanostructures and 9 perforations.

Such a process makes it possible to obtain a central unit with 9 protuberances.

These examples of numbers of perforations and moulded 3D nanostructures, are not limiting.

Selecting the mould and the perforated part depends on the desired number of protuberances for the 3D nanostructured membrane of the central unit.

The resorbable polymeric solution is preferably made with chitosan, agarose or alginate.

According to a specific embodiment, the invention relates to a process for producing a microfluidic cell culture chip, wherein said resorbable polymer solution (22) is chitosan.

When chitosan is used, the resorbable mould can be prepared by dissolving 2% chitosan in 2% acetic acid for one night, then by diluting 1.5% chitosan with ethanol. The chitosan solution is then polymerised in a 5M hot bath of NaOH: ethanol at a ratio 1:1.

According to a specific embodiment, the invention relates to a process for producing a microfluidic cell culture chip, wherein the step of polymerising said resorbable polymer solution (22), said resorbable polymer solution (22) being chitosan, is made by an incubation with a 2% acetic acid solution.

When chitosan is used as a resorbable polymeric material, the dissolution is done by an incubation overnight with a 2% acetic acid solution, according to a protocol that is well known to a person skilled in the art.

According to a specific embodiment, the invention relates to a process for producing a microfluidic cell culture chip, wherein said resorbable polymer solution (22) is agarose.

When agarose is used, the resorbable mould can be prepared by heating and by dissolving 40 µg/ml of agarose in PBS (phosphate buffered saline). Agarose is polymerised by placing the solution obtained at a temperature below the gelation point thereof.

According to a specific embodiment, the invention relates to a process for producing a microfluidic cell culture chip, wherein the step of polymerising said resorbable polymer solution (22), said resorbable polymer solution (22) being agarose, is carried out by an incubation at a temperature greater than the gelation temperature of agarose.

When agarose is used as a resorbable polymeric material, the dissolution is done by a slow heating from ambient temperature to a temperature of 70° C., for 120 minutes, then by letting the temperature of the agarose return to ambient temperature over one night.

This heating can be done in a water bath. It is important that the temperature slowly increases to minimise thermal convection currents which could damage the 3D nanostructured porous membrane.

Variants of this heating protocol, well known to a person skilled in the art, include the addition of DMSO in the water of the water bath to modify the gelation properties of agarose.

According to a specific embodiment, the invention relates to a process for producing a microfluidic cell culture chip, wherein said resorbable polymer solution (22) is alginate.

According to a specific embodiment, the invention relates to a process for producing a microfluidic cell culture chip, wherein the step of polymerising said resorbable polymer solution, said resorbable polymer solution (22) being alginate, is carried out by an incubation overnight with a solution with no $Ca^{2+}$ a $Ca^{2+}$ ion binding agent added, such as EDTA or EGTA.

The polyelectrolyte multilayer film comprises, as variable parameters:
the number of layers,
the thickness of each of the layers,
the charge of the polyelectrolyte(s) used.

By varying the number of layers, the roughness, the thickness and the rigidity of the final multilayer film can be modified.

Preferably, the film is composed of 15 layers, 2 nm thick, of polyelectrolytes.

By varying the number of layers or the type of charge for the polyelectrolytes used, the hydrophobicity of the final multilayer film can also be modified.

The extrusion of the 3D nanostructure can be subject to the following defects, due to the pumping system used for the extrusion:

translation defect, when there is a translation of the protuberance with respect to leaving the site provided, directly aligned with the perforation of the support, extrusion defect, when there are defects in the shape of the protuberance, like for example a thickening of the base or other defects which will be known to a person skilled in the art.

A protuberance thus formed from 3D nanostructures with a translation defect or an extrusion defect can continue exercising the technical function thereof provided initially within the device, however, as the protuberance thus formed has a less optimal shape, the performance thereof within the device is also less optimal. However, the device can continue to exercise the function thereof provided, but with a reduced performance.

The protuberance can have different changes such as:

a tilt with respect to an axis (y), passing through the centre of said opening and which is perpendicular to said support, a variation of the height thereof, a translation with respect to the perforation, due to the translation of the 3D nanostructured porous membrane on the support.

These changes are due to the process for preparing the central module, and in particular at the phase of extruding the polymeric solution through the perforations of said support.

Certain changes are also driven directly during the use of the protuberance in the device.

I—Example of Using the Chip for a Co-Culture

1. Conditions for Maintaining Line Cultures of Prostate Epithelial Cells and Stromal Cells The culture medium used for all experiments is a Keratinocyte Serum Free Medium (KSFM) (Life Technologies, Carlsbad, CA, Ref. 17005-075) supplemented by 5 ng/mL of epidermal growth factor (EGF) and 50 µg/mL of bovine pituitary extract.

The lines of prostate epithelial cells and stromal cells are maintained in the medium are cultured in an atmosphere at 37° C. and 5% $CO_2$.

The subculturing of the cells in a fresh medium is done every three days for epithelial cells and every two days for stromal cells. For this, the cells are washed with a phosphate buffered saline solution from Dulbecco (D-PBS) without calcium and without magnesium (Life Technologies, Ref. 14190), then incubated with 1 mL of Trypsine-EDTA at 0.25 mg/mL, at 37° C., (Lonza, Basel, CH, Ref. CC-5012) for around 7 minutes.

For all experiments, the culture medium of the cells has been supplemented each day with the fresh culture medium.

2. Preparing Cells Before the Introduction in the Central Unit

A chemical separation of the cells is done by an incubation of 5 minutes at 37° C. with 1 ml of trypsin-EDTA at 0.25 mg/ml (Life Technologies, Ref. 25300-054) in the PBS medium without calcium and without magnesium.

Independently, a microfluidic chip according to the invention is sterilised by making a 70% ethanol (volume/volume) solution circulate through the ducts, then by drying all of the microfluidic system in a furnace at a temperature of between 35° C. and 45° C. for at least 30 minutes, then by exposing it to a U.V. radiation, and to ozone for 40 minutes.

3. Preparing the 3D Nanostructured Porous Membrane of the Central Unit

The 3D nanostructured porous membrane consists of successive layers of polyelectrolytes alternating a positively charged polyelectrolyte layer and a negatively charged polyelectrolyte layer. According to the production process, this same membrane consists of protuberances.

The outer face and the inner face of the protuberances, consisting of the polyelectrolyte porous membrane, are covered by an extracellular matrix (ECM) preparation composed of Matrigel® and/or collagen, fibronectin or hyaluronic acid.

The Matrigel® matrix used here is a commercial product produced by the company Corning@.

It is a reconstituted basal membrane preparation, which is extracted from Engelbreth-Holm-Swarm (EHS) mouse sarcoma, a tumour rich in extracellular matrix proteins. Once isolated, this material is composed of around 60% laminin, 30% collagen IV, and 8% entactin. Entactin is a bridging molecule which interacts with laminin and collagen IV, and contributes to the structural organisation of these molecules of the extracellular matrix.

The Matrigel® matrix from Corning® also contains heparan sulphate proteoglycans (perlecan), of transforming growth factor β (TGF-β), of epidermal growth factor, of insulin type growth factor, of fibroblast growth factor, a plasminogen tissue activator and other growth factors which are naturally present in the EHS tumour. It also contains residual matrix metalloproteinases derived from tumour cells.

Matrigel® can be used by itself to functionalise the porous membrane, at a concentration of 6 mg/ml, or as a mixture with type I collagen at a concentration of between 0.75 and 2.5 mg/ml.

4. Introducing Two Cell and Cell Co-Culture Types in the Central Unit 4.1. Introduction of Epithelial Cells Initially, the epithelial cells are introduced to form a cell joining layer, i.e. a cell culture at the stage of the confluence.

According to a specific embodiment, the epithelial cells are introduced on the inner faces of the protuberances of the central unit.

Three hours are required to obtain the adhesion of the cells, and 24 hours for the formation of a layer for joining cells, i.e. at a stage of cell confluence. These adherent and proliferative cells secrete their own extracellular matrix and thus establish a basal layer playing the role of a barrier.

The inner face of the protuberances of the central unit is thus covered by a dense single layer of epithelial cells, which is used as a physiological support for the growth and differentiation of human cells, isolated from the patient's urine.

The introduction of cells on the inner face of the protuberances can be done, according to 3 methods:

returning the central module in order to have the lower sections of the perforations towards the top and manually pipette a cell suspension.

returning the central module in order to have the lower sections of the perforations towards the top and use a robot for handling fluids to introduce a cell suspension.

assembling the upper module, the central module and the lower module, and fill the central unit on the side of the inner face of the protuberances using microfluidic ducts of the lower unit. In the case of this pre-assembly of the three modules, the cells are therefore introduced via the ducts of the lower module. This method of introducing cells after a pre-assembly of the three modules is preferred to the two other methods, as it prevents any bacterial contamination, because the previously sterilised system is kept closed.

According to a specific embodiment, the epithelial cells are introduced at a concentration of $3.10^6$ cells/mL in the central unit, either directly via the perforations ($1^{st}$ and $2^{nd}$ method) with a syringe, or via the ducts of the lower unit ($3^{rd}$ method) by using a fluid system, automated and controlled by pressure and flow (Fluigent) or a syringe pump.

Using a syringe pump with an adjustable flow is preferred, in order to provide a smooth and controlled introduction of cells.

A stable and continuous flow is delivered by using pressure pumps (Fluigent, France). Pressurised containers containing the culture medium are kept in a chamber at a controlled temperature and $CO_2$ level. The flow is adjusted to around 5-10 mL/hour (10 mbar) and the adhesion and the proliferation of the cells is observed over time. All the samples are kept in an incubator, humidified at 37° C. and 5% $CO_2$.

In a specific embodiment, the central unit comprises protuberances of a height of 350 μm with a circular base of 150 μm in diameter. The area of the inner surface of the protuberance is thus 329700 μm$^2$, on which around 50 epithelial cells are counted at the confluence stage (joining cell layer), that is around one cell every 66 μm$^2$.

4.2. Introduction of Cells on the Outer Face of the Protuberances

Secondly, once the layer of joining (or confluent) epithelial cells formed on the inner face of the protuberances, the stromal cells are dispensed on the porous membrane at the outer and inner faces of the protuberances.

The introduction of cells on the inner face of the protuberances can be done according to two methods:
- returning the central module in order to have the tops of the protuberances towards the top and manually pipette a cell suspension.
- assembling the upper module, the central module and the lower module and fill the central unit on the side of the inner face of the protuberances using the microfluidic ducts of the lower unit. In the case of this pre-assembly of the three modules, the cells are therefore introduced via the inlet/outlet ducts of the upper unit. This method of introducing cells after a pre-assembly of the three modules, is preferred to the other methods, as it prevents any bacterial contamination because the previously sterilised system is kept closed.

According to a specific embodiment, the stromal cells are introduced via the inlet/outlet ducts of the upper module at a concentration of $3.10^6$ cells/mL in the central unit directly using a syringe ($1^{st}$ method), that is via the ducts of the upper module ($2^{nd}$ method) by using a fluid system, automated and controlled by pressure and flow (Fluigent) or a syringe pump.

The stromal cells adhere very quickly (less than one hour).

It is not necessary that the stromal cells form a layer of confluent (or joining) cells, the simple adhesion thereof on the outer face in this example is enough.

Generally, the ratio between the epithelial cells and the stromal cells is 1:2.

Thus, according to a specific embodiment, for a co-culture on a surface of 0.7 cm$^2$, the porous membrane at the outer and inner faces of the protuberances is functionalised with 90 μl of a Matrigel® solution diluted to 6 mg/ml, then seeded to obtain, in the end, 7000 epithelial cells/cm$^2$ and 14000 stromal cells (fibroblasts)/cm$^2$.

The culture medium, introduced via the inlet/outlet ducts of the upper module and via the ducts of the lower module to supply the cell cultures, is identical on either side of the protuberances, and consists of the KSFM culture medium supplemented by 5 ng/mL of epidermal growth factor (EGF) and by 50 μg/mL of bovine pituitary extract.

4.3. Examples of Epithelial Cells and Stromal Cells

These epithelial cells can be non-tumorigenic commercial cell lines (prostate or bladder or kidney) or commercial primary cultures.

These stromal cells can be:
- either fibroblasts (commercial primary cultures or lines),
- or mesenchymal cells (commercial cultures or lines),
- or other stromal cells (endothelial, etc.).

The two cell types used to form these cellular single layers, are called "neutral" or "healthy", they are non-tumorigenic and only play the role of a basal layer. These "neutral" cells form, at the stage of the confluence, a highly contiguous layer of cells on the inner and outer face of the protuberances, establishing tight seals, that it is possible to characterise by immunofluorescence and imaging (see E-cadherin part 5 marking).

4.4. Interchangeability of Cultures on the Inner and Outer Faces of the Protuberances According to a specific embodiment, the epithelial cells are introduced on the inner face of the protuberances and the stromal cells are introduced on the outer face of the protuberances.

However, the co-culture can be established in an interchangeable manner, i.e. the stromal cells can also be introduced on the inner face of the protuberances, and the epithelial cells on the outer face of the protuberances. In both cases, the polyelectrolyte layer located between the two cell types, makes it possible to constitute a porous barrier, using the positively and negatively charged polyelectrolyte mesh thereof.

5. Visualisation of the Cells in the Central Unit (Proof of Concept of the Co-Culture on the Protuberances)

In order to validate the method of co-culture on the protuberances of the central unit, an immunomarking is carried out.

This immunomarking is therefore carried out on dead cells (attached by PFA) and this visualisation has the sole aim of controlling the co-culture being correctly in place, and that the methodology of introducing cells in correct.

The cells are visualised in the central module by immunomarking.

Phalloidin is used to identify cortical actin filaments, which follow the edges of the plasma membrane and, consequently provide a means to delimit the extent of the cell and the membrane thereof.

E-cadherin is used to detect the cell-cell junctions.

Immunostaining is carried out by introducing E-cadherin with a syringe pump via the ducts at ambient temperature.

After the formation of a confluent layer of epithelial cells, around 24 hours after the introduction thereof, they are attached for 20 minutes with 4% Perfluoroalkoxy (PFA) (volume to volume) in a solution composed of 10% sucrose in a cytoskeleton buffer (solution A).

The cells are then washed with solution A and permeabilised for 3 minutes with a solution A added with 0.1% Triton TX-100. A washing with a TBS solution is carried out for 10 minutes, followed by a second washing with a PBS solution for 30 minutes. The autofluorescence of the PFA is inactivated by the NH$_4$Cl contained in the TBS solution. The non-specific sites are blocked by an incubation with a PBS solution with 10% goat serum and 3% BSA. The cells are then incubated with a primary antibody for one hour. The primary antibody used is an anti-E-cadherin antibody (Abcam, Ref. ab1416) diluted to 1/50 in a PBS solution with 0.1% Tween-20 and 1% BSA. The cultures are then washed for 30 minutes with a PBS solution, then incubated with a secondary anti-mouse antibody coupled with the cytochrome Cy3 (Jackson, Ref. 115-162-062), diluted to 1/1000 of Phalloidin FITC (Sigma, Ref. P5282) diluted to 1:1000 in a PBS solution with 0.1% Tween-20 and 1% BSA, for 20 minutes.

After a washing of 30 minutes with a PBS solution, the rings are counter-stained with Hoechst colourant (Life Technologies, Ref. H-1399), diluted to 1:7000, for 5 minutes. The cells are then washed for 10 minutes and the Dako fluorescent medium is manually introduced.

The binding focal points have been detected by marking by using Vinculine. For counter-marking with Vinculine, the cells are pre-permeabilised for 40 seconds with Triton X-100 and attached with a PBS solution with 4% PFA (v/v), for 20 minutes, then washed once with a PBS solution.

To avoid any non-specific antibody adsorption, the cells are incubated with a 0.1% BSA and 10% goat serum solution for one hour.

The cells are then incubated for one hour with a primary antibody directed against Vinculine (Sigma, Ref. V9131) diluted to 1:700 in a PBS solution with 0.05% Tween 20 and 5% goat serum, then washed 4 consecutive times for 45 minutes with a PBS Solution The cells are then incubated with an anti-mouse antibody, coupled with the cytochrome Cy5, diluted to 1/500 in a PBS solution with 0.05% Tween 20 and with 5% goat serum (Jackson).

The central module is then washed 4 times for 15 minutes with a PBS solutions. The rings and the actin are stained as described above.

The co-culture is observed by fluorescence microscopy or can be observed by other microscopy methods such as phase contrast microscopy, lensless imaging, confocal microscopy, light sheet microscopy.

The images are captured during the cell culture.

To provide a view of the whole of the total width of the device, cell images are recorded using a lensless sensor. SEM analyses are also carried out.

In a specific embodiment, the fluorescence images of the central module containing the co-culture of cells, are obtained using a Zeiss AxioImager Z1 microscope with a 20× lens equipped with the right Apotome module for acquisitions with a z-stack field depth, with the shot every 3 mm in the axis z, for a tube, 150 mm in diameter. The images are recorded using a digital AxioCam MRm digital camera mounted on the microscope.

6. Visualisation of the Cells in the Central Unit in Real Time

The cell cultures in the central unit can be monitored in real time by a phase contract microscope observation which makes it possible to visualise the non-marked and living cells, because of the transparency of the materials consisting of the modules.

II—Example of Using the Chip for the Diagnosis

1. Introduction of Cells Coming from the Patient

According to a specific embodiment, the epithelial cells are introduced on the inner face of the protuberances and the stromal cells are introduced on the outer face of the protuberances.

Once a single layer of cells obtained on each of the faces, that is after 24 hours, the microfluidic chip, thus provided with cells, can be used for the diagnosis of a patient.

For this, the cells are isolated from a urine sample of a patient of at least 50 ml, in particular from 50 to 100 ml. The isolation is done by centrifuging the urine sample at a low speed, in particular 800 g for 5 minutes, making it possible for the sedimentation of the cells contained in the urine sample. This centrifugation step is well known to a person skilled in the art.

The lower part of sedimented cells is then resuspended in the culture medium and the cell suspension is directly introduced in the microfluidic chip according to the invention, which means that the cells do not require any pre-culture before the introduction thereof in the chip.

The concentration of the cells obtained from the urine sample is or varies by a few hundred cells to several thousand.

The isolated urine cells of the patient can be introduced on the side of the face of the protuberance which supports the culture of epithelial cells, or on the side of the face of the protuberance which supports the culture of stromal cells. In other words, these cultures, being interchangeable on either side of the protuberance, the isolated cells of the urine of the patient can be introduced both on the inner face, and on the outer face of the protuberances.

According to a specific embodiment, the isolated cells of the urine of the patient are introduced on the side of the face of the protuberance which supports the culture of epithelial cells. Thus, they are introduced via the ducts of the lower unit, when the single layer of epithelial cells is formed on the side of the inner face of the protuberances, that is via the inlet/outlet ducts of the upper module when the single layer of epithelial cells is formed on the side of the outer face of the protuberances.

The cells isolated from the urine of the patient are exfoliated uroepithelial (or urothelial) cells, including all bladder, prostate and kidney epithelial cells.

In a specific embodiment, the inner face of the protuberances is covered by a layer, pre-formed of previously cultured epithelial cells, the outer face of the protuberances is covered by a layer, pre-formed of fibroblasts (stromal cells), and the isolated cells are dispensed via the ducts of the lower module.

These isolated cells are inserted in this layer, pre-formed of healthy epithelial cells on the side of the inner face of the protuberances, and which is supported by a layer of healthy fibroblasts.

2. Observation of the Proliferation of Cells Coming from the Patient

The proliferation of isolated cells is thus monitored, in order to observe the progression of the proliferation of the isolated cells in the device and to examine if this proliferation results in replacing healthy basal cells and affects the overall secretory profile of the tissue.

3. Recovery of Secretions

Once the introduction of cells isolated from the urine of the patient is done, the epithelial cells of patients are stimulated by adding 0.1 ng/ml of DHT (Dihydrotestosterone) on the outer or inner face of the protuberance. This stimulation of cells by DHT lasts between 24 hours and 48 hours.

The membrane consisting of the outer and inner faces of the protuberances being porous, this stimulation can be made equally on either side of the protuberances.

The epithelial cells can also be stimulated by adding mibolerone (non-metabolised hormone).

The stimulation of the epithelial cells is thus, made after the binding of two cell types on either side of the protuberances, and after the growth thereof until the confluence stage.

The secretions can be recovered when the isolated cells of the patient bind and are inserted in this layer, pre-formed of healthy epithelial cells on the side of the inner face of the protuberances, and which is supported by a layer of healthy fibroblasts on the side of the outer face of the protuberances. The binding of the isolated cells of the patients lasts around 3 hours and the integration thereof lasts around 6 hours.

The accumulation of a sufficient volume of secretions progressively occurs.

The final recovery of the secretions for the analysis of secretome is carried out after having left at least 12 hours pass.

More specifically, the secretions are recovered at the end of the 24 to 48 hours of stimulation with DHT.

They are then analysed by a device making it possible for the analysis of compounds in the solution. According to a specific embodiment, the secretome is analysed by mass spectrometry.

The secretions can be analysed in line by sensors incorporated in said chip.

It must be noted, that the different modules composing said chip are not affected when the secretions are recovered or when the secretions are continuously analysed by the sensors in line.

Searching for specific markers by immunological methods can also be done in the recovered secretions.

For example, the detection of PSA (prostate-specific antigen), reference biomarker of prostate cancer, can be made.

For a protuberance of a height of 350 µm and a circular base with a diameter of 150 µm, the volume of secretions recovered at the end of 24 hours is around 2 nL.

The detection and the quantification of PSA is done by an ELISA test.

For this, around 50 µl of medium inside several protuberances are collected then deposited in a 96-well plate, placed at 37° C. for 45 minutes. Five successive washes with distilled water are necessary, in order to remove proteins not attached to the anti-PSA primary antibody.

100 µL of free anti-PSA secondary antibody coupled with HRP (Horseradish peroxidase) are then added in each well before 45 minutes of incubation at 37° C. of the ELISA plate. Finally, 100 µL of substrate (TMB) are added, giving rise to a substrate enzyme colorimetric reaction.

After 15 minutes at 37° C., the reaction is stopped by adding 100 µL of sulphuric acid and the absorbance is detected using an ELISA plate reader at 450 nm.

III—Example of Using the Chip for Screening Molecules

In a specific embodiment, the microfluidic cell culture chip according to the invention, is used for screening molecules.

IV—Example of Using the Chip to Determine the Effect of a Treatment of Urological Cancers in a Patient In a specific embodiment, the microfluidic cell culture chip according to the invention, is used to determine the effect of a treatment for a urological cancer in a patient suffering from a urological cancer.

In this embodiment, the analysis of the secretome of isolated cells of the urine of the patient, inserted in the culture of epithelial cells on the protuberance, is done before and after the treatment of the patient, and/or during the treatment.

The comparison of the secretome obtained before the treatment with that obtained after the treatment, and/or that obtained during the treatment, makes it possible to determine the effect of the treatment on the urological cancer of which the patient is suffering from.

BRIEF DESCRIPTION OF THE DRAWINGS 1 support consisting of a non-resorbable membrane (central unit)
2 upper face of the support consisting of a non-resorbable membrane (central unit)
3 lower face of the support consisting of a non-resorbable membrane (central unit)
4 perforation of the support consisting of a non-resorbable membrane (central unit)
5 3D nanostructured porous membrane (central unit)
6 upper face of 3D nanostructured porous membrane (central unit)
7 lower face of 3D nanostructured porous membrane (central unit)
8 protuberance (central unit)
9 outer face of protuberance (central unit)
10 inner face of protuberance (central unit)
11 section of the perforation at the upper face of the support (central unit)
12 section of the perforation at the lower face of the support (central unit)
13 circular base of the protuberance (central unit)
14 duct (lower unit)
15 upper orifice of the duct (lower unit)
16 lower orifice of the duct (lower unit)
17 reservoir (lower unit)
18 duct of the reservoir (lower unit)
19 orifices of the upper unit leading to the inlet/outlet ducts (upper unit)
20 upper orifice of the duct (lower module)
21 lower orifice of the duct (lower module)
22 resorbable polymer
23 3D nanostructure
24 epithelial cell
101 upper module
102 upper unit
103 base of the upper module
104 central module
105 central unit
106 base of the central module
107 lower module
108 lower unit
109 base of the lower module
201 attachment elements
202 inlet/outlet ducts (upper module)
203 chamber (upper unit)
204 attachment elements 205 set of lower orifices of the ducts (lower module)
206 set of upper orifices of the ducts (lower module)
207 set of protuberances (central module)
208 moulded 3D nanostructure
209 upper face of the mould
210 resorbable polymer matrix
211 negative mould of a 3D nanostructure
212 lower face of the matrix
F support part of the central module
213 side frame of the support part
214 open upper face of the support part
215 solid lower face of the support part
216 cut of the solid face of the support part
217 alignment pin
218 alignment hole
H, H1, H2, h1, h2 mould
I, i support part
G, G1, G2, g1, g2 perforated part FIG. 1: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is equal to the value of the diameter d3 of the circular base of said protuberance, and wherein the protuberance is in whole, facing the perforation.

FIG. 2: Schematic, cross-sectional view of a central unit comprising a protuberance in the 3D nanostructured membrane, and a perforation in the support, and wherein the value of the diameter d1 of the upper section of said perforation is less than the value of the diameter d2 of the lower section of said perforation, and is equal to the value of the diameter d3 of the circular base of said protuberance, and wherein the protuberance is in whole, facing the perforation.

FIG. 3: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and to the value of the diameter d3 of the circular base of said protuberance, and wherein the protuberance is partially facing the perforation.

FIG. 4: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is less than the value of the diameter d3 of the circular base of said protuberance, and wherein the protuberance is partially facing the perforation.

FIG. 5: Schematic, cross-sectional view of a central unit comprising a protuberance in the 3D nanostructured membrane, and a perforation in the support, and wherein the value of the diameter d1 of the upper section of said perforation is less than the value of the diameter d2 of the lower section of said perforation, and is less than the value of the diameter d3 of the circular base of said protuberance, and wherein the protuberance is partially facing the perforation.

FIG. 6: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is less than the value of the diameter d3 of the circular base of said protuberance, and wherein the protuberance is partially facing the perforation.

FIG. 7: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is greater than the value of the diameter d3 of the circular base of said protuberance, and wherein the protuberance is in whole, facing the perforation.

FIG. 8: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is greater than the value of the diameter d3 of the circular base of said protuberance, and wherein the protuberance is in whole, facing the perforation.

Figure 9:
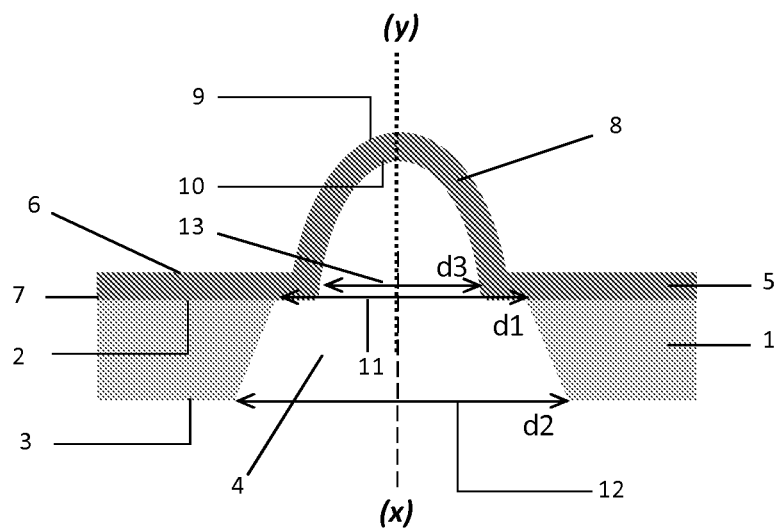

FIG. 9: Schematic, cross-sectional view of a central unit comprising a protuberance in the 3D nanostructured membrane, and a perforation in the support, and wherein the value of the diameter d1 of the upper section of said perforation is less than the value of the diameter d2 of the lower section of said perforation, and is greater than the value of the diameter d3 of the circular base of said protuberance, and wherein the protuberance is in whole, facing the perforation.

FIG. 10: Schematic, cross-sectional view of a central unit comprising a protuberance in the 3D nanostructured membrane, and a perforation in the support, and wherein the value of the diameter d1 of the upper section of said perforation is less than the value of the diameter d2 of the lower section of said perforation, and is greater than the value of the diameter d3 of the circular base of said protuberance, and wherein the protuberance is partially facing the perforation.

FIG. 11: Schematic, cross-sectional view of a central unit comprising a protuberance in the 3D nanostructured membrane, and a perforation in the support, and wherein the value of the diameter d1 of the upper section of said perforation is less than the value of the diameter d2 of the lower section of said perforation, and is greater than the value of the diameter d3 of the circular base of said protuberance, and wherein the protuberance is in whole, facing the perforation.

FIG. 12: Schematic, cross-sectional view of a central unit comprising a protuberance in the 3D nanostructured membrane, and a perforation in the support, and wherein the protuberance is tilted along an axis (z) with respect to the vertical axis (y).

FIG. 13: Schematic, cross-sectional view of a central unit comprising a protuberance in the 3D nanostructured membrane, and a perforation in the support, and wherein the inner face of the protuberance is covered by an assembly of a first cell type at the stage of the confluence, and the outer face of the protuberance is covered by an assembly of a second cell type at the stage of the confluence.

Figure 14:
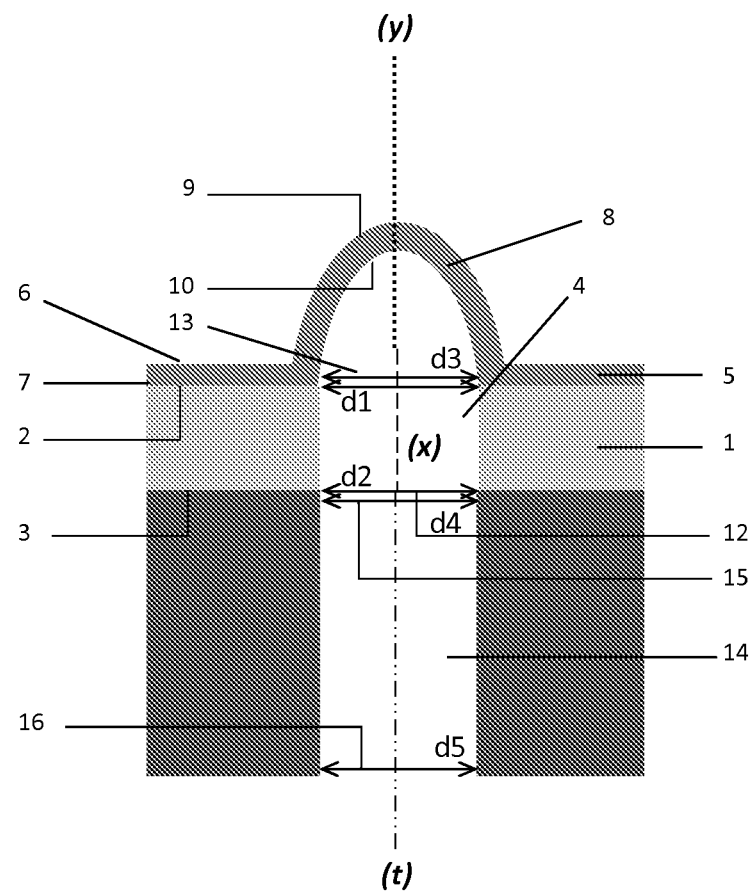

FIG. 14: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is equal to the value of the diameter d3 of the circular base of said protuberance, said central unit being positioned on a lower unit comprising a duct, of which the value of the diameter d4 of the upper orifice is equal to the value of the diameter d2 of the lower section of said perforation, and is equal to the value of the diameter d5 of the lower orifice, and wherein the protuberance is in whole, facing the duct.

FIG. 15: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is equal to the value of the diameter d3 of the circular base of said protuberance, said central unit being positioned on a lower unit comprising a duct, of which the value of the diameter d4 of the upper orifice is equal to the value of the diameter d2 of the lower section of said perforation, and is greater than the value of the diameter d5 of the lower orifice, and wherein the protuberance is in whole, facing the duct.

FIG. 16: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is equal to the value of the diameter d3 of the circular base of said protuberance, said central unit being positioned on a lower unit comprising a duct, of which the value of the diameter d4 of the upper orifice is greater than the value of the diameter d2 of the lower section of said perforation, and is equal to the value of the diameter d5 of the lower orifice, and wherein the protuberance is in whole, facing the duct.

FIG. 17: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is greater than the value of the diameter d3 of the circular base of said protuberance, said central unit being positioned on a lower unit comprising a duct, of which the value of the diameter d4 of the upper orifice is greater than the value of the diameter d2 of the lower section of said perforation, and is equal to the value of the diameter d5 of the lower orifice, and wherein the protuberance is in whole, facing the duct.

FIG. 18: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is greater than the value of the diameter d3 of the circular base of said protuberance, said central unit being positioned on a lower unit comprising a duct, of which the value of the diameter d4 of the upper orifice is greater than the value of the diameter d2 of the lower section of said perforation, and is equal to the value of the diameter d5 of the lower orifice, and wherein the protuberance is in whole, facing the duct.

Figure 19:
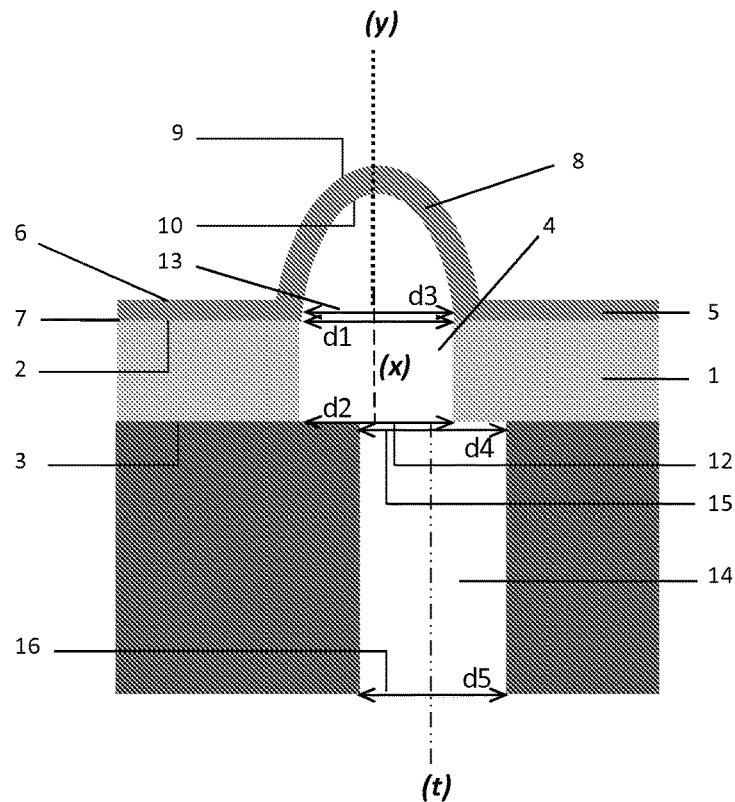

FIG. 19: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is equal to the value of the diameter d3 of the circular base of said protuberance, said central unit being positioned on a lower unit comprising a duct, of which the value of the diameter d4 of the upper orifice is equal to the value of the diameter d2 of the lower section of said perforation, and is equal to the value of the diameter d5 of the lower orifice, and wherein the protuberance is in whole, facing the duct.

Figure 20:
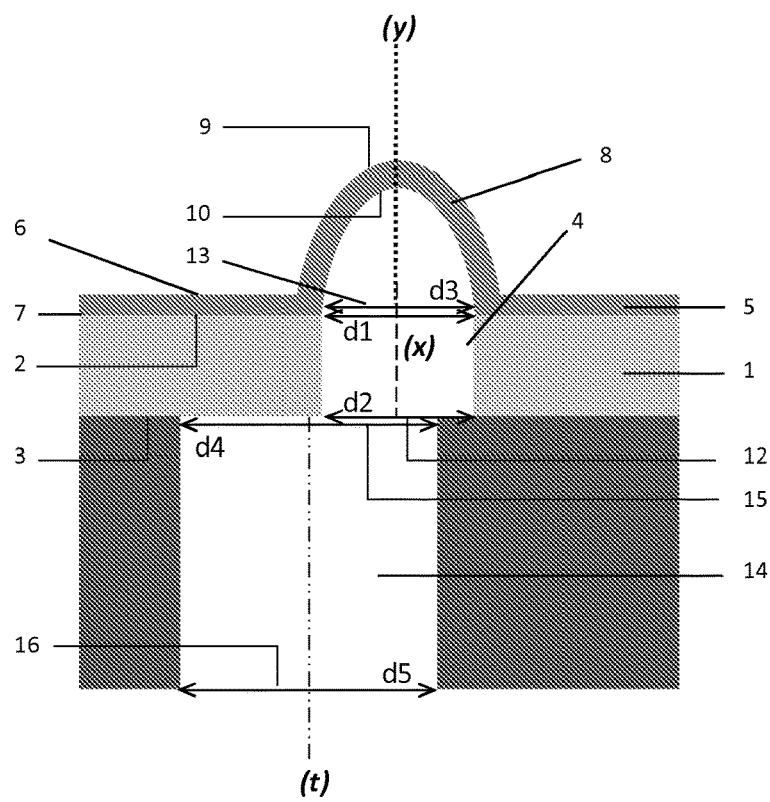

FIG. 20: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is equal to the value of the diameter d3 of the circular base of said protuberance, said central unit being positioned on a lower unit comprising a duct, of which the value of the diameter d4 of the upper orifice is greater than the value of the diameter d2 of the lower section of said perforation, and is equal to the value of the diameter d5 of the lower orifice, and wherein the protuberance is partially facing the duct.

Figure 21:
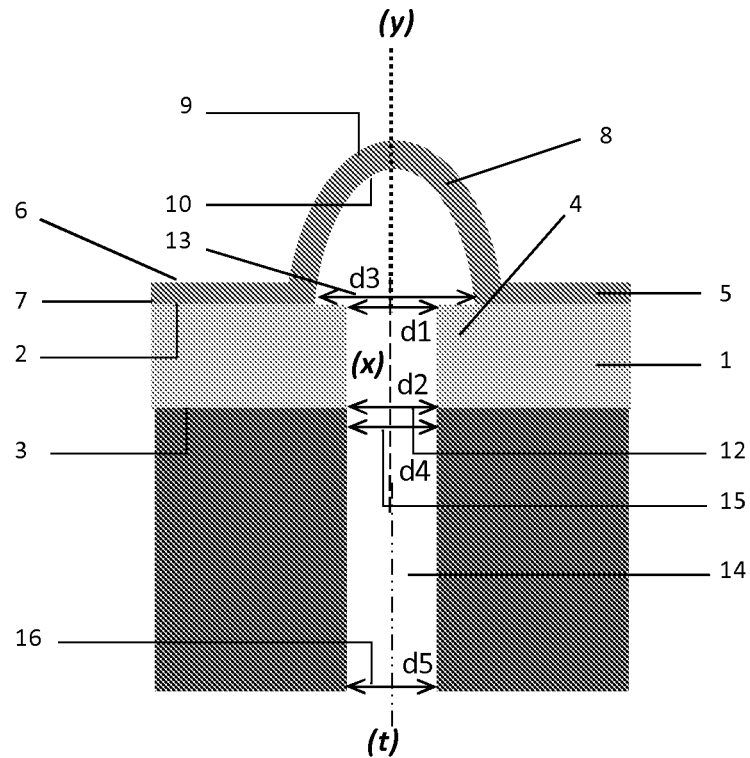

FIG. 21: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is less than the value of the diameter d3 of the circular base of said protuberance, said central unit being positioned on a lower unit comprising a duct, of which the value of the diameter d4 of the upper orifice is equal to the value of the diameter d2 of the lower section of said perforation, and is equal to the value of the diameter d5 of the lower orifice, and wherein the protuberance is partially facing the duct.

Figure 22:
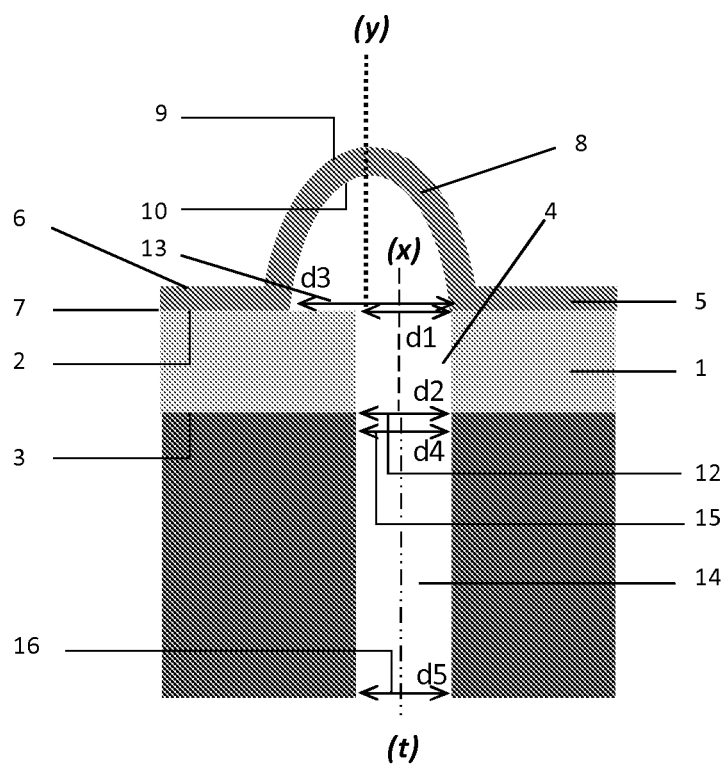

FIG. 22: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is less than the value of the diameter d3 of the circular base of said protuberance, said central unit being positioned on a lower unit comprising a duct, of which the value of the diameter d4 of the upper orifice is equal to the value of the diameter d2 of the lower section of said perforation, and is equal to the value of the diameter d5 of the lower orifice, and wherein the protuberance is partially facing the duct.

Figure 23:
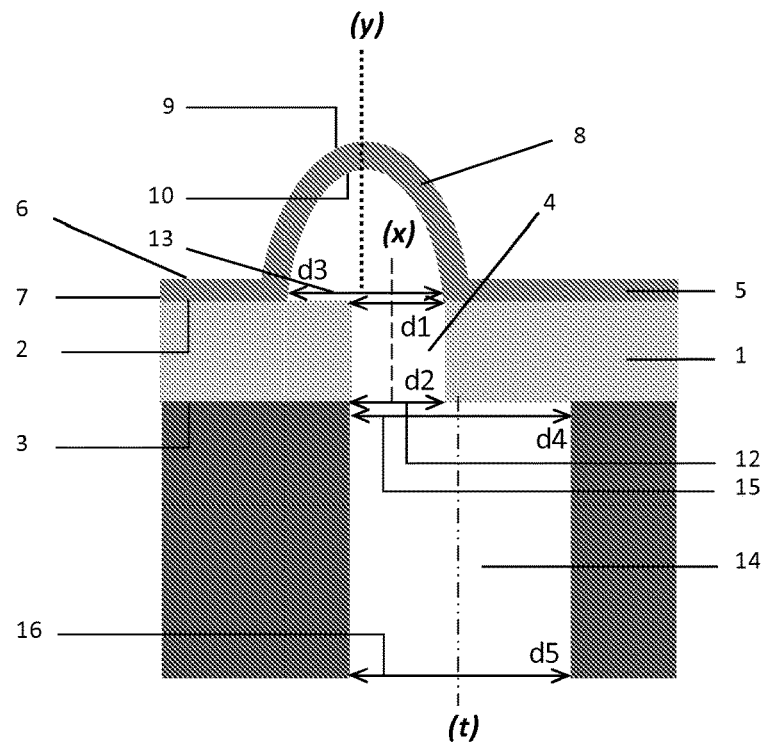

FIG. 23: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is less than the value of the diameter d3 of the circular base of said protuberance, said central unit being positioned on a lower unit comprising a duct, of which the value of the diameter d4 of the upper orifice is greater than the value of the diameter d2 of the lower section of said perforation, and is equal to the value of the diameter d5 of the lower orifice, and wherein the protuberance is partially facing the duct.

Figure 24:
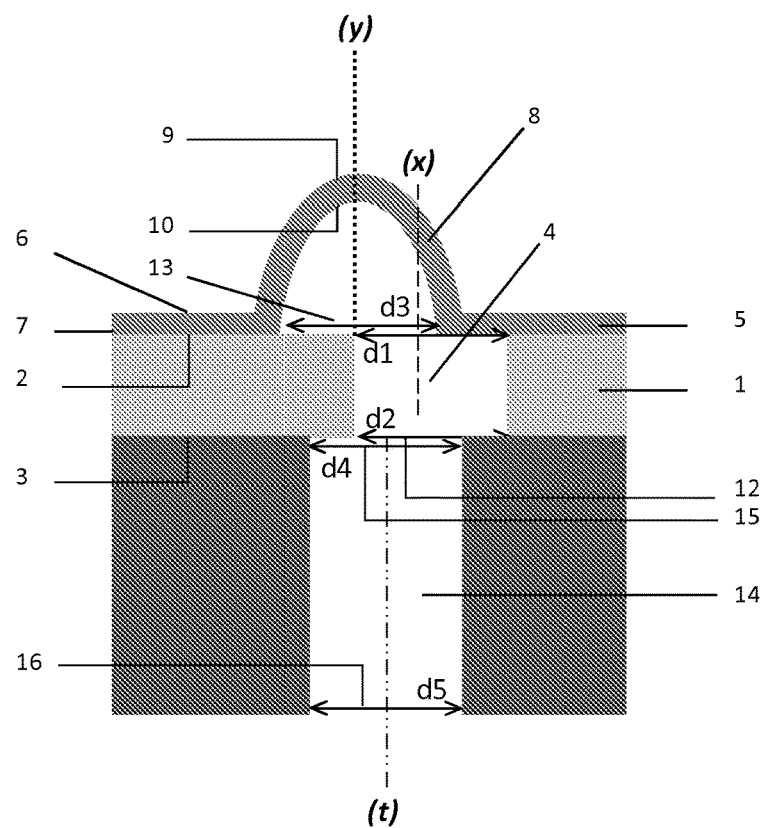

FIG. 24: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is equal to the value of the diameter d3 of the circular base of said protuberance, said central unit being positioned on a lower unit comprising a duct, of which the value of the diameter d4 of the upper orifice is equal to the value of the diameter d2 of the lower section of said perforation, and is equal to the value of the diameter d5 of the lower orifice, and wherein the protuberance is partially facing the duct.

Figure 25:
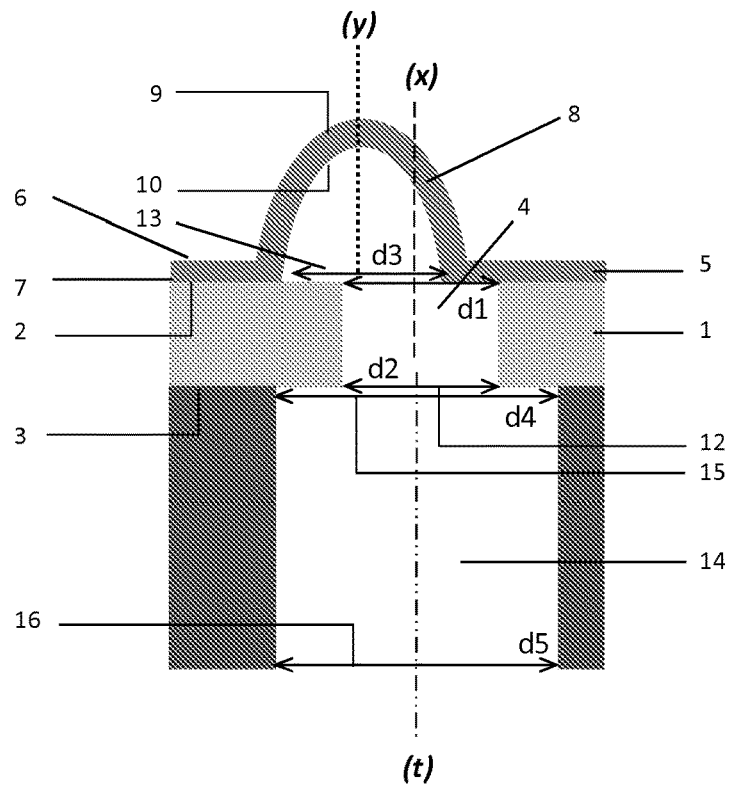

FIG. 25: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is equal to the value of the diameter d3 of the circular base of said protuberance, said central unit being positioned on a lower unit comprising a duct, of which the value of the diameter d4 of the upper orifice is greater than the value of the diameter d2 of the lower section of said perforation, and is equal to the value of the diameter d5 of the lower orifice, and wherein the protuberance is partially facing the duct.

Figure 26:
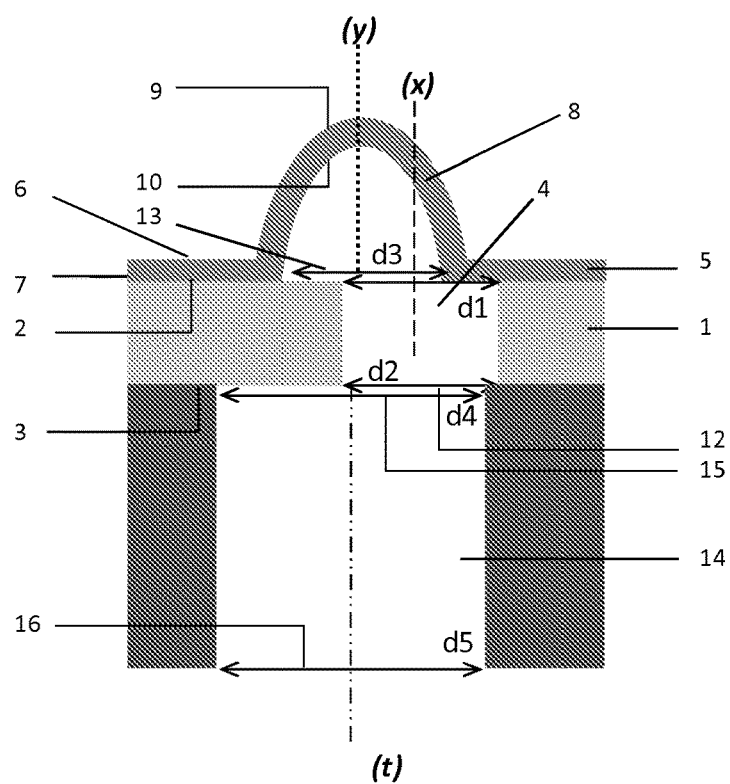

FIG. 26: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is equal to the value of the diameter d3 of the circular base of said protuberance, said central unit being positioned on a lower unit comprising a duct, of which the value of the diameter d4 of the upper orifice is greater than the value of the diameter d2 of the lower section of said perforation, and is equal to the value of the diameter d5 of the lower orifice, and wherein the protuberance is partially facing the duct.

Figure 27:
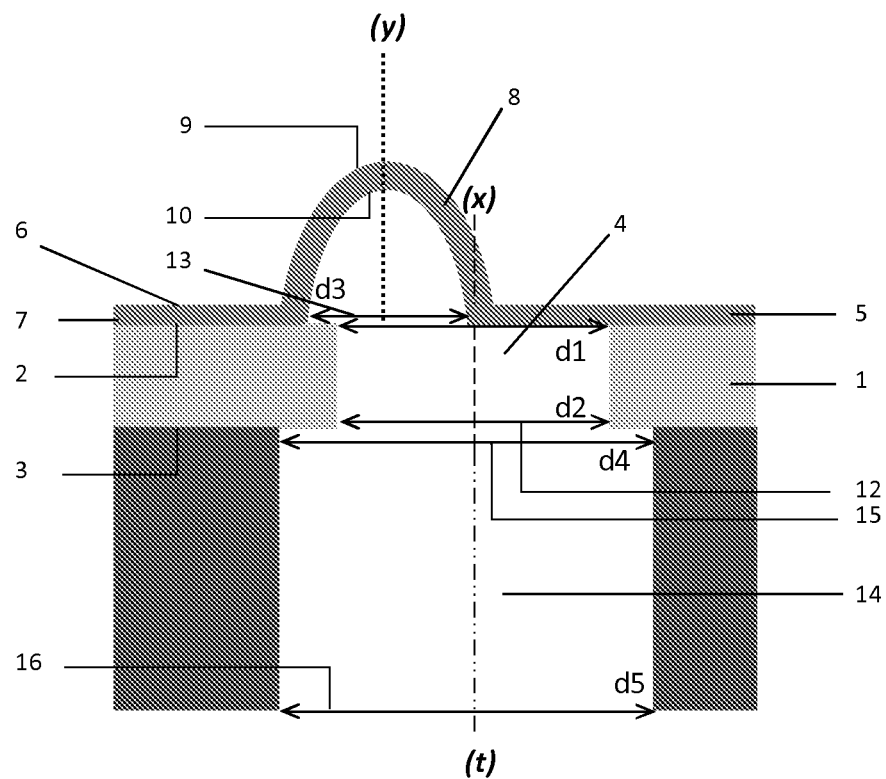

FIG. 27: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is greater than the value of the diameter d3 of the circular base of said protuberance, said central unit being positioned on a lower unit comprising a duct, of which the value of the diameter d4 of the upper orifice is greater than the value of the diameter d2 of the lower section of said perforation, and is equal to the value of the diameter d5 of the lower orifice, and wherein the protuberance is partially facing the duct.

Figure 28:
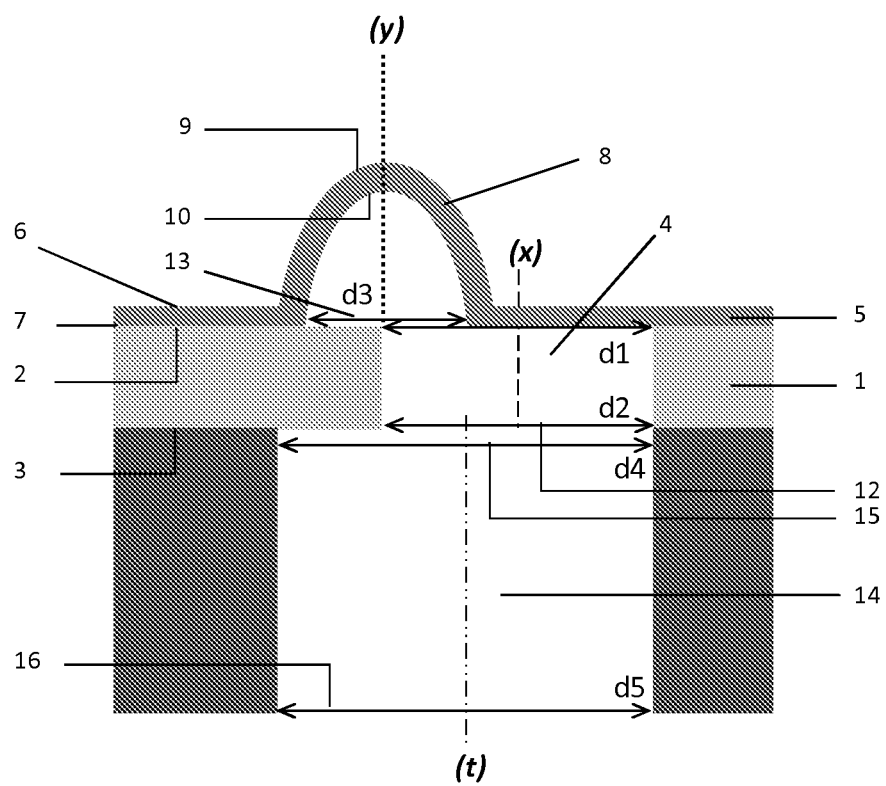

FIG. 28: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is greater than the value of the diameter d3 of the circular base of said protuberance, said central unit being positioned on a lower unit comprising a duct, of which the value of the diameter d4 of the upper orifice is greater than the value of the diameter d2 of the lower section of said perforation, and is equal to the value of the diameter d5 of the lower orifice, and wherein the protuberance is partially facing the duct.

Figure 29:
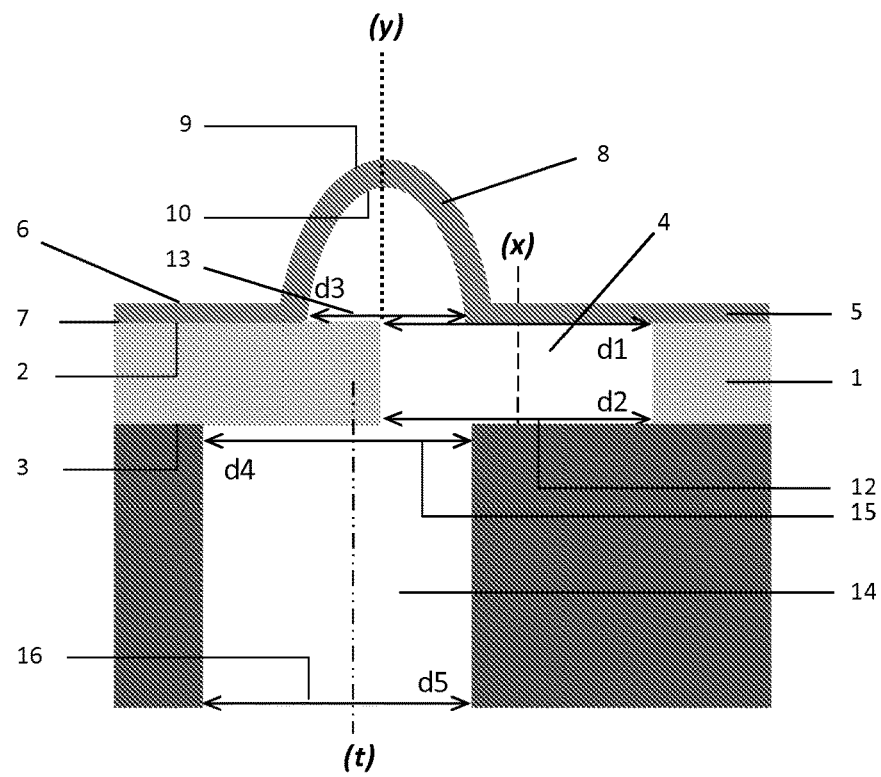

FIG. 29: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is greater than the value of the diameter d3 of the circular base of said protuberance, said central unit being positioned on a lower unit comprising a duct, of which the value of the diameter d4 of the upper orifice is equal to the value of the diameter d2 of the lower section of said perforation, and is equal to the value of the diameter d5 of the lower orifice, and wherein the protuberance is partially facing the duct.

Figure 30:
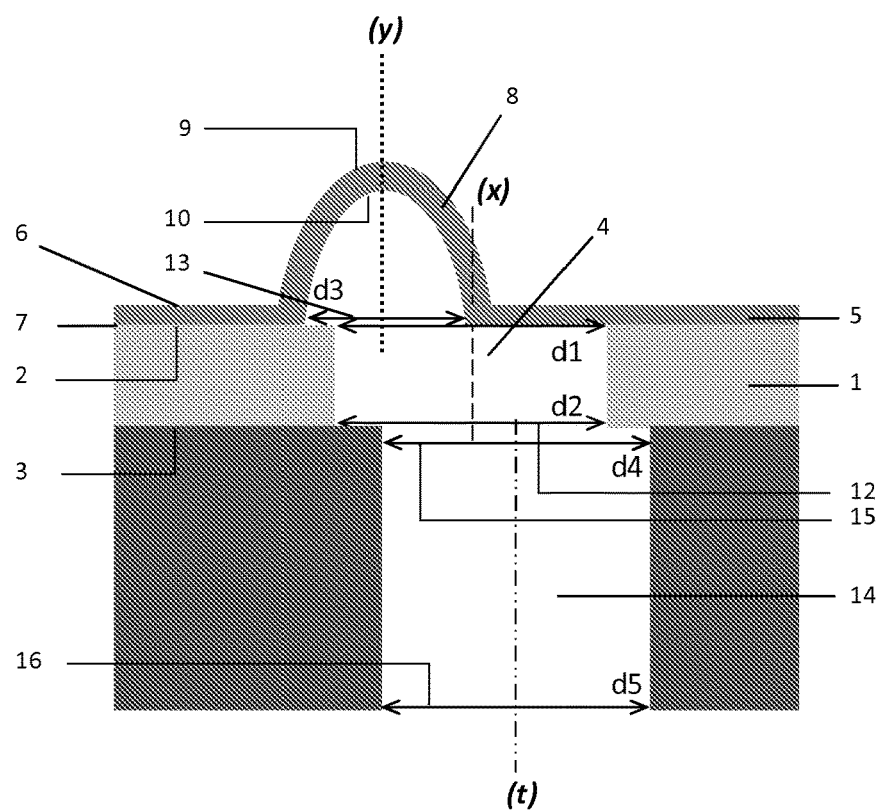

FIG. 30: Schematic, cross-sectional view of a central unit comprising a protuberance in the 3D nanostructured membrane, and a perforation in the support, and wherein the value of the diameter d1 of the upper section of said perforation is equal to the value of the diameter d2 of the lower section of said perforation, and is greater than the value of the diameter d3 of the circular base of said protuberance, said central unit being positioned on a lower unit comprising a duct, of which the value of the diameter d4 of the upper orifice is equal to the value of the diameter d2 of the lower section of said perforation, and is equal to the value of the diameter d5 of the lower orifice, and wherein the protuberance is partially facing the duct.

FIG. 31: Schematic, cross-sectional view of a central unit comprising two protuberances in the 3D nanostructured membrane, and two perforations in the support, and wherein the value of the diameter d1 of the upper section of each of the perforations is equal to the value of the diameter d2 of the lower section of each of the perforations, and is equal to the value of the diameter d3 of the circular base of each of the protuberances, said central unit being positioned on a lower unit comprising two ducts, of which the value of the diameter d4 of the upper orifice of each of the ducts is equal to the value of the diameter d2 of the lower section of each of the perforations and is equal to the value of the diameter d5 of the lower orifice, and the two lower orifices of the two ducts respectively leading to a reservoir, leading to the outside of the lower module via an outlet duct (protuberance in whole, facing the duct).

FIG. 32: Schematic, cross-sectional view of a central unit comprising two protuberances in the 3D nanostructured membrane, and two perforations in the support, and wherein the value of the diameter d1 of the upper section of each of the perforations is equal to the value of the diameter d2 of the lower section of each of the perforations, and is equal to the value of the diameter d3 of the circular base of each of the protuberances, said central unit being positioned on a lower unit comprising two ducts, of which the value of the diameter d4 of the upper orifice of each of the ducts is equal to the value of the diameter d2 of the lower section of each of the perforations and is equal to the value of the diameter d5 of the lower orifice, and the two lower orifices of the two ducts leading to the outside of the lower module in two distinct sites (protuberance in whole, facing the duct).

FIG. 33: Schematic, cross-sectional view of a central unit comprising two protuberances in the 3D nanostructured membrane, and two perforations in the support, and wherein the value of the diameter d1 of the upper section of each of the perforations is equal to the value of the diameter d2 of the lower section of each of the perforations, and is equal to the value of the diameter d3 of the circular base of each of the protuberances, said central unit being positioned on a lower unit comprising two ducts, of which the value of the diameter d4 of the upper orifice of each of the ducts is equal to the value of the diameter d2 of the lower section of each of the perforations and is equal to the value of the diameter d5 of the lower orifice, and the two ducts are connected to one another such that the two lower orifices of the two ducts lead to the outside of the lower module in the same site (protuberance in whole, facing the duct).

FIG. 34: Schematic, cross-sectional view of a central unit comprising two protuberances in the 3D nanostructured membrane, and two perforations in the support, and wherein the value of the diameter d1 of the upper section of each of the perforations is equal to the value of the diameter d2 of the lower section of each of the perforations, and is equal to the value of the diameter d3 of the circular base of each of the protuberances, said central unit being positioned on a lower unit comprising two ducts, of which the value of the diameter d4 of the upper orifice of each of the ducts is equal to the value of the diameter d2 of the lower section of each of the perforations and is equal to the value of the diameter d5 of the lower orifice, and the two lower orifices of the two ducts respectively leading to a reservoir, each of the reservoirs leading to the outside of the lower module in the same site, via the outlet ducts connected to one another (protuberance in whole, facing the duct).

FIG. 35: Schematic, cross-sectional view of a central unit comprising two protuberances in the 3D nanostructured membrane, and two perforations in the support, and wherein the value of the diameter d1 of the upper section of each of the perforations is equal to the value of the diameter d2 of the lower section of each of the perforations, and is equal to the value of the diameter d3 of the circular base of each of the protuberances, said central unit being positioned on a lower unit comprising two ducts, of which the value of the diameter d4 of the upper orifice of each of the ducts is equal to the value of the diameter d2 of the lower section of each of the perforations and is greater than the value of the diameter d5 of the lower orifice, and the two ducts are connected to one another such that the two lower orifices of the two ducts lead to the same site on a reservoir, which leads to the outside of the lower module via an outlet duct (protuberance in whole, facing the duct).

FIG. 36: Schematic, cross-sectional view of a central unit comprising two protuberances in the 3D nanostructured membrane, and two perforations in the support, and wherein the value of the diameter d1 of the upper section of each of the perforations is equal to the value of the diameter d2 of the lower section of each of the perforations, and is equal to the value of the diameter d3 of the circular base of each of the protuberances, said central unit being positioned on a lower unit comprising two ducts, of which the value of the diameter d4 of the upper orifice of each of the ducts is equal to the value of the diameter d2 of the lower section of each of the perforations and is greater than the value of the diameter d5 of the lower orifice, and the two lower orifices of the two ducts respectively lead to two distinct sites on one same reservoir, which leads to the outside of the lower module via an outlet duct (protuberance in whole, facing the duct).

FIG. 37: Schematic, cross-sectional view of a central unit comprising four protuberances in the 3D nanostructured membrane, and four perforations in the support, and wherein the value of the diameter d1 of the upper section of each of the perforations is equal to the value of the diameter d2 of the lower section of each of the perforations, and is equal to the value of the diameter d3 of the circular base of each of the protuberances, said central unit being positioned on a lower unit comprising four ducts, of which the value of the diameter d4 of the upper orifice of each of the ducts is equal to the value of the diameter d2 of the lower section of each of the perforations and the two lower orifices of a first set of two ducts respectively lead to two distinct sites on a first reservoir, and the two lower orifices of a second set of two ducts respectively lead to two distinct sites on a second reservoir, the first and the second reservoir respectively leading to the outside of the lower module in distinct sites (protuberance in whole, facing the duct).

FIG. 38: Schematic, perspective view of the upper module.

FIG. 39: Schematic, perspective view of the central module.

FIG. 40: Schematic, perspective view taken from above the upper face of the 3D nanostructured porous membrane, of a central unit comprising a set of protuberances.

FIG. 41: Schematic, perspective view of the lower module.

FIG. 42: Schematic, perspective view of the microfluidic chip comprising the assembly of the upper module, of the central module and of the lower module.

FIG. 43: Photo of the upper module (side view of the opening of the chamber).

Figure 44:
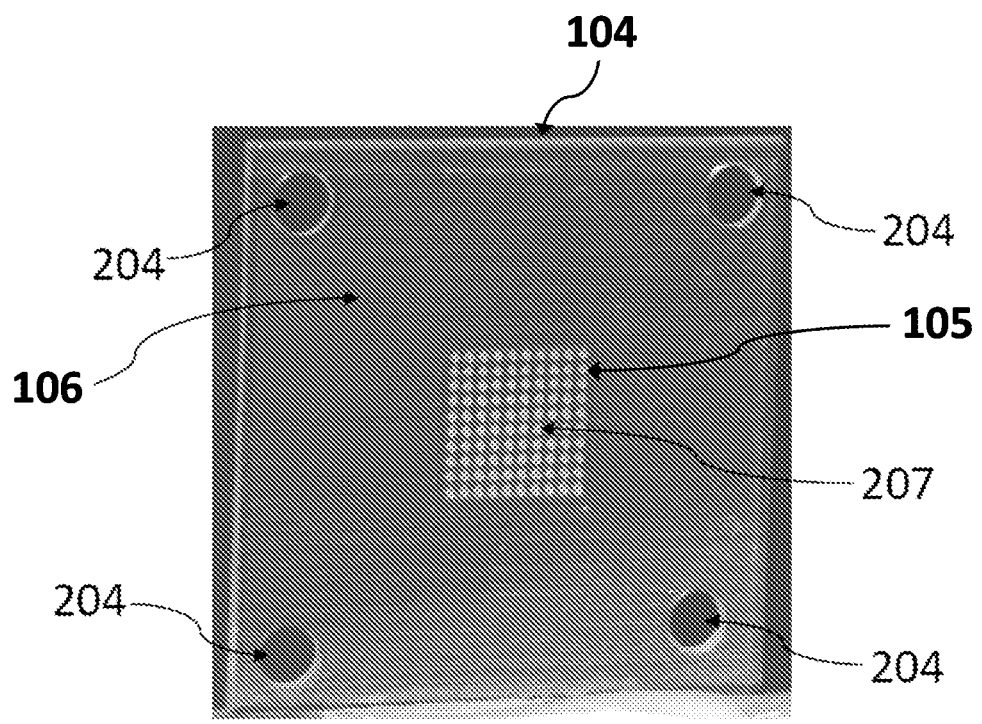

FIG. 44: Photo of the central module. Top view of the upper face of the 3D nanostructured porous membrane comprising a set of protuberances.

FIG. 45: Photo of the lower module. Top view of the upper face of the lower unit comprising the set of upper orifices of the ducts.

FIG. 46: Photo of the upper module and of the lower module.

FIG. 47: Photo of the disassembled upper module, of the disassembled central module and of the disassembled lower module.

Figure 48:
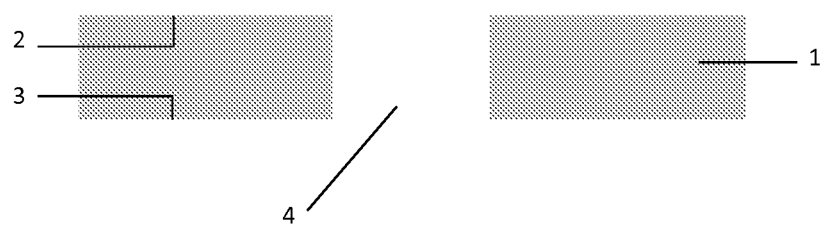

FIG. 48: Schematic, cross-sectional view of the support consisting of a non-resorbable membrane, of the central unit, comprising a perforation.

Figure 49:
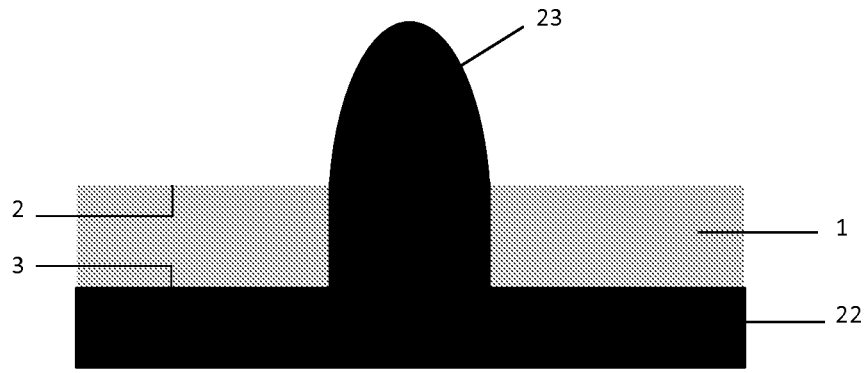

FIG. 49: Schematic, cross-sectional view of the support consisting of a non-resorbable membrane, of the central unit, comprising a perforation, through which a resorbable polymer has been extruded to form a 3D nanostructure on the side of the upper face of said support.

FIG. 50: Schematic, cross-sectional view of the support consisting of a non-resorbable membrane, of the central unit, comprising a perforation, through which a resorbable polymer has been extruded to form a 3D nanostructure on the side of the upper face of said support on which a polyelectrolyte layer has been applied to obtain the 3D nanostructured porous membrane comprising a moulded protuberance on said 3D nanostructure.

FIG. 51: Schematic, cross-sectional view of the support consisting of a non-resorbable membrane and comprising a perforation, of the central unit, on which is positioned secured to the 3D nanostructured membrane comprising a hollow protuberance.

FIG. 52: Photo using a confocal microscope of the inner face of a protuberance supporting a culture of epithelial cells at the stage of the confluence.

Figure 53:
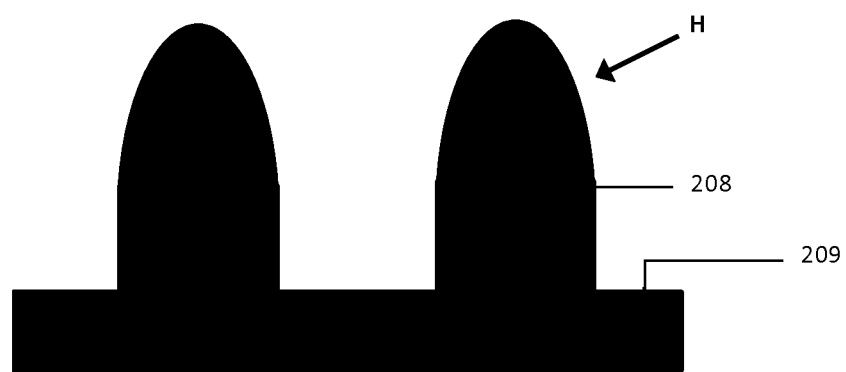

FIG. 53: Schematic, cross-sectional view of a mould comprising at least one moulded 3D nanostructure on the side of the upper face thereof.

Figure 54:
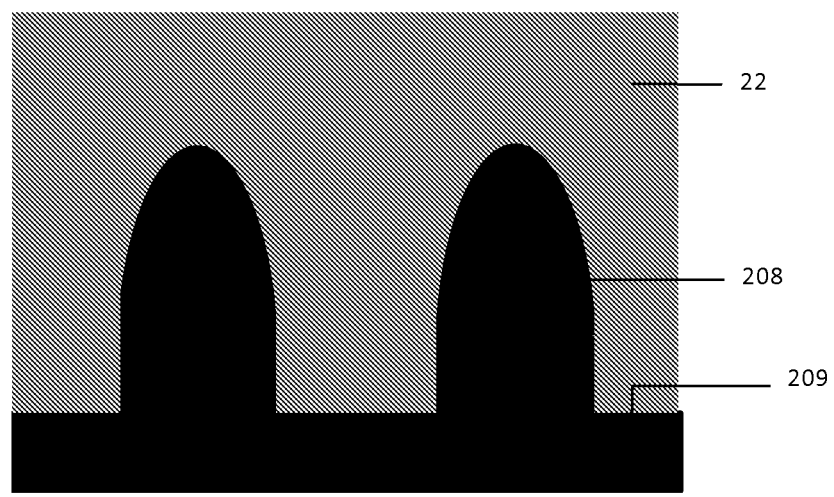

FIG. 54: Schematic, cross-sectional view of a mould covered with resorbable polymer on the side of the upper face of said mould.

Figure 55:
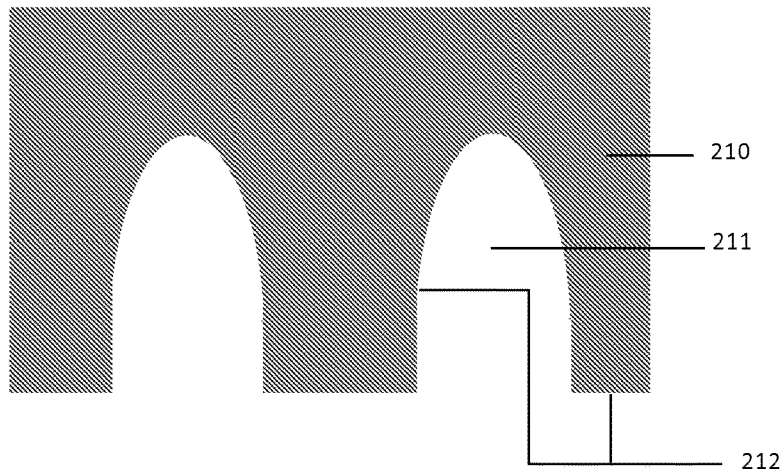

FIG. 55: Schematic, cross-sectional view of a resorbable polymer matrix comprising at least one negative mould of at least one moulded 3D nanostructure.

Figure 56:
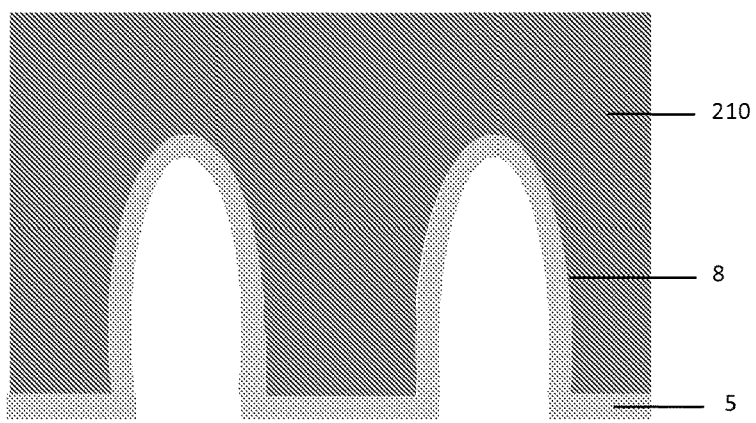

FIG. 56: Schematic, cross-sectional view of a resorbable polymer matrix comprising at least one negative mould of at least one moulded 3D nanostructure, the lower face of said matrix being covered by a polyelectrolyte layer.

Figure 57:
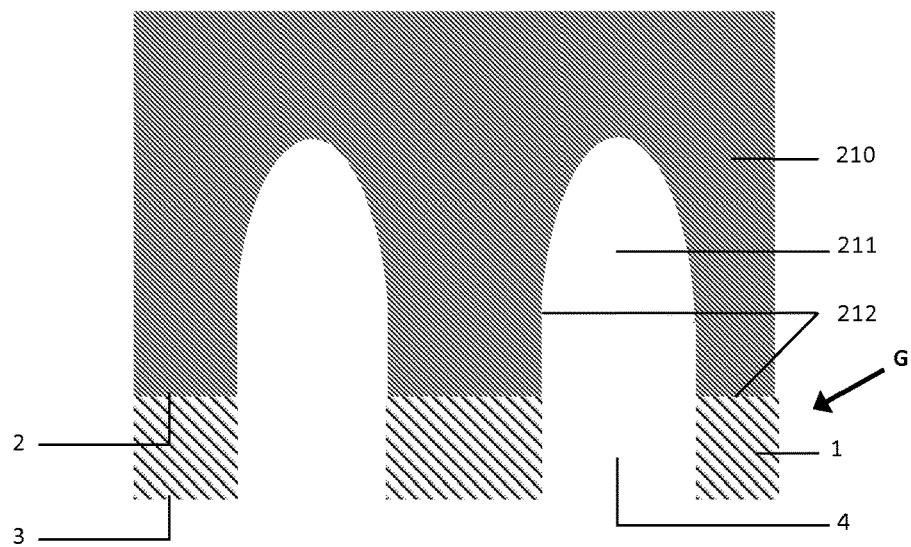

FIG. 57: Schematic, cross-sectional view of a resorbable polymer matrix comprising at least one negative mould of at least one moulded 3D nanostructure assembled with a perforated part comprising a support consisting of a non-resorbable membrane perforated by at least one perforation, said matrix being assembled on the side of the lower face thereof with the upper face of said support, such that the negative mould of the 3D nanostructure is aligned with said perforation of the support.

FIG. 58: Schematic, cross-sectional view of a resorbable polymer matrix comprising at least one negative mould of at least one moulded 3D nanostructure assembled with a perforated part comprising a support consisting of a non-resorbable membrane perforated by at least one perforation, said matrix being assembled on the side of the lower face thereof with the upper face of said support, such that the negative mould of the 3D nanostructure is aligned with said perforation of the support, wherein the continuous surface constituted by the lower face of said support and the lower face of said resorbable polymer matrix comprising at least one negative mould at said at least one perforation of said support, is covered by a polyelectrolyte layer to form a 3D nanostructured membrane comprising at least one protuberance.

FIG. 59: Schematic, cross-sectional view of the central module corresponding to the perforated part comprising, on the side of the lower face of the support, a 3D nanostructured porous membrane and on the side of the upper face of the support, at least one protuberance in the extension of the at least one perforation of the support of the perforated part.

Figure 60:
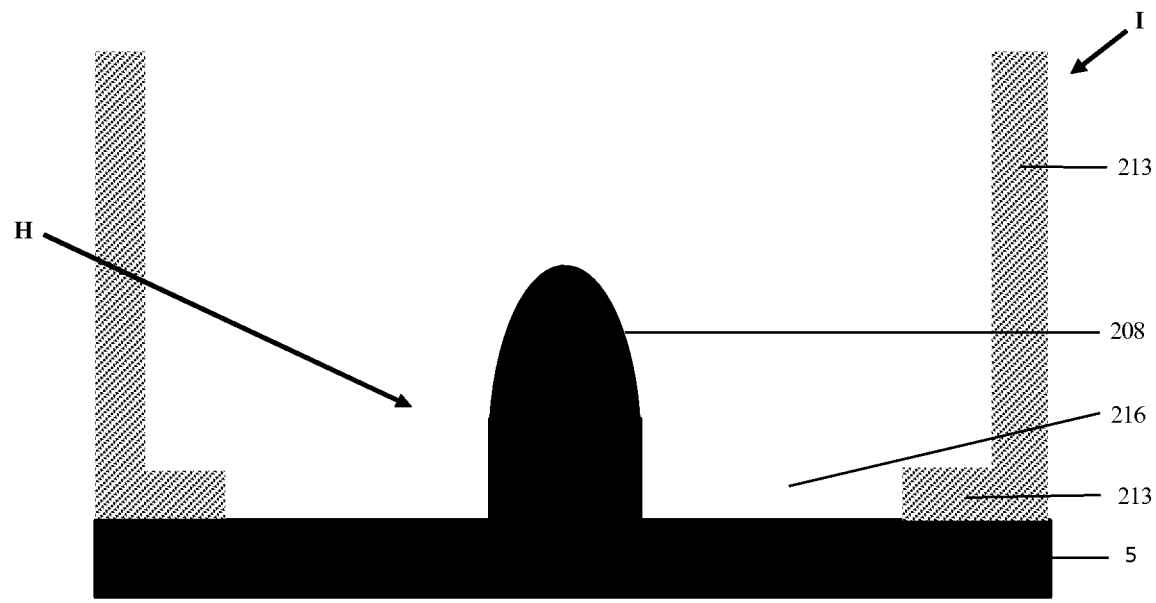

FIG. 60: Schematic, cross-sectional view of a mould comprising at least one moulded 3D nanostructure on the side of the upper face thereof, assembled on the side of the upper face thereof with a support part comprising a cut in the lower face thereof.

Figure 61:
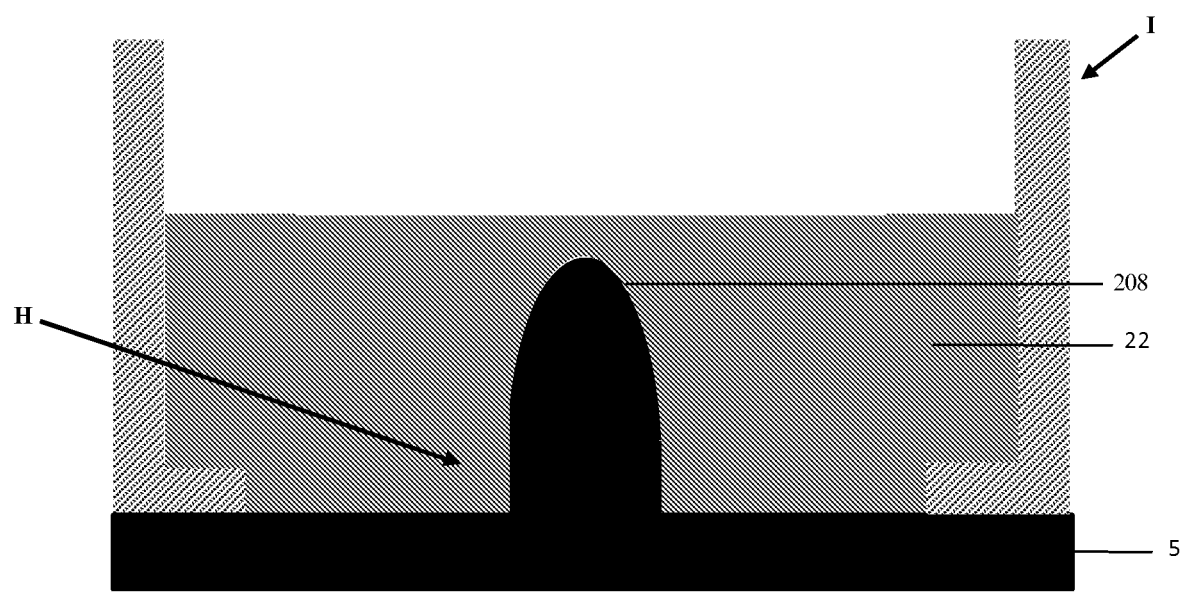

FIG. 61: Schematic, cross-sectional view of a mould comprising at least one moulded 3D nanostructure on the side of the upper face thereof, assembled on the side of the upper face thereof with a support part comprising a cut in the lower face thereof, where said mould is covered by resorbable polymer on the side of the upper face thereof.

FIG. 62: Schematic, cross-sectional view of a resorbable polymer matrix comprising at least one negative mould of at least one moulded 3D nanostructure, said matrix being formed at the cut of the support part.

FIG. 63: Schematic, cross-sectional view of a support part containing at the cut of the solid lower face thereof, a resorbable polymer matrix comprising at least one negative mould of at least one moulded 3D nanostructure, said support part being assembled to a perforated part comprising a support with at least one perforation, such that said negative mould of at least one moulded 3D nanostructure is aligned with said perforation.

Figure 64:
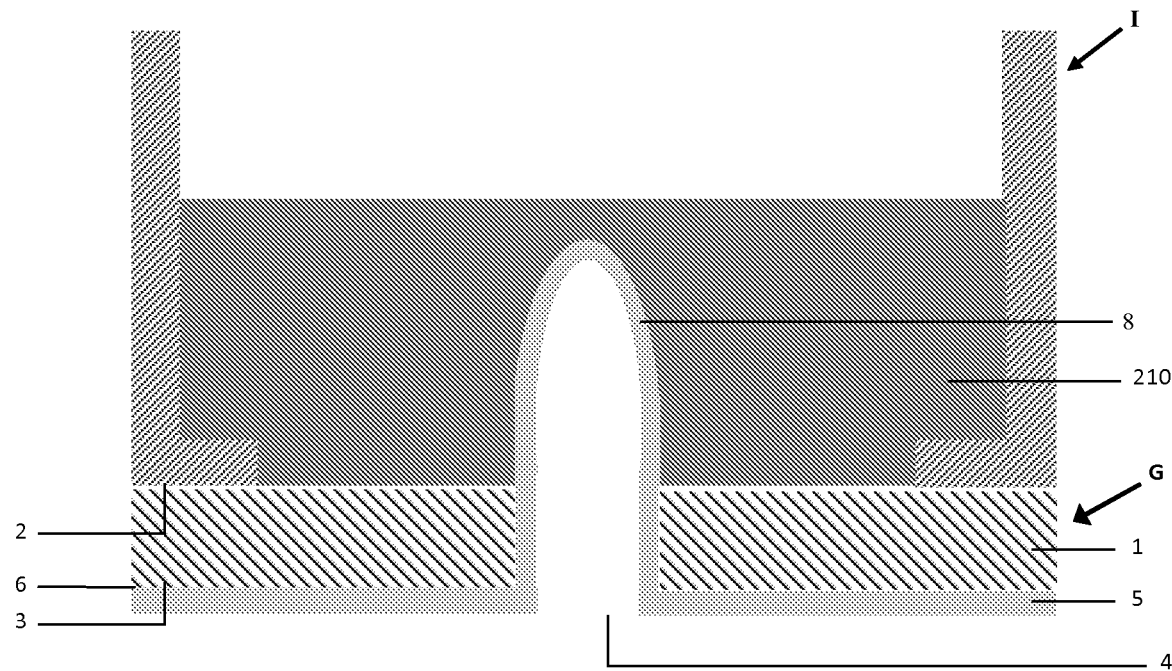

FIG. 64: Schematic, cross-sectional view of a support part containing at the cut of the solid lower face thereof, a resorbable polymer matrix comprising at least one negative mould of at least one moulded 3D nanostructure, said support part being assembled to a perforated part comprising a support with at least one perforation, such that said negative mould of at least one moulded 3D nanostructure is aligned with said perforation, the continuous surface constituted by the lower face of said support and the lower face of said resorbable polymer matrix comprising at least one negative mould at the said at least one perforation of said support, being covered by a polyelectrolyte layer to form a 3D nanostructured membrane comprising at least one protuberance.

FIG. 65: Schematic, cross-sectional view of the support of the perforated part comprising, on the side of the lower face thereof, a 3D nanostructured porous membrane and on the side of the upper face thereof, at least one polyelectrolyte protuberance in the extension of the at least one perforation of the support of the perforated part, and the support part I.

FIG. 66: Schematic, cross-sectional view of the central module corresponding to the perforated part comprising, on the side of the lower face of the support, a 3D nanostructured porous membrane, and on the side of the upper face of the support, at least one protuberance in the extension of the at least one perforation of the support of the perforated part.

FIG. 67: Schematic, perspective view of a circular-shaped support part I, of a circular-shaped mould H and comprising 100 moulded 3D nanostructures (H1), of a circular-shaped perforated part G and comprising 100 perforations (G1) and of a support part F of the central module.

FIG. 68: Schematic, perspective view of a circular-shaped support part I, of a circular-shaped mould H and comprising 9 moulded 3D nanostructures (H2), of a circular-shaped perforated part G and comprising 9 perforations (G2) and of a support part F of the central module.

FIG. 69: Schematic, perspective views of the assembly of a circular-shaped support part I on a circular-shaped mould H and comprising 100 moulded 3D nanostructures (H1), via the alignment pin of I and the alignment hole of H1. A: Top view when the two elements are assembled. B: Top view when the elements are disassembled. C: Profile view when the two elements are assembled. D: Profile view when the two elements are disassembled.

FIG. 70: Schematic, perspective views of the assembly of a circular-shaped support part I on a circular-shaped perforated part G and comprising 100 perforations (G1) via the alignment pin I and the alignment hole of G1. A: Top view when the two elements are assembled. B: Top view when the elements are disassembled. C: Bottom view when the two elements are assembled. D: Bottom view when the two elements are disassembled. E: Profile view when the two assembled elements are returned such that G1 is oriented towards the top and I is oriented towards the bottom.

FIG. 71: Schematic, perspective views of the assembly of a circular-shaped perforated part G and comprising 100 perforations (G1) on a support part F of the central module. A: Bottom view of the two assembled elements. B: Bottom view when the two elements are disassembled. C: Profile view when the two elements are assembled. D: Profile view when the two elements are assembled.

FIG. 72: Schematic, perspective view of a square-shaped support part i, of a square-shaped mould H and comprising 100 moulded 3D nanostructures (h1), of a square-shaped perforated part G comprising 100 perforations (g1).

FIG. 73: Schematic, perspective view of a square-shaped support part i, of a square-shaped mould H and comprising 9 moulded 3D nanostructures (h2), of a square-shaped perforated part G and comprising 9 perforations (g2).

The invention claimed is:

1. A microfluidic cell culture chip comprising a central module that comprises:
   a central unit, which contains
     a support consisting of a non-resorbable membrane, said support comprising an upper face and a lower face and being perforated by at least one perforation,
     a 3D nanostructured porous membrane, juxtaposed to the non-resorbable membrane, comprising an upper face and a lower face, and comprising at least one protuberance, said at least one protuberance being hollow, comprising an outer face and an inner face and forming a relief structure on a side of the upper face of the 3D nanostructured porous membrane,
   said lower face of said 3D nanostructured porous membrane being positioned and secured to said upper face of said support, or said upper face of the 3D nanostructured porous membrane being positioned and secured to said lower face of said support, and said 3D nanostructured porous membrane and the at least one protuberance being composed of materials, suitable for a culture of two distinct cell types; and a base, said central unit being integrated in said base and forming a whole with said base.

2. The microfluidic cell culture chip according to claim 1, wherein said lower face of said 3D nanostructured porous membrane is positioned and secured to said upper face of said support.

3. A method for producing the microfluidic cell culture chip according to claim 2, wherein a production of said central unit comprises:

a step of extruding a resorbable polymer solution, through the at least one perforation of said support to form at least one 3D nanostructure on the side of said upper face of said support, followed by a step of polymerising said resorbable polymer solution to make rigid said at least one 3D nanostructure, said at least one 3D nanostructure forming a resorbable polymer mould on the side of said upper face of said support after polymerisation, followed by a step of applying at least one continuous layer of at least one polyelectrolyte covering the upper face of said support and a surface of said resorbable polymer mould, to constitute the 3D nanostructure porous membrane, followed by a step of dissolving said resorbable polymer mould to obtain said lower face of said 3D nanostructured porous membrane positioned and secured to said upper face of said support, an entirety of said inner face of the at least one protuberance facing said at least one perforation.

4. The microfluidic cell culture chip according to claim 1, wherein said upper face of the 3D nanostructured porous membrane is positioned and secured to said lower face of said support.

5. A method for producing the microfluidic cell culture chip according to claim 4, wherein a production of the central module comprises:

a step of assembling a support part, consisting of a side frame, an open upper face and a solid lower face comprising a cut in a form of the central unit, and a mould, in shapes and dimensions of said support part, comprising at least one moulded 3D nanostructure on the upper face, a step of pouring a resorbable polymer solution on said upper face of said mould, followed by a step of polymerising said resorbable polymer solution to make rigid said resorbable polymer solution and form a resorbable polymer matrix comprising at least one negative mould of said at least one 3D nanostructure, followed by a step of removing said mould, to obtain said resorbable polymer matrix comprising at least one negative mould of said at least one 3D nanostructure formed in said cut of the solid lower face of said support part, followed by a step of assembling said support part, with a perforated part, comprising a support consisting of a non-resorbable membrane perforated by at least one perforation integrated in a base, said perforated part being in the shapes and dimensions of said support part, and the number of the at least one perforation of said perforated part being identical to the number of moulded 3D nanostructures in said mould used in the step of assembling said support part and said mould, such that said at least one perforation of said support, is aligned with said at least one negative mould of said at least one 3D nanostructure, followed by a step of applying at least one continuous layer of at least one polyelectrolyte on the continuous surface consisting of the lower face of said support and the lower face of said resorbable polymer matrix comprising at least one negative mould of said at least one 3D nanostructure at the said at least one perforation of said support, to constitute the 3D nanostructured porous membrane comprising the at least one protuberance, followed by a step of dissolving said resorbable polymer matrix comprising at least one negative mould of said at least one 3D nanostructure, and a step of removing the support part to obtain said perforated part comprising on the lower face thereof, the 3D nanostructured porous membrane, and on the side of the upper face thereof, said at least one protuberance.

6. The microfluidic cell culture chip according to claim 1, wherein the 3D nanostructured porous membrane includes at least one layer of a polyelectrolyte selected from the group consisting of poly(sodium 4-styrenesulphonate) (PSS), poly (ethyleneimine), poly(diallyldimethylammonium chloride), poly(acrylamide-co-diallyldimethylammonium chloride), diallyldimethylammonium chloride, poly(allylamine hydrochloride) (PAH), polyanetholesulfonic acid, polyacrylic acid, poly(styrene-alt-maleic acid), polyvinyl sulphate, polyvinylsulfonic acid, poly(2-acrylamido-2-methyl-1-propanesulfonic acid), poly(2-acrylamido-2-methyl-1-propanesulfonic acid-co-acrylonitrile), poly(4-styrenesulfonic acid), poly(4-styrenesulfonic-acid-co-maleic acid), and hydrated 4-styrenesulfonic sodium salt, and wherein when said 3D nanostructured porous membrane includes at least two successive layers, a layer consisting of a positively charged polyelectrolyte alternates with a layer consisting of a negatively charged polyelectrolyte.

7. The microfluidic cell culture chip according to claim 1, wherein said at least one protuberance is in a shape of a hollow dome having a circular base.

8. The microfluidic cell culture chip according to claim 7, wherein said at least one perforation of the support has a circular-shaped section at the upper face of the support, which corresponds to an upper section of the at least one perforation, having a diameter $d1$, which corresponds to an upper diameter $d1$ of the at least one perforation and a first axis passing through the centre of said upper section of the at least one perforation and perpendicular to said support, and a circular-shaped section at the lower face of the support, which corresponds to a lower section of the at least one perforation, having a diameter $d2$, which corresponds to a lower diameter $d2$ of the at least one perforation and a second axis passing through the centre of said lower section of the at least one perforation and perpendicular to said support, wherein said first axis coincides with said second axis, the diameter $d1$ being a value greater than or equal to 10 μm and less than or equal to 500 μm, and the diameter $d2$ being a value greater than or equal to 10 μm and less than or equal to 500 μm, wherein the value of the diameter $d2$ is greater than or equal to the value of the diameter $d1$, wherein said circular base of said at least one protuberance has a diameter $d3$, said diameter $d3$ of the circular base of the at least one protuberance being a value greater than or equal to 10 μm and less than or equal to 500 μm, and wherein said at least one protuberance has a height of 1 to 600 μm.

9. The microfluidic cell culture chip according to claim 8, wherein said inner face of said at least one protuberance at least partially faces said at least one perforation of said support.

10. The microfluidic cell culture chip according to claim 9, wherein an entirety of said inner face of said at least one protuberance faces said at least one perforation of said support, and when the value of the upper diameter d1 of said at least one perforation is greater than or equal to the value of the diameter d3 of said at least one protuberance, and a fourth axis, passing through the centre of said circular base and perpendicular to said support, and a first axis, passing through the centre of the upper section of said perforation and perpendicular to said support, coincide with each other; or when the value of the upper diameter d1 of said at least one perforation is greater than the value of the diameter d3 of said at least one protuberance, and the fourth axis, passing through the centre of said circular base and perpendicular to said support, and the first axis, passing through the centre of the upper section of said perforation and perpendicular to said support, are distinct from one another by a distance less than or equal to a value obtained by a formula: (value of d1−value of d3)/2.

11. The microfluidic cell culture chip according to claim 10, comprising at least two protuberances, wherein a maximum number of the at least two protuberances for a surface of the central unit of 1 cm² is equal to a formula $$\frac{\pi(d3/2)^2}{(l+d3) - \pi(d3/2)^2}$$

where l is a distance between two contiguous protuberances, a value of l being from 10 μm to 100 μm, and where d3 is a diameter of the circular base of one of said at least two protuberances.

12. The microfluidic cell culture chip according to claim 8, wherein the outer face of said at least one protuberance supports at least one adherent cell, and wherein the inner face of said protuberance supports at least one adherent cell.

13. The microfluidic cell culture chip according to claim 12, wherein said outer face of said at least one protuberance supports a first set of adherent cells at a stage of confluence, said first set being a set of stromal cells, and said inner face of said at least one protuberance supports a second set of adherent cells at the stage of the confluence, said second set being a set of epithelial cells.

14. The microfluidic cell culture chip according to claim 8, further comprising a solid lower module, said solid lower module comprising a lower unit which includes an upper face, a lower face, and at least one side face, the lower unit comprising at least one tubular-shaped duct comprising an upper orifice of diameter d4 having a third axis passing through the centre of said upper orifice and perpendicular to said support, and a lower orifice of diameter d5, and a base, said lower unit being integrated in said base, and forming a whole with said base, a value of the diameter d4 of said upper orifice being greater than or equal to a value of the diameter d5 of said lower orifice, and said value of the diameter d4 being greater than or equal to the value of the lower diameter d2 of said at least one perforation, said upper face of said lower unit comprising said upper orifice of the at least one tubular-shaped duct, and said lower orifice leading to, itself or by intermediate means, an outside of said base.

15. The microfluidic cell culture chip according to claim 14, wherein said lower module and said central module are assembled such that the upper orifice of the at least one tubular-shaped duct, of said upper face of said lower unit, opens over the at least one perforation of said support of said central unit, and the lower orifice of the at least one tubular-shaped duct, itself leads to an outside of the chip, or via an intermediate element including a reservoir capable of recovering liquids and making it possible for a conveyance to the outside of the chip via an outlet duct leading to the outside of the base of said lower module, wherein said upper face of said lower unit and said lower face of said support of said central unit have an identical shape and an identical surface to one another, and wherein said lower unit and said central unit are assembled by attachment elements situated respectively on each of the bases of the lower module and of the central module, so as to assemble, in a sealed manner, said upper face of said lower unit and said lower face of said support of said central unit.

16. The microfluidic cell culture chip according to claim 14, wherein said upper orifice of said at least one tubular-shaped duct leads to one single perforation of said support, and wherein an entirety of said perforation of said support faces said upper orifice of said at least one tubular-shaped duct, when the value of the lower diameter d2 of said perforation is equal to the value of the diameter d4 of said upper orifice of said at least one tubular-shaped duct, and the second axis, passing through the centre of a lower section of the perforation and perpendicular to said support, and the third axis, passing through the centre of said upper orifice of said at least one tubular-shaped duct and perpendicular to said support, are coincided with each other, or when the value of the lower diameter d2 of said perforation is less than the value of the diameter d4 of said upper orifice of said at least one tubular-shaped duct, and the second axis, passing through the centre of said lower section of the perforation and perpendicular to said support, and the third axis, passing through the centre of said upper orifice of said at least one tubular-shaped duct and perpendicular to said support, are distinct from one another by a distance less than or equal to a value obtained by a formula: (value of d4−value of d2)/2.

17. The microfluidic cell culture chip according to claim 14, wherein said lower module comprises at least two ducts, each of the at least two ducts having an upper orifice and a lower orifice, and wherein each of the upper orifices of the at least two ducts leads to the at least one perforation, and the lower orifices of the at least two ducts lead to an outside of the chip, respectively to at least two distinct sites, or the lower orifices of the at least two ducts lead to one same intermediate element including a reservoir capable of recovering liquids and making it possible for a conveyance to the outside of the chip via an outlet duct leading to the outside of the base of said lower module.

18. The microfluidic cell culture chip according to claim 14, further comprising an upper module comprising:
an upper unit, which includes a solid surface defining an open volume, edges of the solid surface being capable of being in contact with said central unit of said central module and delimiting the solid surface defining said open volume; and
a base,
said upper unit being integrated in said base, and forming a whole with said base.

19. The microfluidic cell culture chip according to claim 18, wherein said upper unit of said upper module and said central unit of said central module are assembled, such that said solid surface defining the open volume of said upper unit is positioned above said upper face of the 3D nanostructured porous membrane of said central unit, to form a closed space, delimited by said solid surface of said upper unit and said upper face of the 3D nanostructured porous membrane,
said solid surface and said upper face having an identical shape and an identical surface to one another,
said upper unit of said upper module and said central unit of said central module being assembled by attachment elements situated on each of the bases of the upper module and of the central module, so as to assemble, in a sealed manner, said solid surface defining the open volume of said upper unit and said upper face of the 3D nanostructured porous membrane of said central unit, and
said solid surface defining the open volume of said upper unit has two orifices respectively leading to an inlet/outlet duct, making it possible for said closed space to communicate with an outside of said chip via said inlet/outlet ducts which lead to the outside of the base.

20. The microfluidic cell culture chip according to claim 18, wherein said upper, central, and lower modules are assembled such that
said solid surface defining the open volume of said upper unit of said upper module is positioned above said upper face of the 3D nanostructured porous membrane of said central unit of said central module, and
the upper orifice of the at least one tubular-shaped duct, of said upper face of said lower unit of said lower module, opens on the at least one perforation of said support of said central unit,
said solid surface defining the open volume of said upper unit and said upper face of the 3D nanostructured porous membrane of said central unit having an identical shape and an identical surface to one another,
said upper face of said lower unit and said lower face of said support of said central unit having an identical shape and an identical surface to one another, and
said upper module, said central module, and said lower module being assembled by attachment elements situated on each of the respective bases.

* * * * *